United States Patent
Padmanabhan et al.

(10) Patent No.: US 7,911,617 B2
(45) Date of Patent: Mar. 22, 2011

(54) MINIATURIZED CYTOMETER FOR DETECTING MULTIPLE SPECIES IN A SAMPLE

(75) Inventors: Aravind Padmanabhan, Plymouth, MN (US); Bernard S. Fritz, Eagan, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 12/572,694

(22) Filed: Oct. 2, 2009

(65) Prior Publication Data

US 2010/0014068 A1 Jan. 21, 2010

Related U.S. Application Data

(60) Division of application No. 10/938,265, filed on Sep. 9, 2004, now Pat. No. 7,630,063, which is a continuation-in-part of application No. 10/304,773, filed on Nov. 26, 2002, and a continuation-in-part of application No. 10/225,325, filed on Aug. 21, 2002, now Pat. No. 6,970,245.

(51) Int. Cl.
*G01N 33/48* (2006.01)
*G01N 33/50* (2006.01)
*G01J 3/45* (2006.01)
*G01B 9/02* (2006.01)

(52) U.S. Cl. .......... 356/450; 356/451; 356/39; 356/246; 356/436; 436/63; 436/173

(58) Field of Classification Search .......... 356/432–444, 356/246, 27–28, 39–41, 317, 334, 336–337, 356/450, 453, 491; 436/52, 63, 73, 523, 436/531; 422/82.08

See application file for complete search history.

(56) References Cited

U.S. PATENT DOCUMENTS

| | | |
|---|---|---|
| 3,721,824 A | 3/1973 | Bristol |
| 3,774,042 A | 11/1973 | Engel |
| 3,822,095 A | 7/1974 | Hirschfeld |
| 3,928,094 A | 12/1975 | Angell |
| 3,976,862 A | 8/1976 | Curbelo |
| 4,284,412 A | 8/1981 | Hansen et al. |
| 4,293,221 A | 10/1981 | Kay et al. |
| 4,478,076 A | 10/1984 | Bohrer |
| 4,478,077 A | 10/1984 | Bohrer et al. |

(Continued)

FOREIGN PATENT DOCUMENTS

AU 518190 9/1981

(Continued)

OTHER PUBLICATIONS http://www.micronics.net/tsensor.htm, pp. 1-4, downloaded Jun. 14, 2000.

(Continued)

*Primary Examiner* — Sang Nguyen
(74) *Attorney, Agent, or Firm* — Seager Tufte & Wickham LLC

(57) ABSTRACT

A system for scattered light and simultaneous multi-color (e.g., greater than sixteen colors) fluorescence light detecting, and for analyzing, classifying and identifying biological particles and items of interest. A sample to be tested may be entered in a disposable microfluidic cartridge which in turn is insertable in a portable, hand-holdable, or wearable miniaturized cytometer instrument. The present system may be incorporated in the cytometer instrument. It may have significant application relative to biological warfare, environmental substances, the medical field and other fields.

10 Claims, 37 Drawing Sheets

U.S. PATENT DOCUMENTS

| | | |
|---|---|---|
| 4,501,144 A | 2/1985 | Higashi et al. |
| 4,599,000 A | 7/1986 | Yamada |
| 4,651,564 A | 3/1987 | Johnson et al. |
| 4,683,159 A | 7/1987 | Bohrer et al. |
| 4,695,034 A | 9/1987 | Shimizu et al. |
| 4,704,033 A | 11/1987 | Fay et al. |
| 4,714,345 A | 12/1987 | Schrader |
| 4,745,279 A | 5/1988 | Karkar et al. |
| 4,764,013 A * | 8/1988 | Johnston ............. 356/484 |
| 4,818,263 A | 4/1989 | Mitch |
| 4,838,688 A | 6/1989 | Rhoads |
| 4,844,334 A | 7/1989 | Hennel |
| 4,874,949 A | 10/1989 | Harris et al. |
| 4,905,169 A * | 2/1990 | Buican et al. ............ 356/365 |
| 4,911,616 A | 3/1990 | Laumann, Jr. |
| 4,932,989 A | 6/1990 | Presby |
| 4,983,359 A | 1/1991 | Tomioka et al. |
| 4,989,978 A | 2/1991 | Groner |
| 5,017,497 A | 5/1991 | Gerard de Grooth et al. |
| 5,050,429 A | 9/1991 | Nishimoto et al. |
| 5,078,581 A | 1/1992 | Blum et al. |
| 5,082,242 A | 1/1992 | Bonne et al. |
| 5,085,562 A | 2/1992 | Van Lintel |
| 5,096,388 A | 3/1992 | Weinberg |
| 5,108,623 A | 4/1992 | Cangelosi et al. |
| 5,117,466 A * | 5/1992 | Buican et al. ............ 382/133 |
| 5,129,794 A | 7/1992 | Beatty |
| 5,159,397 A | 10/1992 | Kosaka et al. |
| 5,171,132 A | 12/1992 | Miyazaki et al. |
| 5,176,358 A | 1/1993 | Bonne et al. |
| 5,185,265 A | 2/1993 | Steen et al. |
| 5,185,641 A | 2/1993 | Igushi et al. |
| 5,194,909 A | 3/1993 | Tycko |
| 5,208,651 A * | 5/1993 | Buican ................... 356/451 |
| 5,219,278 A | 6/1993 | Van Lintel |
| 5,224,843 A | 7/1993 | Van Lintel |
| 5,244,537 A | 9/1993 | Ohnstein |
| 5,247,339 A | 9/1993 | Ogino |
| 5,323,999 A | 6/1994 | Bonne et al. |
| 5,367,474 A | 11/1994 | Auer et al. |
| 5,378,633 A | 1/1995 | Von Behrens et al. |
| 5,441,597 A | 8/1995 | Bonne et al. |
| 5,452,878 A | 9/1995 | Gravesen et al. |
| 5,457,526 A | 10/1995 | Kosaka |
| 5,492,833 A | 2/1996 | Rodriguez et al. |
| 5,528,045 A | 6/1996 | Hoffman et al. |
| 5,567,627 A | 10/1996 | Lehnen |
| 5,570,193 A | 10/1996 | Landa et al. |
| 5,601,080 A | 2/1997 | Oppenheimer |
| 5,616,501 A | 4/1997 | Rodriguez et al. |
| 5,633,724 A | 5/1997 | King et al. |
| 5,650,847 A | 7/1997 | Maltsev et al. |
| 5,683,159 A | 11/1997 | Johnson |
| 5,684,575 A | 11/1997 | Steen |
| 5,716,852 A | 2/1998 | Yager et al. |
| 5,717,631 A | 2/1998 | Carley et al. |
| 5,723,341 A | 3/1998 | Truett |
| 5,726,751 A | 3/1998 | Altendorf et al. |
| 5,736,410 A | 4/1998 | Zarling et al. |
| 5,739,902 A | 4/1998 | Gjelsnes et al. |
| 5,757,476 A | 5/1998 | Nakamoto et al. |
| 5,760,900 A | 6/1998 | Ito et al. |
| 5,784,157 A | 7/1998 | Gorfinkel et al. |
| 5,793,485 A | 8/1998 | Gourley |
| 5,799,030 A | 8/1998 | Brenner |
| 5,822,170 A | 10/1998 | Cabuz et al. |
| 5,828,450 A | 10/1998 | Dou et al. |
| 5,836,750 A | 11/1998 | Cabuz |
| 5,837,547 A | 11/1998 | Schwartz |
| 5,839,807 A | 11/1998 | Perlo |
| 5,863,502 A | 1/1999 | Southgate et al. |
| 5,880,474 A | 3/1999 | Norton et al. |
| 5,888,823 A | 3/1999 | Matsumoto et al. |
| 5,893,722 A | 4/1999 | Hibbs-Brenner et al. |
| 5,901,939 A | 5/1999 | Cabuz et al. |
| 5,922,210 A | 7/1999 | Brody et al. |
| 5,932,100 A | 8/1999 | Yager et al. |
| 5,946,083 A | 8/1999 | Melendez et al. |
| 5,948,684 A | 9/1999 | Weigl et al. |
| 5,970,315 A | 10/1999 | Carley et al. |
| 5,971,158 A | 10/1999 | Yager et al. |
| 5,972,710 A | 10/1999 | Weigl et al. |
| 5,974,867 A | 11/1999 | Forster et al. |
| 6,007,775 A | 12/1999 | Yager |
| 6,032,689 A | 3/2000 | Tsai et al. |
| 6,046,807 A | 4/2000 | Chandler |
| 6,054,335 A | 4/2000 | Sun et al. |
| 6,078,390 A | 6/2000 | Bengtsson |
| 6,082,185 A | 7/2000 | Saaski |
| 6,091,197 A | 7/2000 | Sun et al. |
| 6,091,537 A | 7/2000 | Sun et al. |
| 6,094,293 A | 7/2000 | Yokoyama et al. |
| 6,097,485 A | 8/2000 | Lievan |
| 6,097,859 A | 8/2000 | Solgaard et al. |
| 6,106,245 A | 8/2000 | Cabuz |
| 6,109,889 A | 8/2000 | Zengerle et al. |
| 6,116,756 A | 9/2000 | Peeters et al. |
| 6,122,536 A | 9/2000 | Sun et al. |
| 6,124,663 A | 9/2000 | Haake et al. |
| 6,133,995 A | 10/2000 | Kubota |
| 6,139,800 A | 10/2000 | Chandler |
| 6,179,586 B1 | 1/2001 | Herb et al. |
| 6,184,607 B1 | 2/2001 | Cabuz et al. |
| 6,215,221 B1 | 4/2001 | Cabuz et al. |
| 6,221,671 B1 | 4/2001 | Groner et al. |
| 6,228,652 B1 | 5/2001 | Rodriguez et al. |
| 6,237,619 B1 | 5/2001 | Maillefer et al. |
| 6,240,944 B1 | 6/2001 | Ohnstein et al. |
| 6,249,341 B1 | 6/2001 | Basiji et al. |
| 6,281,975 B1 | 8/2001 | Munk |
| 6,312,393 B1 | 11/2001 | Abreu |
| 6,382,228 B1 | 5/2002 | Cabuz et al. |
| 6,488,896 B2 * | 12/2002 | Weigl et al. ............. 422/101 |
| 6,549,275 B1 | 4/2003 | Cabuz et al. |
| 6,597,438 B1 | 7/2003 | Cabuz et al. |
| 6,683,314 B2 | 1/2004 | Oostman, Jr. et al. |
| 6,710,870 B1 | 3/2004 | Marowsky et al. |
| 6,791,086 B2 | 9/2004 | Russell |
| 6,853,455 B1 * | 2/2005 | Dixon et al. ............ 356/453 |
| 6,870,612 B2 | 3/2005 | Jiang |
| 6,887,711 B1 | 5/2005 | Diem et al. |
| 6,970,245 B2 | 11/2005 | Fritz et al. |
| 7,420,659 B1 * | 9/2008 | Cabuz et al. ............ 356/39 |

FOREIGN PATENT DOCUMENTS

| | | |
|---|---|---|
| EP | 0269076 | 6/1988 |
| EP | 1134548 | 9/2001 |
| EP | 1001326 | 8/2005 |
| EP | 1890390 | 2/2008 |
| JP | 61066947 | 4/1986 |
| JP | 10073528 | 3/1998 |
| JP | 2000056228 | 2/2000 |
| WO | WO 95/27199 | 10/1995 |
| WO | WO 99/60397 | 11/1999 |
| WO | WO 01/09598 | 2/2001 |
| WO | WO 02/10713 | 2/2002 |
| WO | WO 02/10714 | 2/2002 |

OTHER PUBLICATIONS http://www.micronics.net/hfilter.htm, pp. 1-3, downloaded Jun. 14, 2000.

http://www.micronics.net/mcytometry.htm, pp. 1-4, downloaded Jun. 14, 2000.

http://www.micronics.net/orcafluidics.htm, pp. 1-4, downloaded Jun. 14, 2000.

Altendorf et al., "Implementation of Novel Optical Detection Methods for Clinically Important Blood Analytes Using Microfabricated Flow Structures (T-Sensors™)", MicroTAS 98, Banff, Canada, Apr. 1998.

Altendorf et al., "Microfabrication Technology for Research and Diagnostics, Silicon Microchannel Optical Flow Cytometry", SPIE Proceedings, Biomedical Optics 96, Jan. 1996.

Altendorf et al, "Results Obtained Using a Prototype Microfluidics-Based Hematology Analyzer", SPIE Biomedical Optics 97, 1997.

Altendorf et al., "Differential Blood Cell Counts Obtained Using a Microchannel Based Flow Cytometer", Solid State Sensors & Actuators, vol. 1, 531, 1997.

Cabuz et al., "Mesoscopic Sampler Based on 3D Array of Electrostatically Activated Diaphragms", The 10th Int. Conf. On Solid-State Sensors and Actuators, Transducers'99, Jun. 7-12, 1999, Sendai Japan, p. 1890-1.

Darling et al., "Integration of Microelectrodes With Etched Microchannels for In-Stream Electrochemical Analysis", MicroTAS 98, Banff, Canada, Apr. 1998.

Fedder et al., "Laminated High-Aspect-Ratio Microstructures in a Conventional CMOS Process", Proc. Micro Electro Mechanical Systems Workshop, MEMS 96, San Diego, California, Feb. 11-15, 1996, pp. 13-18.

Hatch et al., "Microfluidic Approaches to Immunoassays", SPIE conference on Micromachining and Microfabrication Symposium at Santa Clara, CA, Sep. 20-22, 1999.

Huang et al., "Development of a Flow Cytometry Based Miniature Chemical Fluid Analysis System Using Fluorescent Microbeads", SPIE Biomedical Optics, BIOS 97, conference proceedings, 1997.

Lehman et al., "High-Frequency Modulation Characteristics of Red VCSELs", Electronics Letters, Feb. 13, 1997, vol. 33(4), pp. 298-300. Copyright 1997 IEEE.

Ohnstein et al., "Micromachined Silicon Microvalve", Proceedings of MEMS, 1990, IEEE Micro Electromechanical Systems, Napa Valley, California, Feb. 11-14, 1990, pp. 95-98.

Roulet et al., "Fabrication of Multilayer Systems Combining Microfluidic and Microoptical Elements for Fluorescence Detection," Journal of Microelectromechanical Systems, vol. 10 No. 44, pp. 483-491, Dec. 4, 2001.

Shapiro, "Practical Flow Cytometry", third edition, 1995, p. 237.

Strzelecka et al., "Parallel Free-Space Optical Interconnect Based on Arrays of Vertical-Cavity Lasers and Detectors with Monolithic Microlenses", Applied Optics, v. 37(14), May 10, 1998, pp. 2811-2821. Copyright 1998 Optical Society of America.

Terstappen et al., "Four-Parameter White Blood Cell Differential Counting Based on Light Scattering Measurements", Alan R. Liss, Inc., Cytometery 9:39-43, 1988.

Toshiyoshi et al., "Micromechanical Lens Scanner for Fiber Optic Switches", Proc. 3rd International Conference on Micro Opto Electro Mechanical Systems (MOEMS 99), Aug. 30-Sep. 1, 1999, Mainz, Germany, pp. 165-170.

Toshiyoshi et al., "Surface Micromachined 2D Lens Scanner Array", Proc. IEEE?LEOS International Coference on Optical EMMS/Sheraton Kauai Resort, Kauai, Hawaii, Aug. 21-24, 2000, 3 pages.

Tuantranont et al., "MEMS-Controllable Microlens Array for Beam Steering and Precision Alignment in Optical Interconnect Systems", Solid-State Sensor and Actuator Workshop, Hilton Head Island, South Carolina, Jun. 4-8, 2000, pp. 101-104.

Tuantranont et al., "Flip Chip Integration of Lenslet Arrays on Segmented Deformable Micromirrors", Part of the Symposium on Design, Test and Microfabrication of MEMS and MOEMS, Paris, France, Mar.-Apr. 1999, SPIE vol. 3680, 0277-786X/99, pp. 668-678.

Weigl et al., "Diffusion-Based Optical Chemical Detection in Silicon Flow Structures", Analytical Methods & Instrumentation, µTTAS 96 special edition, 1996.

Weigl et al., "Fluorescence and Absorbance Analyte Sensing in Whole Blood and Plasma Based on Diffusion Separation in Silicon-Microfabricated Flow Structures (T-Sensors™)", Biomedical Optics, vol. 6, No. 1, Jul. 1997.

Weigl et al, "Optical and Electrochemical Diffusion-Based Detection of Analytes in Complex Samples Using Microfabricated Flow Structures (T-SensorSTM)", Micro- and nanofabn'cated electro-optical mechanical systems for biomedical and environmental applications II- SPIE vol. 3606, Jan. 25-26, 1999.

Weigl et al., "Rapid Sequential Chemical Analysis Using Multiple Fluorescent Reporter Beads", µTTAS 96 Conference Proceedings, 1996.

Weigl et al, "Silicon-Microfabricated Diffusion-Based Optical Chemical Sensor", Reprint from "Sensors & Actuators" B 38-39, 452-457, 1997.

Weigl et al, "Simultaneous Self-Referencing Analyte Determination in Complex Sample Solutions Using Microfabricated Flow Structures (T-Sensors™)", Proceedings of MicroTAS 98, 81-4, Banff, Canada, 1998.

Weigl, "Whole Blood Assays Using Microfluidics-Based T-SensorSTm Technology", Medical Design Online, http://news.medicaldesignonline.com/featuresarticles/19990416-5922.html, Apr. 1999.

Weigl, "Microfluidic Diffusion Based Electrochemical Detection Using Microfabricated Flow Structures (T-Sensors™)", Analytical Chemistry, submitted 1999.

Weigl et al, "Microfluidic Diffusion-Based Separation and Detection", Science, vol. 283, pp. 346-347, Jan. 15, 1999.

Yager et al., "Applying Microfluidic Chemical Analytical Systems to Imperfect Samples", Micro Total Analysis Systems 98, D. Harrison & A. van den Berg (ed.), Kluwer Academic Publishers, Dordrecht, 207-212, 1998.

Yager et al., "Design of Microfluidic Sample Preconditioning Systems for Detection of Biological Agents in Environmental Samples", Yager, M. et al., SPIE Proceedings, 3515, 252-259, 1998.

* cited by examiner

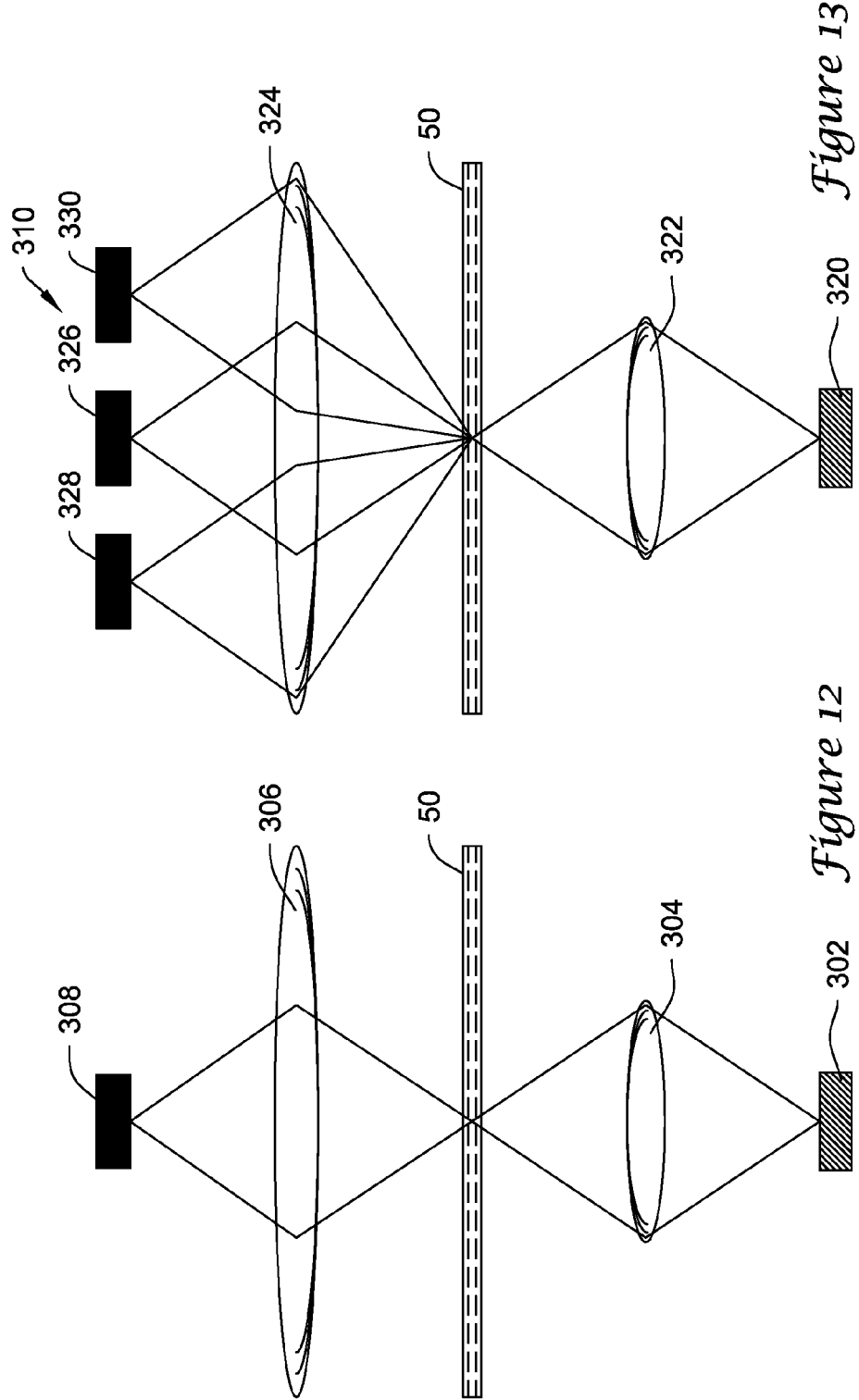

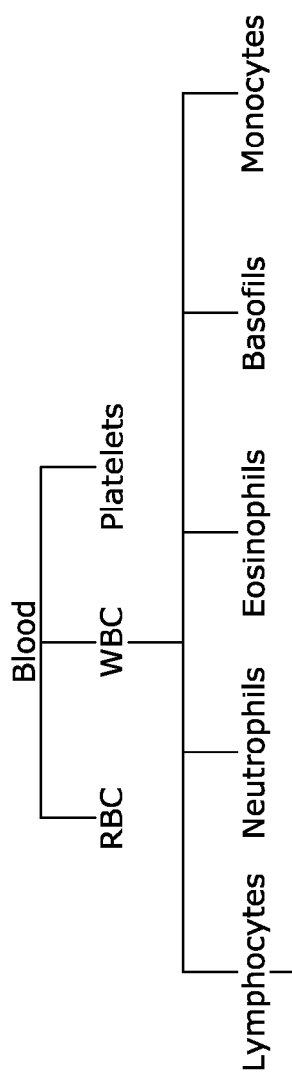
*Figure 18*
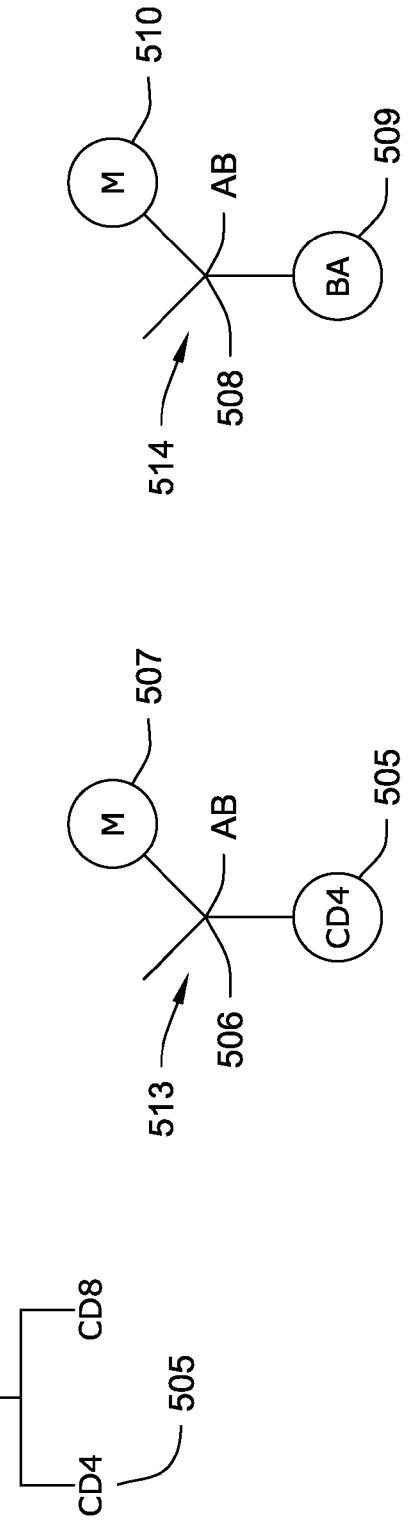
*Figure 19a*
*Figure 19b*

| Parameter | AIDS Assay | Malaria Assay |
|---|---|---|
| AIDS markers/malaria species | CD4, CD45 | P. falciparum, P. vivax |
| No. of fluorescent channels | 2 | 2 |
| No. of scattering channels | 1 (90°) | 1 (90°) |
| Optional scattering channels (for total WBC count and three-part differential) | 2 (1° -3°, 4°-13°) | 2 (1° -3°, 4°-13°) |
| Reagent reservoirs on-card | 4 | 4 |
| Flow sensors on-card | 4 | 4 |
| No. of cytometer measurement channels on the cartridge (without three-part differential capability) | 1 | 1 |
| No. of cytometer measurement channels on the cartridge (with three-part differential capability) | 2 | 2 |

*Figure 38*

MINIATURIZED CYTOMETER FOR DETECTING MULTIPLE SPECIES IN A SAMPLE

This application is a divisional of U.S. patent application Ser. No. 10/938,265, by Aravind Padmanabhan et al., filed Sep. 9, 2004, and entitled "Miniaturized Cytometer for Detecting Multiple Species in a Sample", which is a continuation-in-part of U.S. patent application Ser. No. 10/304,773, by Aravind Padmanabhan et al., filed Nov. 26, 2002, and entitled "Portable Scattering and Fluorescence Cytometer"; all of which are incorporated herein by reference. This application is a divisional of U.S. patent application Ser. No. 10/938,265, filed Sep. 9, 2004, which is a continuation-in-part of U.S. patent application Ser. No. 10/225,325, by Bernard Fritz et al., filed Aug. 21, 2002, and entitled "Optical Alignment Detection System"; all of which are incorporated herein by reference.

BACKGROUND

This invention is related to U.S. Pat. No. 6,549,275 B1, by Cabuz et al., issued Apr. 15, 2003, and entitled "Optical Detection System for Flow Cytometry"; U.S. Pat. No. 6,597,438 B1, by Cabuz et al., issued Jul. 22, 2003, and entitled "Portable Flow Cytometer"; U.S. Pat. No. 6,382,228 B1, by Cabuz et al., issued May 7, 2002, and entitled "Fluid Driving System for Flow Cytometry"; U.S. Pat. No. 6,700,130 B2, issued Mar. 2, 2004, by Fritz, and entitled "Optical Detection System for Flow Cytometry"; and U.S. Pat. No. 6,240,944 B1, by Ohnstein et al., issued Jun. 5, 2001, and entitled "Addressable Valve Arrays for Proportional Pressure or Flow Control"; all of which are incorporated herein by reference.

The present invention relates generally to flow cytometers. More particularly, the present invention relates to portable flow cytometers that sense optical properties of microscopic particles or components in a flow stream.

Flow cytometry is a technique that is used to determine certain physical and chemical properties of microscopic biological particles or components by sensing certain optical properties of the particles or components. To do so, for instance, the particles are arranged in single file using hydrodynamic focusing within a sheath fluid. The particles are then individually interrogated by a light beam. Each particle scatters the light beam and produces a scatter profile. The scatter profile is often identified by measuring the light intensity at different scatter angles. Certain physical and/or chemical properties of each particle can then be determined from the scatter profile. The term "fluid" may be used here as a generic term that includes liquids and gases as species.

Flow cytometry is currently used in a wide variety of applications including hematology, immunology, genetics, food science, pharmacology, microbiology, parasitology and oncology, to name a few. A limitation of many commercially available flow cytometer systems is that they are relatively large bench top instruments that must remain in a central laboratory environment. Accordingly, the use of such flow cytometers is often not available in remote locations or for continuous hematological monitoring.

SUMMARY

The present invention overcomes many of the disadvantages of the prior art by providing a highly miniaturized portable and wearable cytometer that can be used at remote locations, such as at home or in the field. Such a flow cytometer may help improve healthcare of patients by providing detailed individual hematological evaluation and uncovering statistical trends. By detecting an infection early, the infection may be more readily treatable.

In military applications, the portable miniaturized cytometer of the present invention may help save lives by providing early detection of infection due to biological agents. It is known that expanded activity in the biological sciences has increased the probability of accidental exposure to dangerous biological agents. The ease of manufacturing such agents also raises a serious threat to their use by terrorists, regional powers or developing third world nations. The lack of safeguards in international agreements outlawing biological warfare, and compelling evidence that those agreements may have been violated, reinforces the need for a strong capability for biological defense. Pre-exposure detection of pathogen agents, as well as post-exposure detection of incipient infections may be used cooperatively to ensure efficient protection during biological warfare.

As part of the body's natural defense against antigens, the white blood cell count increases at the onset of infection. There are several types of white blood cells including neutrophils, lymphocytes, monocytes, eosinophils and basofils. Lymphocytes create antibodies that attack the invaders and mark them for destruction by the neutrophils and macrophages. In an individual without chronic diseases (such as tuberculosis or cancer), an increase in the percentage of lymphocytes in the overall white cell count is an indication of a viral infection. On the other side, an increase in the percentage of the neutrophils is an indication of a developing bacterial infection. Through counting of neutrophils and lymphocytes, a clear infection warning can be issued with differentiation between viral or bacterial causes.

The first clinical symptoms of infection from some bacterial agents such as bacillus anthrax appear after one to six days. In 99% of the cases, patients showing symptoms from anthrax cannot be treated, and will most likely die. However, if treatment is given before the first symptoms appear, most patients can be successfully treated. Accordingly, it would be highly desirable to provide an early alert and potential therapeutic intervention for hematologic abnormalities before symptoms occur. In many cases, such an early alert and treatment may greatly improve the outcome for many patients.

In an illustrative example of the present invention, a portable miniaturized cytometer is provided for identifying and/or counting selected particles in a fluid sample such as a blood sample. One illustrative miniaturized portable cytometer includes a fluid receiver for receiving the fluid sample. One or more reservoirs are provided for storing supporting fluids such as lyse and sheath fluids. For many commercial flow cytometer systems, a precision fluid driving system is used for providing precise pressures to the fluids. A limitation of this approach is that precision fluid driving systems can be bulky, complex and may require significant power.

To avoid many of these limitations, an illustrative example uses a non-precision fluid driver that is controlled by a closed loop feedback path. The non-precision fluid driver is coupled to the fluid receiver and the various supporting fluid reservoirs, and applies separate pressures to the sample fluid and the supporting fluids. To control the velocity of the sample fluid and the supporting fluids, one or more valves are coupled to the fluid driver. The valves are used to regulate the non-precision pressures that are applied to the sample fluid and the supporting fluids by the non-precision fluid driver.

To complete the feedback loop, flow sensors are provided downstream of the fluid driver to measure the fluid velocity of the sample fluid and the supporting fluids. A controller or processor receives the signals from the flow sensors, and adjusts the appropriate valves so that the desired fluid velocities of the sample fluid and supporting fluids are achieved. The flow sensors are preferably thermal anemometer type flow sensors.

In one illustrative example, the non-precision fluid driver is manually powered. A manually powered fluid driver may include, for example, a bulb with check valve or a plunger. In either case, the manually generated pressure is preferably provided to a first pressure chamber. A first valve is then provided for controllably releasing the pressure in the first pressure chamber to a second pressure chamber. A second valve may be provided in the second pressure chamber for controllably venting the pressure in the second pressure chamber. The controller opens the first valve when the fluid flow in the downstream fluid stream drops below a first predetermined value and opens the second valve when the fluid flow in the downstream fluid stream increases above a second predetermined value. Each valve is preferably an array of electrostatically actuated microvalves that are individually addressable and controllable.

The controlled sample fluid and supporting fluids are provided to a fluidic circuit. The fluidic circuit performs hydrodynamic focusing, which causes the desired particles to fall into single file along a core stream surrounded by a sheath fluid. One or more light sources or light source arrangements provide light through the flow stream, and one or more light detectors or light detector arrangements detect the scatter profile and fluorescence of the particles in the flow stream. An arrangement may have one or more light sources and/or one or more light detectors. An arrangement may include a single optical device or element or an array of such items. A processing block uses the output signals from the light detectors to identify and/or count selected particles in the core stream.

The miniaturized portable cytometer may be provided in a housing sufficiently small to be appropriately and comfortably "wearable" on a person. In one illustrative example of the invention, the housing is sized similar to a wrist watch. The wearable housing may include, for example, a base, a cover, and a hinge that secures the base to the cover. The non-precision fluid driver and regulating valves may be incorporated into the cover, while the fluid reservoirs, flow sensors and fluidic circuit may be incorporated into a removable cartridge that is inserted into the housing. Preferably, the fluidic circuit dilutes the blood sample, performs red cell lysing, and performs hydrodynamic focusing for flow and core stream formation. The light sources are preferably situated in either the base or the cover, and aligned with the flow stream of the removable cartridge. The light detectors are preferably provided generally opposite the light sources. The processor and batteries may be provided in either the base or the cover of the housing.

The light source may include one or a linear array of first light sources along a first light source axis. The first light source axis may be rotated relative to the central axis of the flow stream. A lens may be provided adjacent each light source to focus the light at the particles in the core stream. A detector or set of light detectors may then be placed in-line with the light source or each of the light sources. Such an arrangement can be used to determine, for example, the alignment and width of the core stream within the flow stream. If the core stream of particles is not in proper alignment, the controller can adjust the fluid velocity of the sample fluid or one of the supporting fluids to bring the core stream into alignment. The light detector or set of light detectors may also be used to detect the velocity and size of each particle, as well as the number of particles.

Another light source or set of the light sources may be provided along second light source axis. A lens may be provided adjacent each light source to focus the light at the particles in the core stream. A second detector or set of light detectors may then be placed on either side of the in-line position of each light source for measuring the small angle scattering (SALS) produced by selected particles in the flow stream.

The second light source or set of light sources may also be used in conjunction with the first set of light sources to determine the time-of-flight or velocity of the particles in the flow stream. By knowing the velocity of the particles, small variations in the flow rate caused by the fluid driver can be minimized or removed by the controller.

A third light source or set of light sources may be provided along a third light source axis. A lens may be provided adjacent each light source to provide collimated light to the flow stream. An annular light detector or detectors may then be placed opposite the light source or light sources for measuring the forward angle scattering (FALS) produced by the selected particles in the flow stream. Each of the first, second and third light sources or sets of light sources may include an array of lasers such as vertical cavity surface emitting lasers (VCSELs) fabricated on a common substrate. Each of the first, second and third detectors or sets of light detectors may include a photo detector or an array of photo detectors such as p-i-n photodiodes, GaAs photodiodes with integrated FET circuits, resonant cavity photo detectors (RCPDs), or any other suitable light detectors.

The selected particles are preferably neutrophils and/or lymphocytes white blood cells. By examining the scatter profile of each particle, the miniaturized portable cytometer of the present invention identifies and counts the neutrophils and lymphocytes in a blood sample, and provides a clear infection warning with differentiation between viral and bacterial causes.

Another part of the invention uses of fluorescence to further identify and analyze various white cells. Antibodies may be associated with particular white blood cells. The antibodies have markers or tags attached to them. These white blood cells may be impinged with light which causes their associated markers or tags to fluoresce and emit light. The light may be collected, filtered as needed, and directed to one or more photo detectors. This detection may be used to identify and monitor specific subclasses of white cells and blood-based proteins, among other things.

In sum, this miniaturized portable cytometer has two optical detection subsystems—scattering and fluorescing. It also has a low power electronic system, a compact fluid driving system, and may use direct/unprocessed blood samples and disposable microfluidic cartridge.

BRIEF DESCRIPTION OF THE DRAWINGS

FIG. 12 is a schematic diagram showing an illustrative light source and detector pair of the first array shown in FIG. 11;

FIG. 13 is a schematic diagram showing an illustrative light source and detector pair of the second array shown in FIG. 11;

FIG. 18 is a diagram of the blood hierarchy emphasizing an area of cytometer application;

FIGS. 19a and 19b show the antibody and marker structure associated with the cell or bacteria of interest;

FIGS. 25a and 25b are graphs of FALS versus SALS and FALS versus LALS data, respectively;

FIG. 38 is a table of characteristics of the present cytometer for AIDS and malaria assays;

DESCRIPTION

Figure 1:
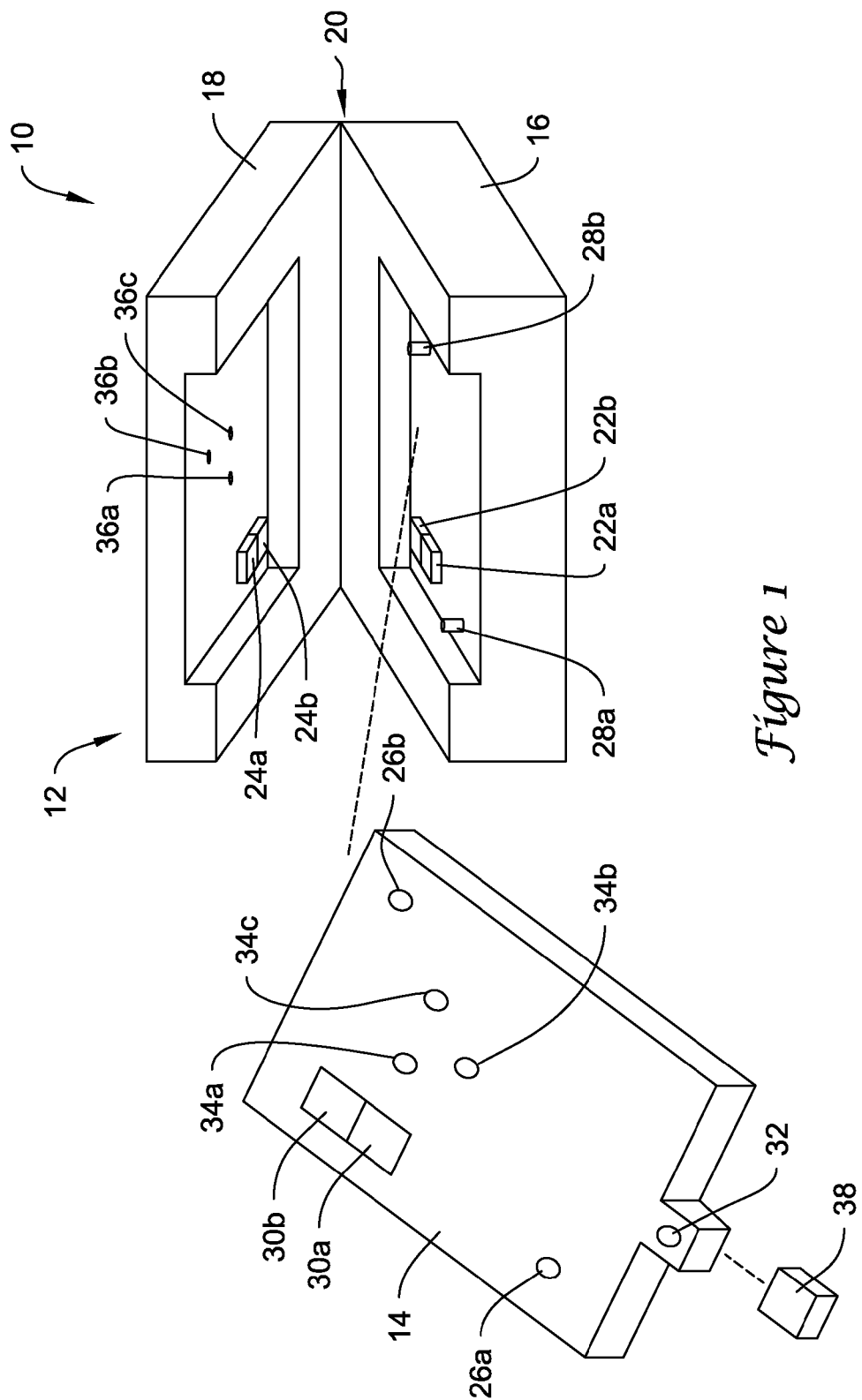
FIG. 1 is a perspective view of an illustrative portable cytometer in accordance with the present invention.

FIG. 1 is a perspective view of an illustrative miniaturized portable cytometer in accordance with the present invention. The cytometer is generally shown at 10, and includes a housing 12 and a removable or replaceable cartridge 14. The illustrative housing 12 includes a base 16, a cover 18, and a hinge 20 that attaches the base 16 to the cover 18. The base 16 includes light sources 22a and 22b, associated optics and the necessary electronics for operation of the cytometer. The cover 12 includes a manual pressurizing element, pressure-chambers with control microvalves, and light detectors 24a and 24b with associated optics.

The removable cartridge 14 preferably receives a sample fluid via a sample collector port 32. A cap 38 may be used to protect the sample collector port 32 when the removable cartridge 14 is not in use. The removable cartridge 14 preferably performs blood dilution, red cell lysing, and hydrodynamic focusing for core formation. The removable cartridge 14 may be constructed similar to the fluidic circuits available from Micronics Technologies, some of which are fabricated using a laminated structure with etched channels.

The removable structure or cartridge 14 is inserted into the housing when the cover 18 is in the open position. The removable cartridge 14 may include holes 26a and 26b for receiving registration pins 28a and 28b in the base 16, which help provide alignment and coupling between the different parts of the instrument. The removable cartridge 14 also preferably includes transparent flow stream windows 30a and 30b, which are in alignment with the arrays of the light sources 22a and 22b, and light detectors 24a and 24b. When the cover is moved to the closed position, and the system is pressurized, the cover 18 provides controlled pressures to pressure receiving ports 34a, 34b, and 34c in the removable cartridge 14 via pressure providing ports 36a, 36b and 36c, respectively.

To initiate a test, the cover 18 is lifted and a new cartridge 14 is placed and registered onto the base 16. A blood sample is introduced into the sample collector 32. The cover 18 is closed and the system is manually pressurized. Once pressurized, the instrument performs a white blood cell cytometry measurement. The removable cartridge 14 provides blood dilution, red cell lysing, and hydrodynamic focusing for core formation. The light sources 22a and 22b, light detectors 24a and 24b and associated control and processing electronics perform differentiation and counting of white blood cells based on light scattering fluorescent signals. Rather than using a hinged construction for the housing 12, it is contemplated that a sliding cartridge slot or any other suitable construction may be used.

Figure 2:
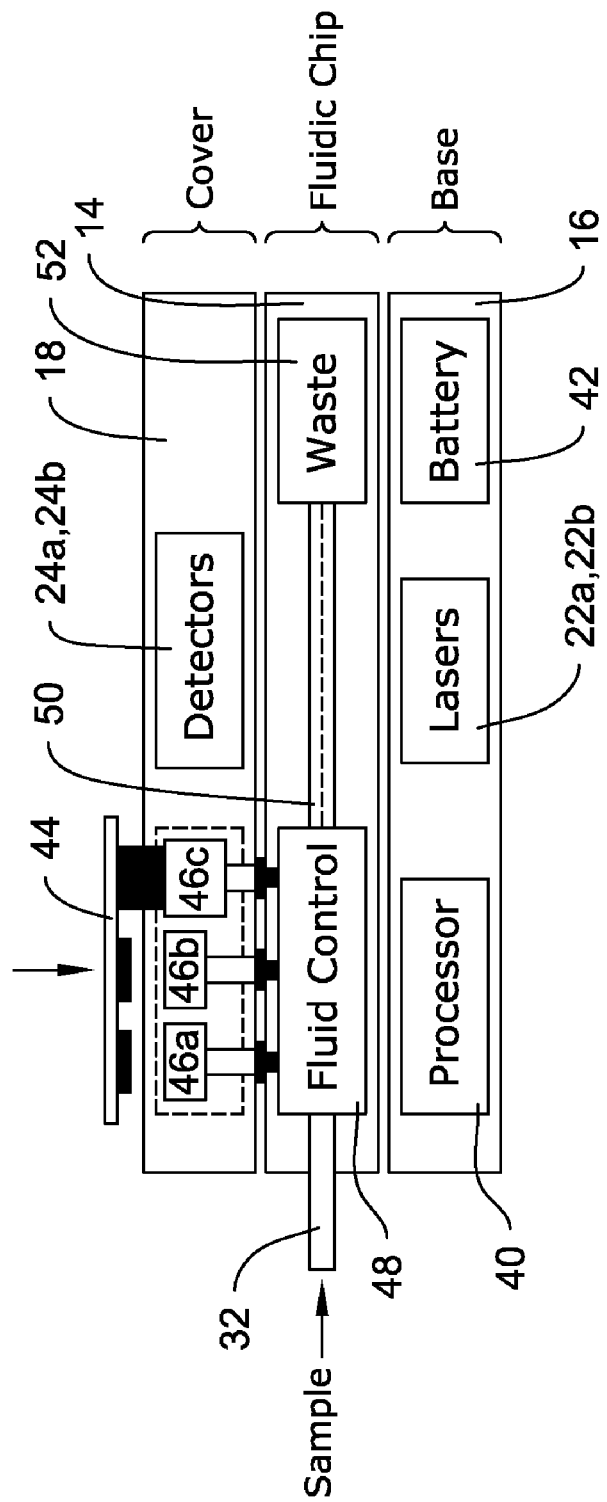
FIG. 2 is a schematic view of the illustrative portable cytometer of FIG. 1.

FIG. 2 is a schematic view of the illustrative cytometer of FIG. 1. As above, the base 16 may include light sources 22a and 22b, associated optics and the necessary control and processing electronics 40 for operation of the cytometer. The base 16 may also include a battery 42 for powering the cytometer. The cover 12 is shown having a manual pressurizing element 44, pressure-chambers 46a, 46b and 46c with control microvalves, and light detectors 24a and 24b with associated optics.

The removable cartridge 14 may receive a sample fluid via the sample collector port 32. When pressurized by the cover 18, the removable cartridge 14 performs blood dilution, red cell lysing, and hydrodynamic focusing for core formation in the present device. Once formed, the core is provided down a flow stream path 50, which passes the flow stream windows 30a and 30b of FIG. 1. The light sources 22a and 22b, and associated optics in the base provide light through and to the core stream via the flow stream windows 30a and 30b. The light detectors 24a and 24b, and associated optics receive scattered and non-scattered light from the core, also via the flow stream windows 30a and 30b, respectively. The controller or processor 40 receives output signals from the detectors 24a and 24b, and differentiates, identifies and counts selected white blood cells that are present in the core stream.

It is contemplated that the removable cartridge 14 may include a fluid control block 48 for helping control the velocity of each of the fluids. In the illustrative example, the fluid control block 48 includes flow sensors for sensing the velocity of the various fluids and reports the velocities to the controller or processor 40. The controller or processor 40 may then adjust the microvalves associated with pressure-chambers 46a, 46b and 46c to achieve the desired pressures and thus desired fluid velocities for proper operation of the cytometer.

Because blood and other biological waste can spread disease, the removable cartridge 14 preferably has a waste reservoir 52 downstream of the flow stream windows 30a and 30b. The waste reservoir 52 receives and stores the fluid of the flow stream in the removable cartridge 14. When a test is completed, the removable cartridge may be removed and disposed of, preferably in a container compatible with biological waste.

Figure 3:
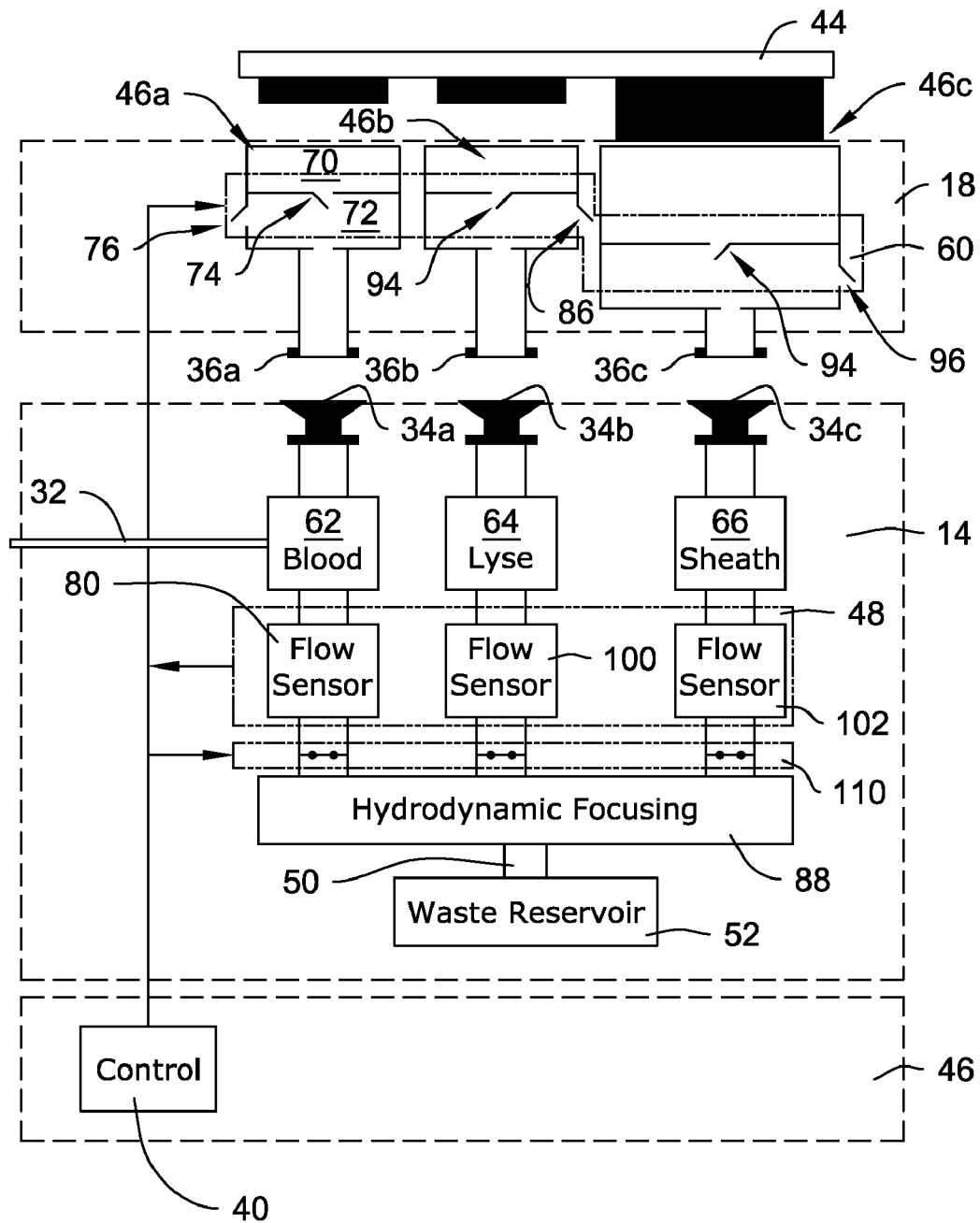
FIG. 3 is a more detailed schematic diagram showing the cytometer of FIG. 2 with the cover not yet depressed.
Figure 4:
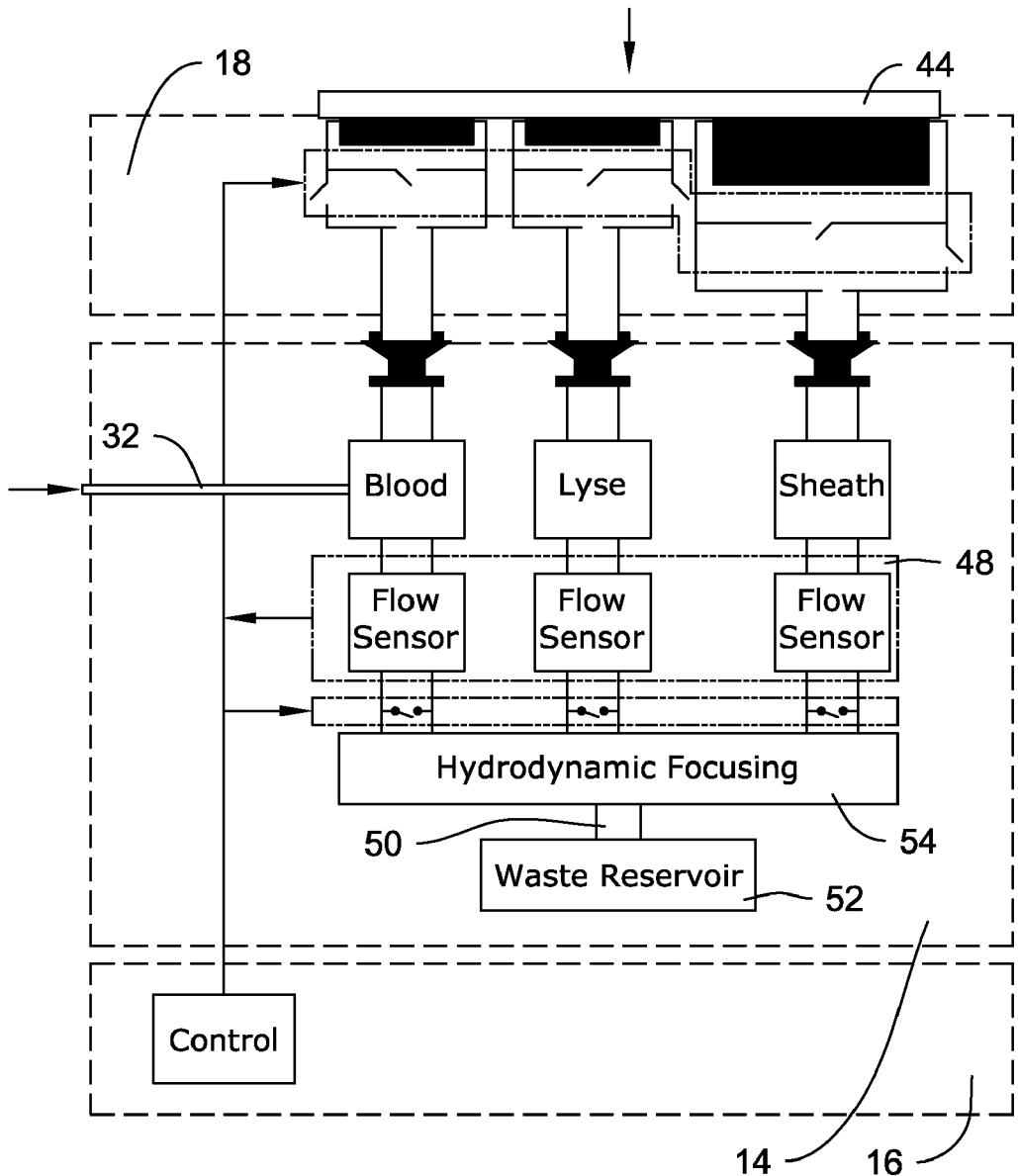
FIG. 4 is a more detailed schematic diagram showing the cytometer of FIG. 2 with the cover depressed.

FIG. 3 is a more detailed schematic diagram showing the cytometer of FIG. 2 with the cover 18 not yet depressed. FIG. 4 is a more detailed schematic diagram showing the cytometer of FIG. 2 with the cover depressed. The cover 18 is shown having a manual pressurizing element 44, pressure-chambers 46a, 46b and 46c, and control microvalves generally shown at 60. The light sources and detectors are not shown in these Figures.

There are three pressure chambers 46a, 46b and 46c, one for each fluid to be pressurized. In the illustrative example, pressure chamber 46a provides pressure to a blood sample reservoir 62, pressure chamber 46b provides pressure to a lyse reservoir 64, and pressure chamber 46c provides pressure to a sheath reservoir 66. The size and shape of each pressure chamber 46a, 46b and 46c may be tailored to provide the desired pressure characteristics to the corresponding fluid.

Pressure chamber 46a includes a first pressure chamber 70 and a second pressure chamber 72. A first valve 74 is provided between the first pressure chamber 70 and the second pressure chamber 72 for controllably releasing the pressure in the first pressure chamber 70 to a second pressure chamber 72. A second valve 76, in fluid communication with the second pressure chamber 72, controllably vents the pressure in the second pressure chamber 72. Each valve is preferably an array of electrostatically actuated microvalves that are individually addressable and controllable, as described in, for example, co-pending U.S. patent application Ser. No. 09/404,560, entitled "Addressable Valve Arrays for Proportional Pressure or Flow Control", and incorporated herein by reference. Pressure chambers 46b and 46c include similar valves to control the pressures applied to the lyse reservoir 64 and sheath reservoir 66, respectively. Alternatively, each valve may be an array of electrostatically actuated microvalves that are pulse modulated with a controllable duty cycle to achieve a controlled "effective" flow or leak rate.

The removable cartridge 14 has pressure receiving ports 34a, 34b, and 34c for receiving the controlled pressures from the cover 18. The controlled pressures are provided to the blood reservoir 62, lyse reservoir 64 and sheath reservoir 66, as shown. The lyse reservoir 64 and sheath reservoir 66 are preferably filled before the removable cartridge 14 is shipped for use, while the blood reservoir 62 is filled from sample collector port 32. A blood sample may be provided to the sample collector port 32, and through capillary action, the blood sample is sucked into the blood reservoir 62. Once the blood sample is in the blood reservoir 62, the cover 18 may be closed and the system may be pressurized.

A flow sensor is provided in-line with each fluid prior to hydrodynamic focusing. Each flow sensor 80, 100 and 102 measures the velocity of the corresponding fluid. The flow sensors are preferably thermal anemometer type flow sensors, and more preferably microbridge type flow sensor. Microbridge flow sensors are described in, for example, U.S. Pat. No. 4,478,076, U.S. Pat. No. 4,478,077, U.S. Pat. No. 4,501,144, U.S. Pat. No. 4,651,564, U.S. Pat. No. 4,683,159, and U.S. Pat. No. 5,050,429, all of which are incorporated herein by reference. An output signal from each flow sensor 80, 100 and 102 is provided to controller or processor 40.

The controller or processor 40 opens the first valve 74 when the velocity of the blood sample drops below a first predetermined value and opens the second valve 76 when the velocity of the blood sample increases above a second predetermined value. Valves 84, 86, 94 and 96 operate in a similar manner to control the velocities of the lyse and sheath fluids.

During operation, and to pressurize the system, the manual pressurizing element 44 is depressed. In the example shown, the manual pressurizing element 44 includes three plungers, with each plunger received within a corresponding one of the first pressure chambers. The plungers create a relatively high non-precision pressure in the first pressure chambers. Lower, controlled pressures are built in the secondary chambers by opening the first valves 70, 84 and 94, which produce a controllable leak into the secondary chambers. If too much pressure builds up in the secondary pressure chambers, the corresponding vent valves 76, 86 and 96 are opened to relieve the pressure.

When closing the cover 18, the normally open first valves 74, 84 and 94 are closed while the vent valves 76, 86 and 96 are open. When a predetermined pressure P is achieved in the first pressure chambers, the vent valves 76, 86 and 96 are closed, and the first valves 74, 84 and 94 are opened to build a lower pressure P' in the secondary pressure chambers. The controlled pressure in the secondary pressure chambers provide the necessary pressures to the fluidic circuit of the removable cartridge 14 to produce fluid flow for the blood, lyse and sheath. The velocity of the fluid flow is then measured by the downstream flow sensors 80, 100 and 102. Each flow sensor provides an output signal that is used by the controller or processor 40 to control the operation of the corresponding first valve and vent valve to provide a desired and constant flow rate for each fluid.

Downstream valves generally shown at 110 may also be provided. Controller or processor 40 may close downstream valves 110 until the system is pressurized. This may help prevent the blood, lyse and sheath from flowing into the fluid circuit before the circuit is pressurized. In another illustrative example of the invention, downstream valves 110 are opened by mechanical action when the cover is closed.

Figure 5:
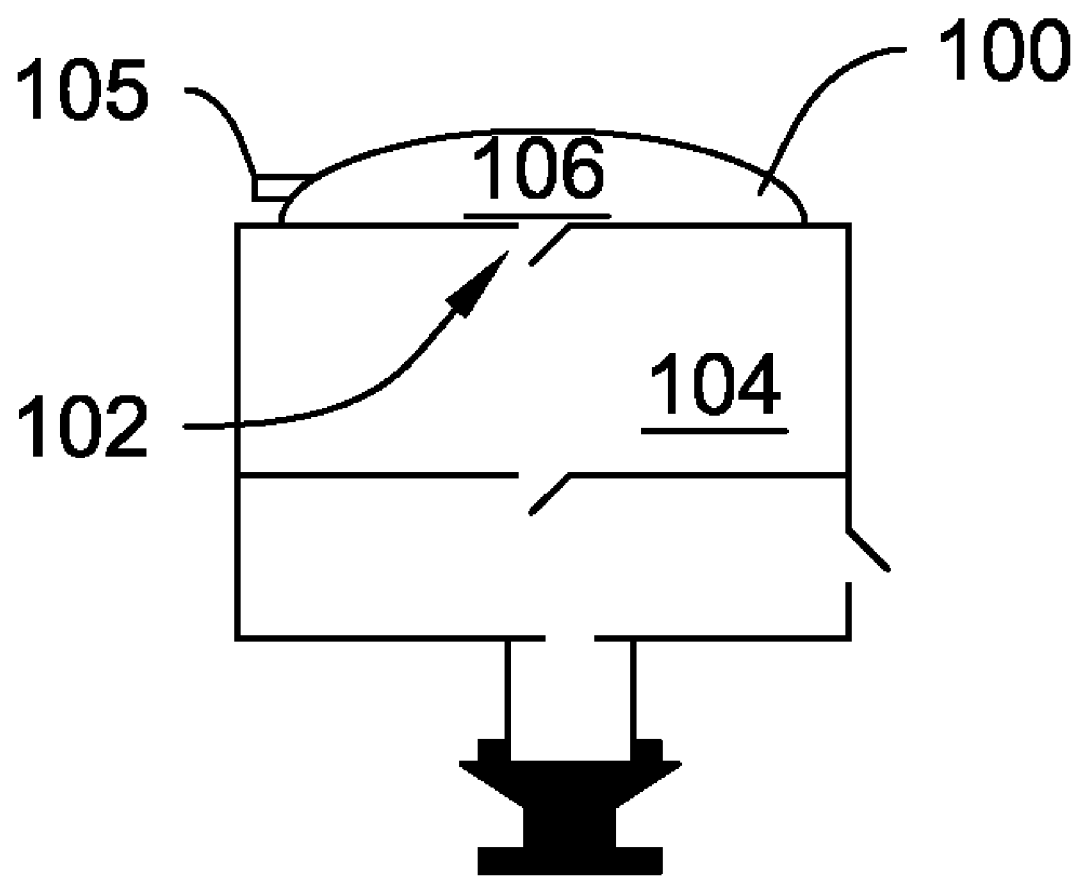
FIG. 5 is a schematic diagram showing an illustrative manual fluid driver having a bulb and check valve.

FIG. 5 is a schematic diagram showing an illustrative manual fluid driver having a bulb 100 and check valve 102. The check valve 102 is preferably a one way valve that allows air in but not out of the first pressure chamber 104. When the bulb 100 is depressed, the air in the interior 106 of the bulb 100 is forced through the check valve 102 and into the first pressure chamber 104. Preferably, another one-way vent valve 105 is provided that allows air in from the atmosphere but not out of the interior 106 of the bulb 100. Thus, when the bulb is released, the one-way vent valve 105 may allow replacement air to flow into bulb 100.

Rather than using a manually operated fluid driver, it is contemplated that any relatively small pressure source may be used including, for example, an electrostatically actuated meso-pump. One such meso-pump is described in, for example, U.S. Pat. No. 5,836,750 to Cabuz, which is incorporated herein by reference.

Figure 6:
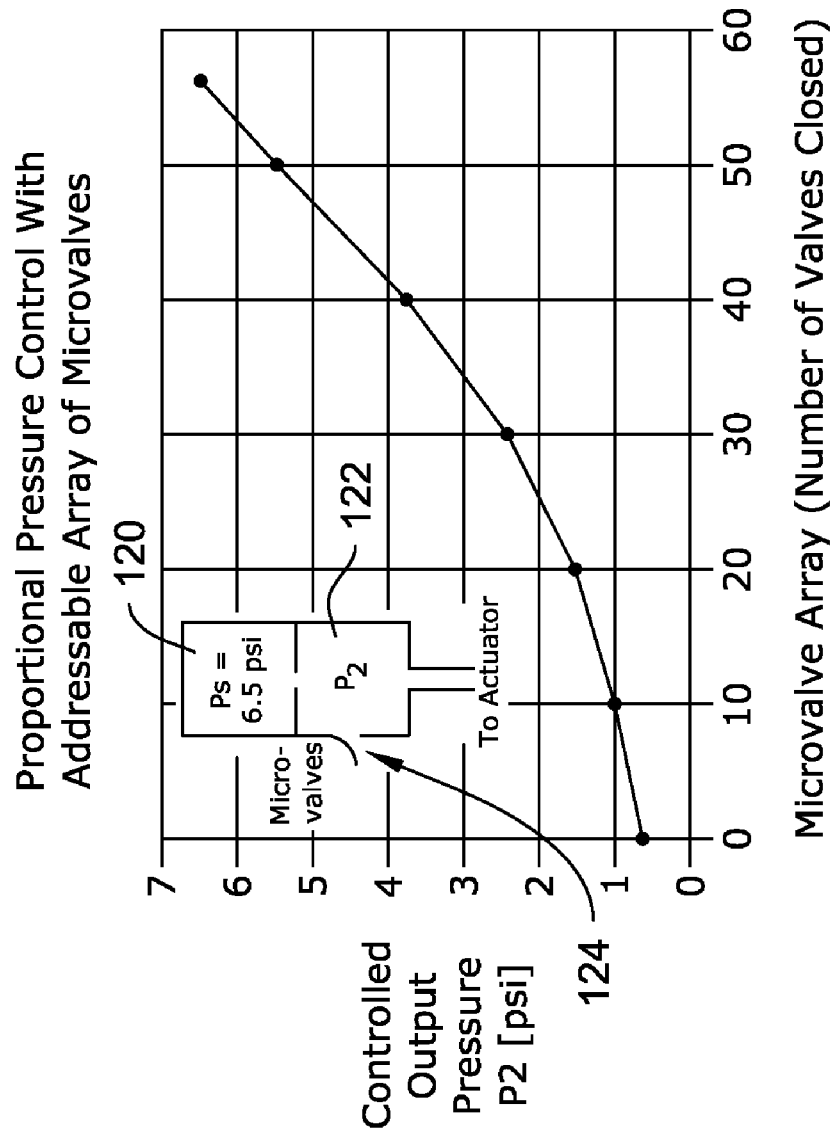
FIG. 6 is a graph showing proportional pressure control of an addressable array of microvalves.

FIG. 6 is a graph showing proportional pressure control produced by an 8×7 addressable array of microvalves. To create the graph shown in FIG. 6, 6.5 psi was applied to a first pressure chamber 120. A small opening was provided to a second pressure chamber 122. The microvalves are shown at 124, and vent the pressure in the second pressure chamber 122. By changing the number of addressable microvalves that are closed, the pressure in the second pressure chamber can be changed and controlled. In the graph shown, the pressure in the second pressure chamber 122 could be changed from about 0.6 psi, when zero of the 8×7 array of microvalves close, to about 6.5 psi, when all of the 8×7 array of microvalves are closed. These low power, micromachined silicon microvalves can be used for controlling pressures up to 10 psi and beyond.

Figure 7:
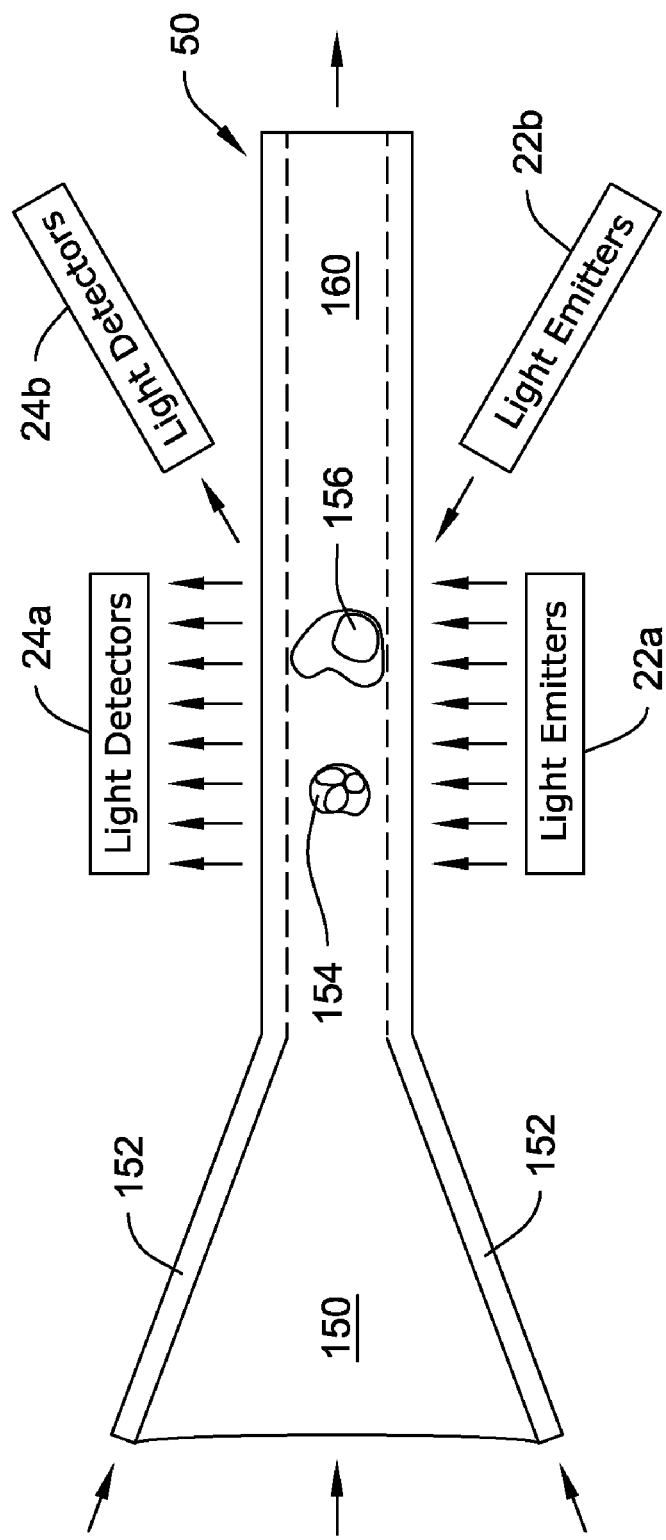
FIG. 7 is a schematic diagram showing the formation of a flow stream by the hydrodynamic focusing block 88 of FIG. 3.

FIG. 7 is a schematic diagram showing the formation of a flow stream and core by the hydrodynamic focusing block 88 of FIG. 3. The hydrodynamic focusing block 88 receives blood, lyse and sheath at controlled velocities from the fluid driver. The blood is mixed with the lyse, causing the red blood cells to be removed. The lysing solution may have a pH lower than that of the red blood cells. This is often referred to as red cell lysing or lyse-on-the-fly. The remaining white blood cells are provided down a central lumen 150, which is surrounded by sheath fluid to produce a flow stream 50. The flow stream 50 includes a core stream 160 surrounded by the sheath fluid 152. The dimensions of the channel are reduced as shown so that the white blood cells 154 and 156 are in single file. The velocity of the sheath fluid is preferably about 9 times that of the core stream 160. However, the velocity of the sheath fluid and core stream 160 remains sufficiently low to maintain laminar flow in the flow channel.

Light emitters 22a and 22b, and associated optics are preferably provided adjacent one side of the flow stream 50. Light detectors 24a and 24b, and associated optics are provided on another side of the flow stream 50 for receiving the light from the light emitters 22a and light from fluorescing particles via the flow stream 50. The output signals from the light detectors 24a and 24b are provided to controller or processor 40, wherein they are analyzed to identify and/or count selected white blood cells in the core stream 160.

Figure 8:
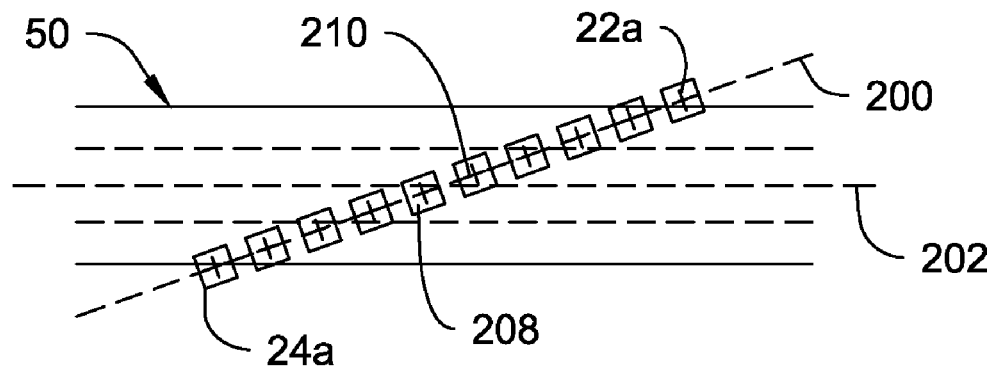
FIG. 8 is a schematic diagram showing an array of light sources and an array of light detectors for analysis of the core stream 160 of FIG. 7.

FIG. 8 is a schematic diagram showing an array 22a of light sources and an array 24b of light detectors for analysis of the core stream 160 via scattering of FIG. 7. The light sources are shown as "+" signs and the detectors are shown at boxes. In the example shown, the array of light sources is provided adjacent one side of the flow stream 50, and the array of light detectors is provided adjacent the opposite side of the flow stream. Each of the light detectors is preferably aligned with a corresponding one of the light sources. The array of light sources and the array of light detectors are shown arranged along a light source axis 200 that is slightly rotated relative to the axis 202 of the flow stream 50.

The array 22a of light sources is preferably an array of lasers such as vertical cavity surface emitting lasers (VCSELs) fabricated on a common substrate. Because of their vertical emission, VCSELs are ideally suited for packaging in compact instruments such as a miniaturized portable cytometer. Such cytometer may be wearable on a person's body. Preferably, the VCSELs are "red" VCSELs that operate at wavelengths that are less than the conventional 850 nm, and more preferably in the 670 nm to 780 nm range. Red VCSELs may have a wavelength, power and polarization characteristic that is ideally suited for scatter measurements.

Some prior art cytometer bench models use a single 9 mW edge-emitting laser with a wavelength of 650 nm. The beam is focused to a 10×100 micron elongated shape to cover the uncertainty in particle position due to misalignment and width of the core stream. In contrast, the output power of the red VCSELs of the present invention, operating at 670 nm, is typically around 1 mW for a 10×10 micron emitter and 100-micron spacing. Thus, the total intensity of the light from a linear array of ten red VCSELs may be essentially the same as that of some prior art bench models.

Using a linear array of lasers oriented at an angle with respect to the flow axis 202 offers a number of important advantages over the single light source configuration of the prior art. For example, a linear array of lasers may be used to determining the lateral alignment of the path of the particles in the core steam. One source of uncertainty in the alignment of the particle stream is the width of the core flow, which leads to statistical fluctuations in the particle path position. These fluctuations can be determined from analysis of the detector data and can be used by the controller or processor 40 to adjust the valves of the fluid driver in order to change the relative pressures that are applied to the sample fluid and the supporting fluids to change the alignment of the selected particles in the flow stream.

To determine the lateral alignment of the cells in the fluid stream 50, the cells pass through several focused spots produced by the linear array of VCSELs. The cells produce a drop in signal in the corresponding in-line reference detectors. The relative strengths of the signals are used by the controller or processor 40 to determine the center of the particle path and a measure of the particle width.

Figure 9:
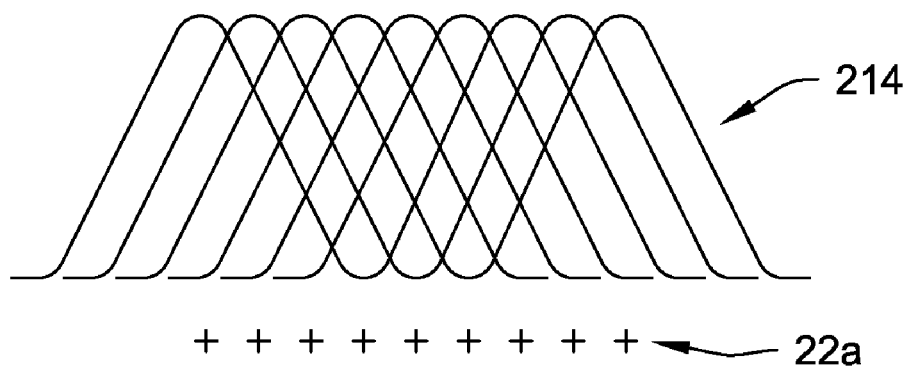
FIG. 9 is a graph showing the light intensity produced along the light source axis of FIG. 8.

For determining particle path and size, the lasers 22a are preferably focused to a series of Gaussian spots 214 (intensity on the order of 1000 W/cm$^2$) in the plane of the core flow. The spots 214 are preferably about the same size as a white blood cell (10-12 um). Illustrative Gaussian spots 214 are shown in FIG. 9. Arrays 24a of detectors and their focusing optics are provided on the opposite side of the fluid stream 50. Lenses with fairly large F-numbers are used to provide a working space of several hundred microns for the cytometer section of the removable cartridge.

Another advantage of using a linear array 22a of lasers rather than a single laser configuration is that the velocity of each cell may be determined. Particle velocity can be an important parameter in estimating the particle size from light scatter signals. In conventional cytometry, the particle velocity is extrapolated from the pump flow rates. A limitation of this approach is that the pumps must be very precise, the tolerance of the cytometer flow chambers must be tightly controlled, no fluid failures such as leaks can occur, and no obstructions such as microbubbles can be introduced to disturb the flow or core formation.

To determine the velocity of each cell, the system may measure the time required for each cell to pass between two adjacent or successive spots. For example, and with reference to FIG. 8, a cell may pass detector 208 and then detector 210. By measuring the time required for the cell to travel from detector 208 to detector 210, and by knowing the distance from detector 208 to detector 210, the controller or processor 40 can calculate the velocity of the cell. This would be an approximate velocity measurement. This is often referred to as a time-of-flight measurement. Once the velocity is known, the time of travel through the spot on which the particle is centered (a few microseconds) may provide a measure of particle length and size.

It is contemplated that the particle velocity can also be used to help control the fluid driver. To reduce the size, cost and complexity of the present invention, the replaceable cartridge of FIG. 1 may be manufactured from a plastic laminate or molded parts. While such manufacturing techniques may provide inexpensive parts, they are typically less dimensionally precise and repeatable, with asymmetrical dimensions and wider tolerance cross-sections. These wider tolerances may produce variations in particle velocity, particularly from cartridge to cartridge. To help compensate for these wider tolerances, the time-of-flight measurement discussed above can be used by the controller or processor 40 to adjust the controlled pressures applied to the blood, lyse and sheath fluid streams such that the particles in the core stream have a relatively constant velocity.

To further evaluate the cell size, it is contemplated that laser beams may be focused both along the cell path and across the cell path. Additionally, multiple samples across the cell may be analyzed for texture features, to correlate morphological features to other cell types. This may provide multiple parameters about cell size that may help separate cell types from one another.

Another advantage of using a linear array 22a of lasers rather than a single layer configuration is that a relatively constant light illumination may be provided across the flow channel. This is accomplished by overlapping the Gaussian beams 214 from adjacent VCSELs 22a, as shown in FIG. 9. In prior art single laser systems, the light illumination across the flow channel typically varies across the channel. Thus, if a particle is not in the center of the flow channel, the accuracy of subsequent measurements may be diminished.

Figure 10:
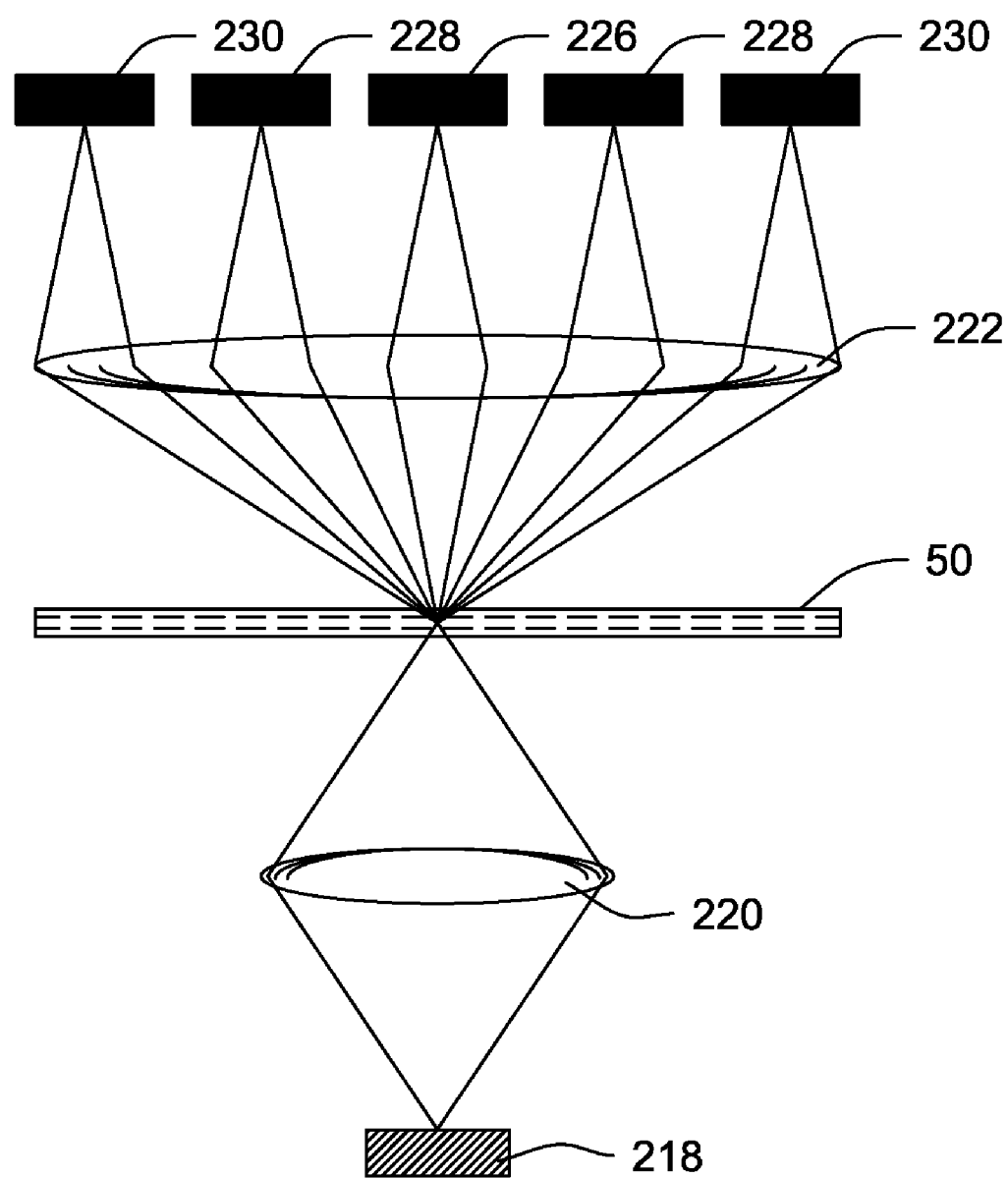
FIG. 10 is a schematic diagram showing an illustrative light source and detector pair of FIG. 8.

To perform the above described measurements, each detector 24a in FIG. 8 may be a single in-line detector. To measure FALS and SALS scatter, however, each detector 24a may further include two annular detectors disposed around the in-line detector, as shown in FIG. 10. Referring to FIG. 10, a VCSEL 218 is shown providing light in an upward direction. The light is provided through a lens 220, which focuses the light to a Gaussian spot in the plane of the core flow. Lens 220 may be a microlens or the like, which is either separate from or integrated with the VCSEL 218. The light passes through the core flow, and is received by another lens 222, such as a diffractive optical element. Lens 222 provides the light to in-line detector 226 and annular detectors 228 and 230. The in-line detector 226 detects the light that is not significantly scattered by the particles in the core stream. Annular detector 228 detects the forward scatter (FALS) light, and annular detector 230 detects the small angle scatter (SALS) light.

Figure 11:
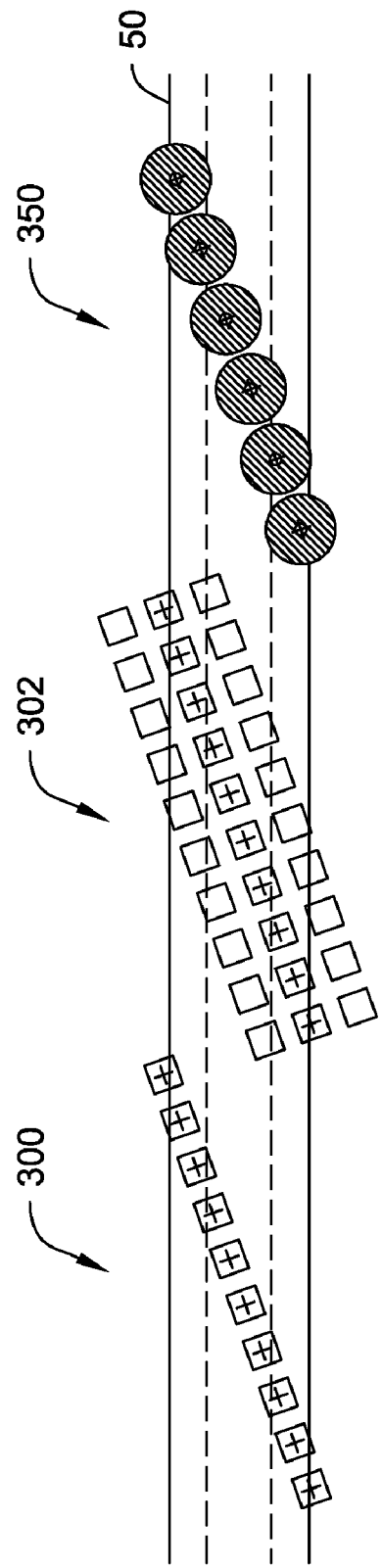
FIG. 11 is a schematic diagram showing three separate arrays of light sources and detectors, each positioned along a different light source axis that is slightly rotated relative to the central flow axis of the flow stream of FIG. 7.

FIG. 11 shows another illustrative example of the present invention that includes three separate arrays of light sources and light detectors. Each array of light sources and light detectors are positioned along a different light source axis that is slightly rotated relative to the central flow axis of the flow stream. By using three arrays, the optics associated with each array may be optimized for a particular application or function. For detecting small angle scattering (SALS), laser light that is well-focused on the plane of the core flow is desirable. For detecting forward scattering (FALS), collimated light is desirable.

Referring specifically to FIG. 11, a first array of light sources and light detectors is shown at 300. The light sources and light detectors are arranged in a linear array along a first light source axis. The first light source axis is rotated relative to the flow axis of the flow stream. The light sources and light detectors may be similar to that described above with respect to FIG. 8, and preferably are used to measure, for example, the lateral alignment of the cells in the flow stream, the particle size, and the velocity of the particles.

FIG. 12 is a schematic diagram showing an illustrative light source and detector pair of the first array 300 shown in FIG. 11. A VCSEL 302 is shown providing light in an upward direction. The light is provided through a lens 304, which focuses the light to a Gaussian spot in the plane of the core flow. The light passes through the core flow, and is received by another lens 306. Lens 306 provides the light to in-line detector 308. The in-line detector 308 detects the light that is not significantly scattered by the particles in the core stream.

A second array of light sources and light detectors is shown at 310. The light sources are arranged in a linear array along a second light source axis that is rotated relative to the flow axis of the flow stream. The light detectors include three linear arrays of light detectors. One array of light detectors is positioned in line with the linear array of light sources. The other two linear arrays of light detectors are placed on either side of the in-line array of light detectors, and are used for measuring the small angle scattering (SALS) produced by selected particles in the flow stream.

FIG. 13 is a schematic diagram showing an illustrative light source and corresponding detectors of the second array shown in FIG. 11. A VCSEL 320 is shown providing light in an upward direction. The light is provided through a lens 322, which focuses the light to a Gaussian spot in the plane of the core flow. The light passes through the core flow, and is received by another lens 324, such as a diffractive optical element (DOE) 324. Lens 324 provides the light to the in-line detector 326 and the two corresponding light detectors 328 and 330 placed on either side of the in-line light detector 326.

The in-line detector 326 may be used to detect the light that is not significantly scattered by the particles in the core stream. Thus, the in-line linear array of light detectors of the second array 302 may be used to provide the same measurements as the in-line array of detectors of the first array 300. The measurements of both in-line arrays of detectors may be compared or combined to provide a more accurate result. Alternatively, or in addition, the in-line detectors of the second array 302 may be used as a redundant set of detectors to improve the reliability of the cytometer.

It is contemplated that the in-line detectors of the second array 302 may also be used in conjunction with the in-line detectors of the first array 300 to more accurately determine the time-of-flight or velocity of the particles in the flow stream. The measurement may be more accurate because the distance between detectors may be greater. As indicated above, by knowing the velocity of the particles, small variations in the flow rate caused by the fluid driver can be minimized or removed by the controller.

Light detectors 328 and 330 of FIG. 13 are used to measure the small angle scattering (SALS) produced by selected particles in the flow stream. The light detectors 328 and 330 are therefore preferably spaced sufficiently from the in-line detector 326 to intercept the small angle scattering (SALS) produced by selected particles in the flow stream.

Referring back to FIG. 11, a third array of light sources and light detectors 350 is preferably provided to measure the forward angle scattering (FALS) produced by selected particles in the flow stream. The light sources are arranged in a linear array along a third light source axis that is rotated relative to the flow axis of the flow stream. Each light source preferably has a corresponding light detector, and each light detector is preferably annular shaped with a non-sensitive region or a separate in-line detector in the middle. The annular shaped light detectors are preferably sized to intercept and detect the forward angle scattering (FALS) produced by selected particles in the flow stream.

Figure 14:
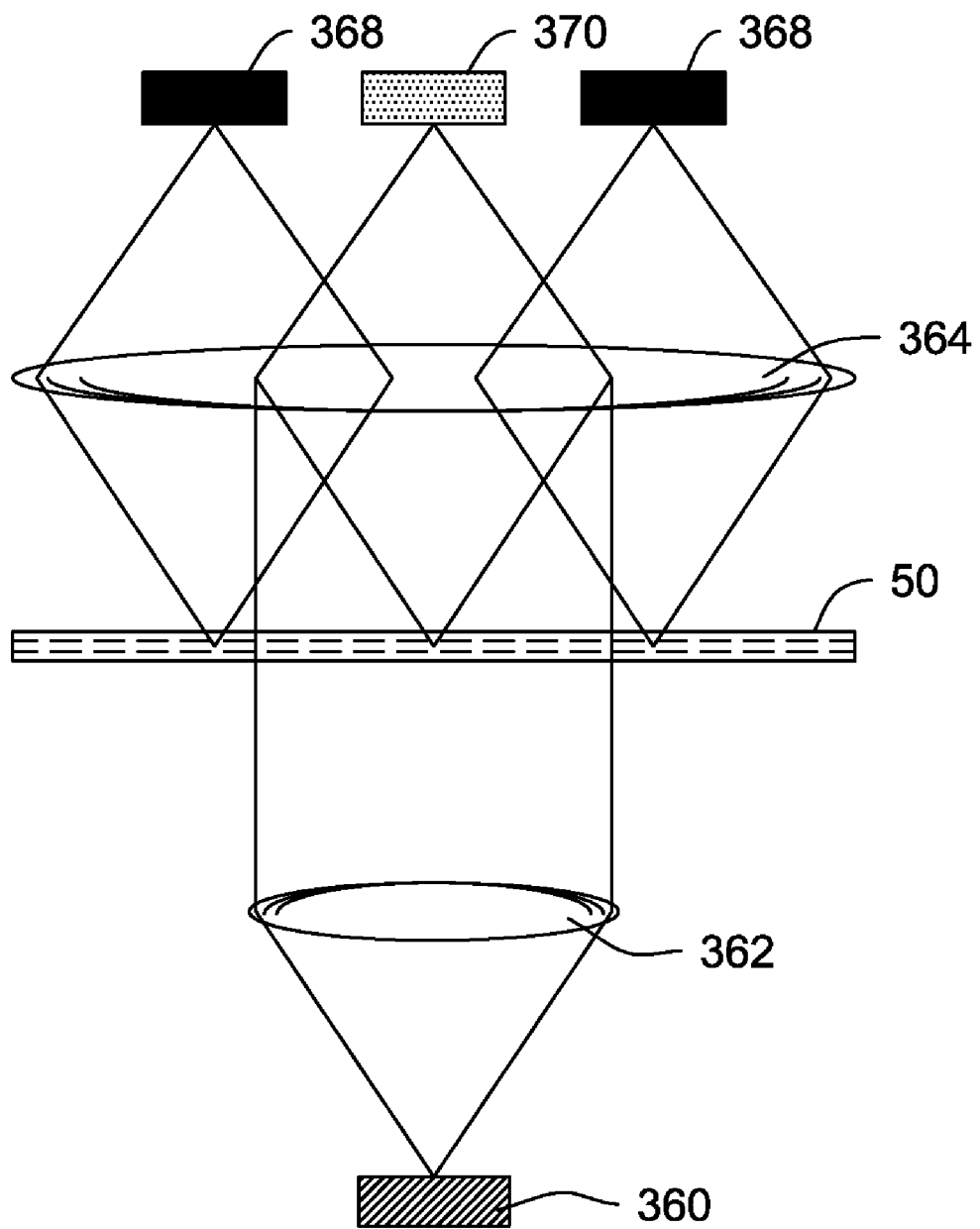
FIG. 14 is a schematic diagram showing an illustrative light source and detector pair of the third array shown in FIG. 11.

FIG. 14 is a schematic diagram showing an illustrative light source and detector pair of the third array of light sources and light detectors 350 shown in FIG. 11. A VCSEL 360 is shown providing light in an upward direction. The light is provided through a lens 362 such as a collimating lens, which provides substantially collimated light to the core flow. As indicated above, collimated light is desirable for detecting forward scattering (FALS) light. The light passes through the core flow, and is received by another lens 364. Lens 364 provides the received light to the annular shaped detector 368.

The annular shaped detector 368 is preferably sized to intercept and detect the forward angle scattering (FALS) produced by selected particles in the flow stream. A non-sensitive region or a separate in-line detector 370 may be provided in the middle of the annular shaped detector 368. If a separate in-line detector 370 is provided, it can be used to provide the same measurement as the in-line detectors of the first array 300 and/or second array 302. When so provided, the measurements from all three in-line arrays of detectors of first array 300, second array 302 and third array 350 may be compared or combined to provide an even more accurate result. The in-line detectors of the third array 302 may also be used as another level or redundancy to improve the reliability of the cytometer.

It is contemplated that the in-line detectors of the third array 350 may also be used in conjunction with the in-line detectors if the first array 300 and/or second array 302 to more accurately determine the time-of-flight or velocity of the particles in the flow stream. The measurement may be more accurate because the distance between detectors may be greater. As indicated above, by knowing the velocity of the particles, small variations in the flow rate caused by the fluid driver can be minimized or removed by the controller.

By using three separate arrays of light sources and detectors, the optics associated with each array can be optimized for the desired application. As can be seen, the optics associated with the first array 300 are designed to provide well-focused laser light on the plane of the core flow. This helps provide resolution to the alignment, size and particle velocity measurements performed by the first array 300. Likewise, the optics associated with the second array 302 are designed to provide well-focused laser light on the plane of the core flow. Well focused light is desirable when measuring the small angle scattering (SALS) produced by selected particles in the flow stream. Finally, the optics associated with the third array 350 are designed to provide collimated light to the core flow. As indicated above, collimated light is desirable when measuring forward angle scattering (FALS) produced by selected particles in the flow stream.

Figure 15:
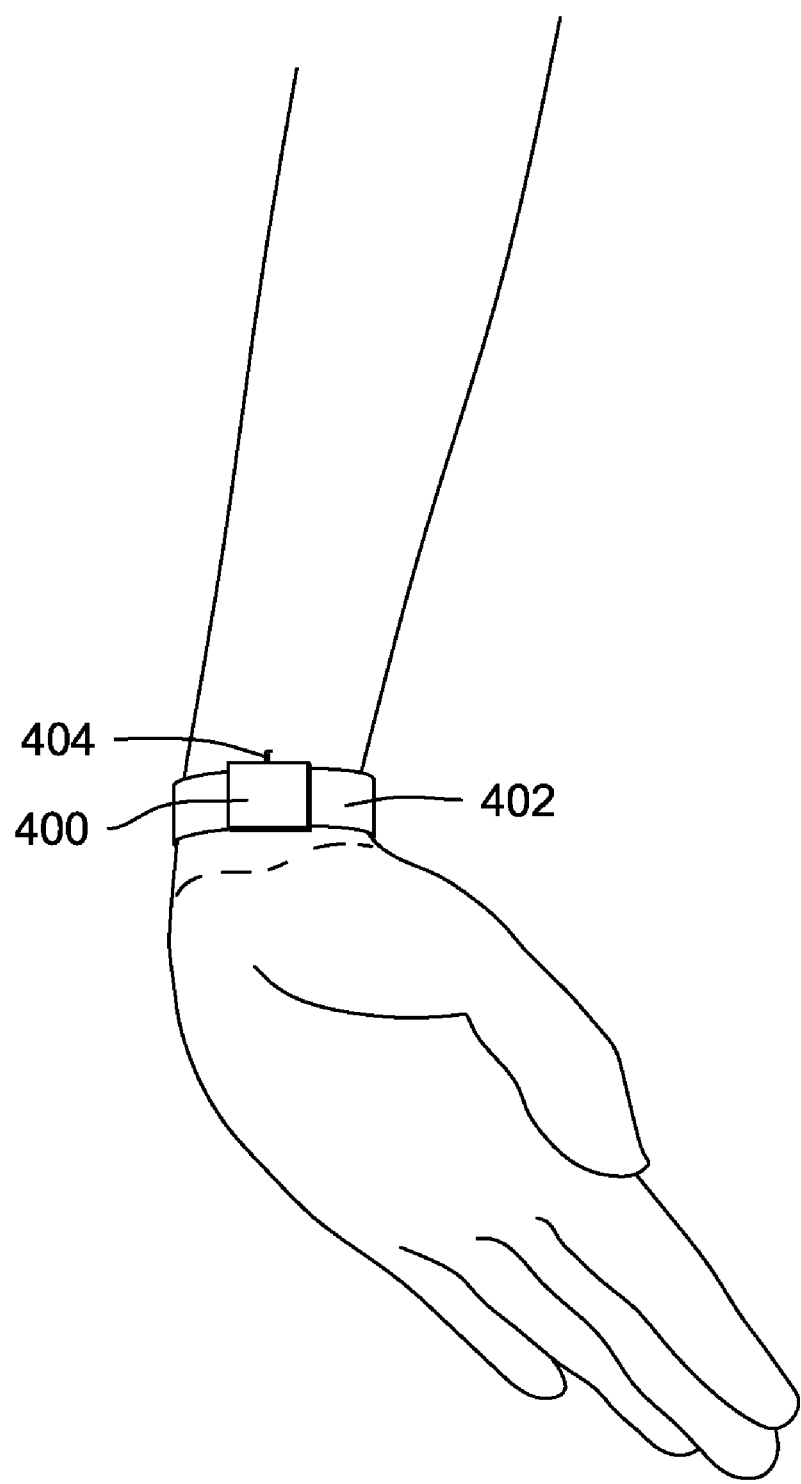
FIG. 15 is a perspective view of an illustrative example of the miniaturized portable cytometer adapted to be worn around the wrist.

FIG. 15 is a perspective view of an illustrative example of the miniaturized portable cytometer of the present invention adapted to be worn around the wrist. This cytometer 400 may be similar to that shown in FIG. 1. A band 402 secures cytometer 400 to the wrist of a user.

As indicated above, the user may obtain a removable cartridge and provide a blood sample to the sample collector port 32 (see FIG. 1) of the removable cartridge. The blood sample may be collected by, for example, a finger prick. The user may then insert the removable cartridge into the housing, and manually pressurize the system. The miniaturized portable cytometer may then provide a reading that indicates if the user should seek medical treatment. The reading may be a visual reading, an audible sound or any other suitable indicator.

Rather than obtaining the blood sample by a finger prick or the like, it is contemplated that a catheter 404 or the like may be inserted into a vein of the user and attached to the sample collector port 32. This may allow the system to automatically collect a blood sample from the user whenever a reading is desired. Alternatively, it is contemplated that the miniaturized portable cytometer may be implanted in the user, with the sample collector port 32 connected to a suitable blood supply.

Figures 16, 17:
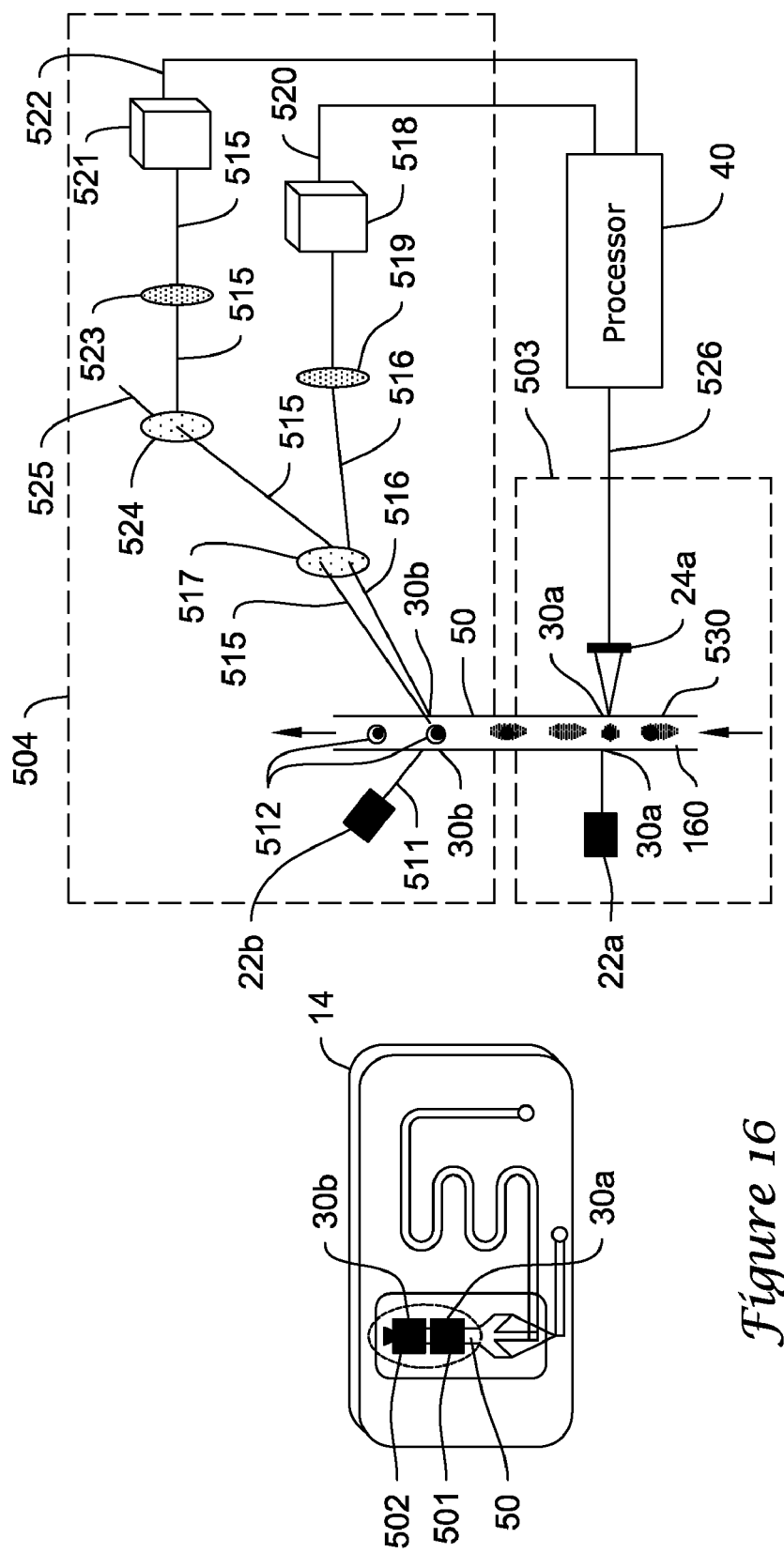
FIG. 16 is an illustration of a miniaturized portable cytometer cartridge incorporating the scattering and fluorescence optical subsystems.
FIG. 17 shows the layout of the scattering and fluorescence detection systems.

FIG. 16 shows a cytometer cartridge 500 showing a scattering optical subsystem 501 and fluorescent optical subsystem 502. Optical subsystem 501 includes windows or openings 30a on each side of flow channel 530 and optical subsystem 502 includes windows or openings 30b. In each subsystem, there is a window or opening on each side of flow channel 530. The openings may have optical inserts or lenses. This cytometer may be implemented for wearing, attachment on, or insertion in a person's body FIG. 17 shows systems 503 and 504 which incorporate optical subsystems 501 and 502, respectively. System 503 also includes VCSEL array 22a and detector array 24a for scattering measurements of particles, such as white blood cells, in core stream 160. This system is may be used for the counting and classification of lymphocytes and neutrophils. Self-alignment is may be enabled by a red VCSEL-array based optical subsystem. Illustrative examples of scattering system 503 are described above.

System 504 is a fluorescent exciting and detection mechanism which may be used for identifying and counting specific subclasses of white blood cells and blood-based proteins. The detection of subclasses of white blood cells is enabled by the availability of suitable antibodies, many of which are commercially available in a fluorescently conjugated form. FIG. 18 shows an outline sketch of blood composition and the cells that may be subject to counting and identification by fluorescent system 504. The red blood cells are removed form the sample to be looked with the cytometer by lysing as noted above. The platelets are kept as the small size does not affect the results of the cytometer when checking the white blood cells. For an illustrative example, the CD4-positive T-cells 505, shown in the structure of FIG. 18 have proportions and counts in blood that may be very important in following a clinical course of an HIV infection. An antibody with a marker added that associates with CD4 may be mixed in the sample of blood to get a resultant "Y"-looking structure of the antibody (AB) 506 and its marker (M) 507, attached to CD4 cell 505, as shown in FIG. 19a. Light source 22b may emit light which may be absorbed by marker 507. In response, marker 507 fluoresces and emits light of a particular wavelength which may be detected to identify CD4 cell 505.

Checking blood for anthrax may be another application of the present cytometer. Antibodies 508 for the anthrax-causing bacteria 509 may be mixed with the blood sample. The antibodies may associate with bacteria 509. The antibodies may have markers 510 that fluoresce upon impingement of light. The "Y" structure of antibody 508 is shown in FIG. 19b. Markers 510 emit a light of a particular bandwidth which may be different from the bandwidth of marker 507 of antibody 506 for CD4 cell 505. So the anthrax problem may be identified separately from the HIV problem in the same blood sample test by the fluorescent emissions having different wavelengths, colors or signatures. The number of different problems being detected at the same time in the same blood sample may be many more than two.

For another illustrative example, Neupogen$^R$ (a type of protein) has been regarded as used to provide neutrophil counts in cancer patients undergoing myelosuppressive chemotherapy. While doing this therapy, there may a need to accurately monitor the white blood cell counts (specifically neutrophils, monocytes and platelet counts during the Neupogen$^R$ therapy period). The present cytometer may be used by untrained personnel to monitor such chemotherapy patients in their homes.

The present miniaturized portable cytometer may be use in biowarfare. It may be used for quantitative detection and identification of biowarfare agents. This detection and identification may be based antibody-antigen type immunoassay that may be implemented with fluorescent measurements. The environment, water and food may be monitored for any possible presence of biological agents. It would involve sample collection and preparation appropriated for the present cytometer. Other applications of the cytometer may include high throughput analysis (using the fluorescent detection features) and sequencing of DNA and RNA, studying the response of cell to potential drugs, immunophenotyping of leukemia and lymphomas and monitoring residual disease in cancer patients, and cell sorting and cell isolation, including high-speed separation of rare event populations. Note that the above-mentioned applications, and other applications and uses may be accomplished with the single, portable, miniaturized, integrated scattering and multi-color fluorescent, low-power, low-cost cytometry instrument having a compact precision fluid driving system, not requiring operator intervention or adjustment during the analytical phase, not requiring trained personnel to operate the instrument, and using sanitary, disposable plastic- or other material-based microfluidic cartridges 14 having integrated optics and internal blood sample processing, among other features.

System 504 of FIG. 17 has a laser light source 22b positioned to direct light 511 at particles 512 flowing single file through flow channel 530. For illustrative purposes, particles 512 may include structures 513 and 514 of FIGS. 19a and 19b, respectively. Light 511 may be from a red or a blue laser source, such as a light emitting diode (LED), which may have a bandwidth of, for example, 650 to 700 nanometers or 380 to 420 nanometers, respectively. Other types of sources having appropriate wavelengths may be used for light 511. As light 511 impinges fluorescent markers 507 and 510, these markers fluoresce and emit light 515 and 516, respectively. Since the markers are different from each other, light 515 and light 516 have different wavelengths. Thus, structures 513 and 514 not only may be identifiable by the wavelengths of their emitted light but can be differentiated form each other in the same sample, blood or otherwise. Light 515 and 516 may go to a dichroic beam splitter 517 which separates the two beams by directing each of them in different directions. Beam 516 may go to a fluorescence photo detector 518 for detection and conversion of light 516 into an electrical signal 520 to processor 40. Beam 515 may go to a fluorescence photo detector 521 for detection and conversion of light 515 into an electrical signal 522 to processor 40. Band pass filter 519, which is in the path of beam 516, may filter out light 511 from light source 22b that managed to be present in beam 516. Band pass filter 523 may serve the same purpose for beam 515 as filter 519 for beam 515. A mirror 524 may be used to redirect beam 515 for purposes of detector 521 location for the possibility of more compact packaging of detection system 504 or for other reasons. Mirror 524 may on the other hand be another dichroic beam splitter for splitting out light 525 of a wavelength different from that of beams 515 and 516. More splitters might be used in a cascade-like or other structure to split out light of still other frequencies. Also going to processor 40 is a signal from detector array 24a of scattering detection system 503.

Splitter 517 may be replaced with other mechanisms for separating out the light of various wavelengths or selecting certain wavelengths. They may include notch and step function filters of various kinds, tunable diffraction gratings, thin film dielectric stacks, mirror beam splitters, photonic bandgap filters, photonic crystals, tunable band pass filters, etalon comb and other structures, wafers having light guides with structural or other filtering, silicon or glass wafers having a waveguide and perforations of a specific size and pitch for absorbing/filtering, and so on.

Figure 20:
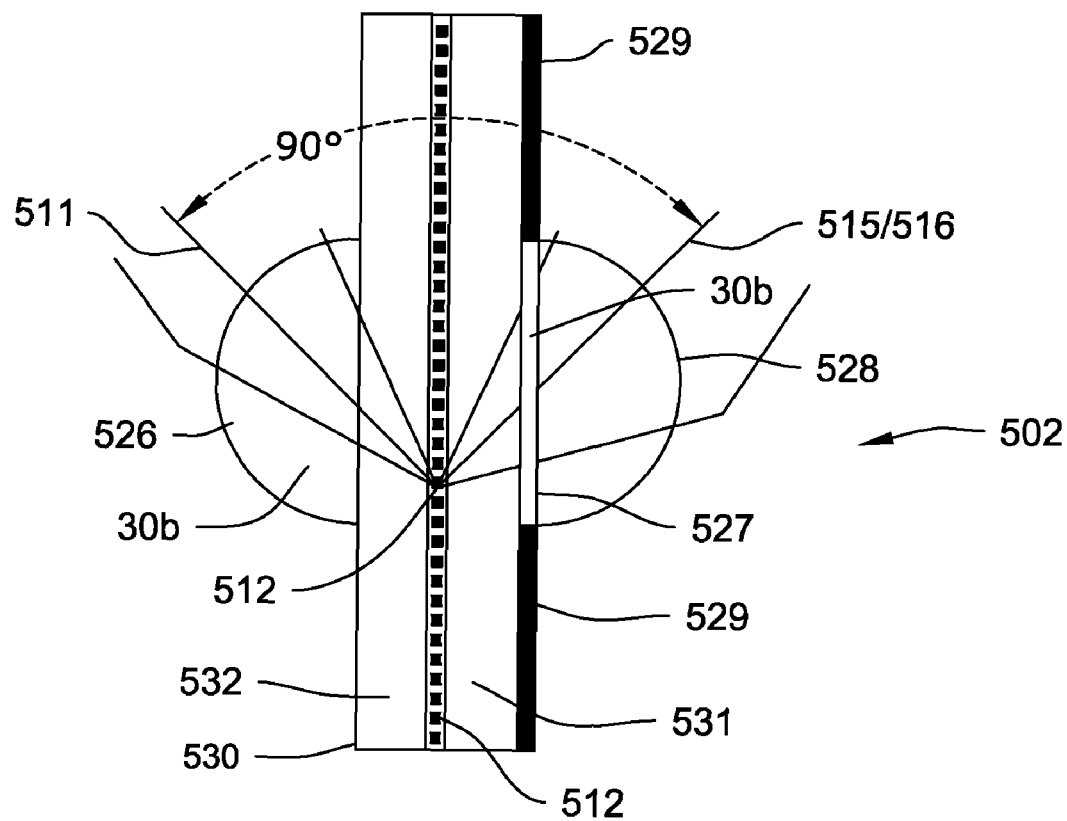
FIG. 20 shows the interaction of the light and optics for the fluorescence system.

FIG. 20 shows the structure of the fluorescence optical subsystem 502. A beam 511 may be emitted by light source 22b and focused onto a particle 512 by a microlens 526 through window 30b. Light beam 511 may or may not be collimated. Particle 512 may have a marker that fluoresces and emits a light beam 515, 516 through window 30b, a thin film coating filter 527 and a microlens 528, respectively. Filter 527 may filter out light 511 from light source 22b. Filter 527 may be a dielectric stack situated under lens 528 and be a notch or step function filter to block source 22b light 511. Lens 528 may focus fluorescent light emitted from the marker into a beam 515/516 which may go on to a beam splitter such as splitter 517. Beam 515/516 may or may not be collimated. An opaque or absorptive layer 529 is formed around or before and after window 30b or lens 528 on a glass, quartz or plastic (laminated or not) substrate 531 of flow channel 530. Layer 529 may block any light 511 emanating from light source 22b from exiting out with fluorescent light 515/516. Layer or blocking filter 529 may a thin film that is black or opaque to the wavebands desired to be blocked. Filter 529 could be a notch or step function filter. The other glass, quartz or plastic (laminated or not) substrate 532 forms flow channel 530 for the core flow of particles 512. The material of substrates 531 and 532, windows 30b and lens 526 and 528 should not contain ingredients that may fluoresce. In one illustrative example, the direction of light 511 from source 22b may be about 90 degrees relative to the direction of fluorescent light 515/516 emitted from particle 512. This angle between source light 511 and emitted fluorescent light 515/516 may effectively reduce or eliminate source light emanating out with fluorescent light 515/516. The angle of the direction of light 511 from source 22b in the example may be about 45 degrees relative to the direction of the longitudinal dimension flow channel 530 or the direction of the core flow of particles 512. However, in some applications, the angle between the directions of light 511 and light 515/516 may be between 0 and 120 degrees.

Figure 21A:
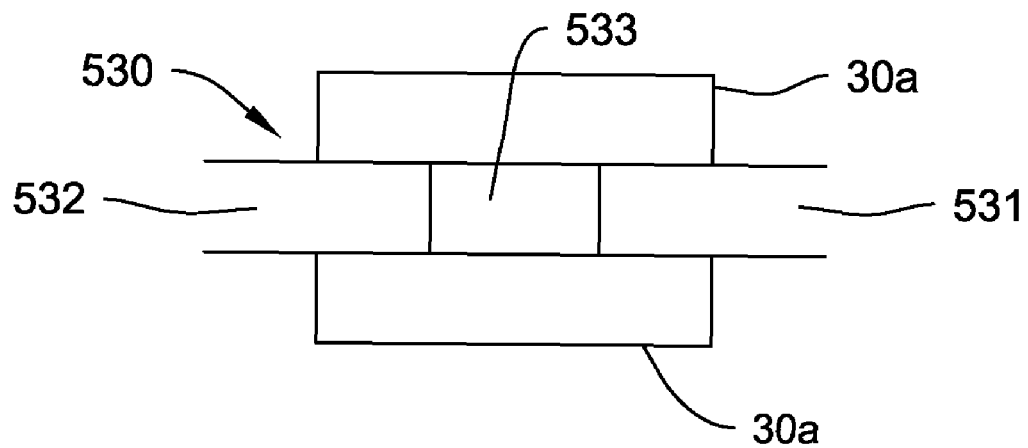
FIGS. 21a, 21b, 21c, 21d and 21e show the optical structure relative to the flow channel for the scattering and fluorescence systems, respectively.
Figure 21B:
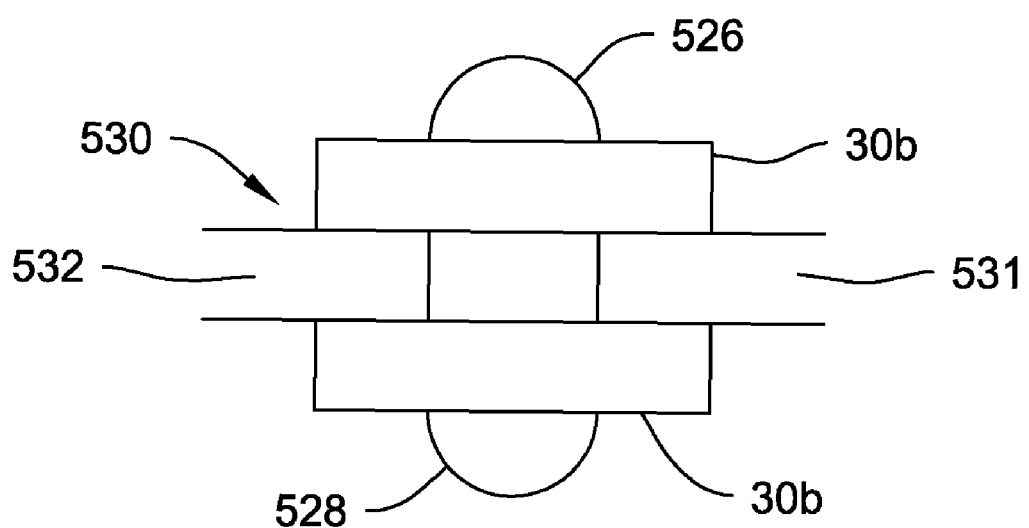

FIG. 21a shows an end view of flow channel 530 for scattering optical subsystem 501 and FIG. 21b shows an end view of flow channel 530 for fluorescence optical subsystem 502.

The thicknesses of substrates 531 and 532 are about 100 to 200 microns. The thicknesses of windows 30a and 30b are about 25 to 30 microns. Microlenses 526 and 528 may be diffractive or refractive, plastic or glass and be aspheric lenses about 500 microns in diameter. Channel 533 may be laser cut.

Figure 21C:
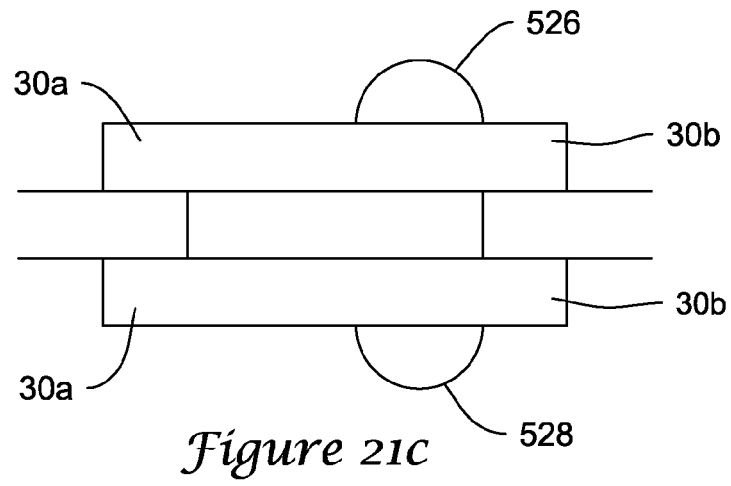
Figure 21D:
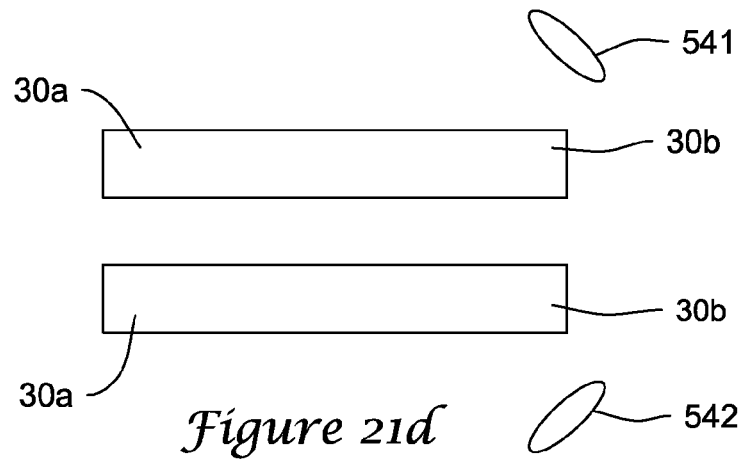
Figure 21E:
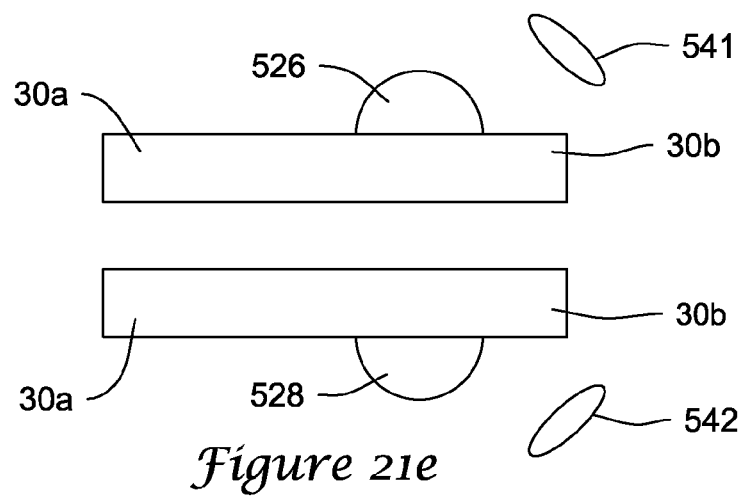

FIGS. 21c, 21d and 21e are variations of FIGS. 21a and 21b. FIG. 21c shows a flow channel having windows or openings 30a and 30b. Openings or windows 30a and 30b may be one window on each side of the flow channel, respectively. The openings may have optical inserts or lenses in them. Micro lenses 526 and 528 or other types of lenses may be formed on, attached to, inserted in, situated on or formed as an integral portion of openings or windows 30b and 30a which may be one piece on each side of the channel. FIG. 21d illustrates windows 30a and 30b without micro lenses attached or formed on them, but with lenses 541 and 542 situated at a certain and appropriate distance from them. FIG. 21e shows a window configuration with both micro lenses 526 and 528 along with detached lenses 541 and 542, respectively.

Figure 22:
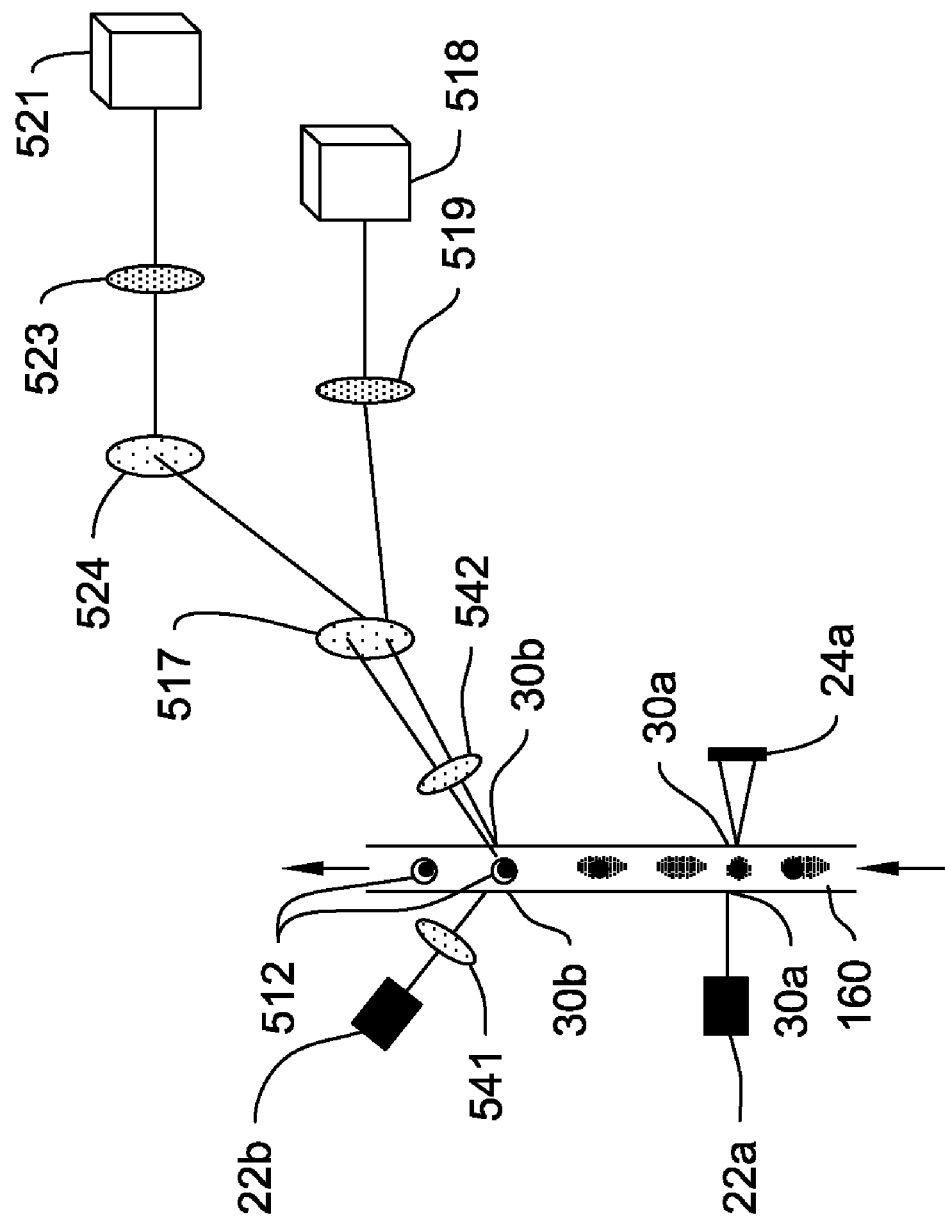
FIG. 22 shows a layout of the scattering and fluorescence detection systems having discrete lenses apart of the flow channel.

FIG. 22 shows a diagram of cytometer configuration of FIG. 17, but with the placement of lenses 541 and 542. As noted above, windows and openings 30b may or may not have micro lenses in addition to lenses 541 and 542.

Figure 23:
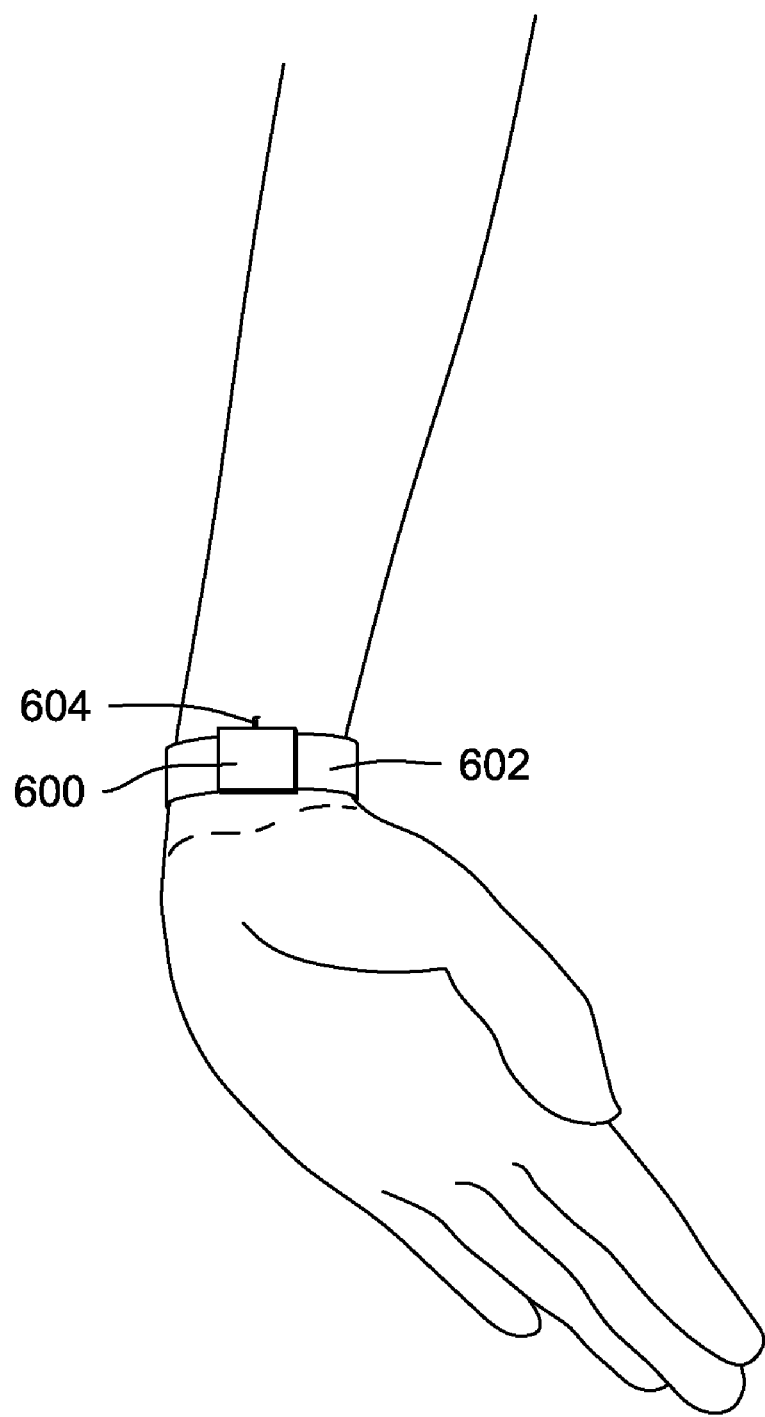
FIG. 23 is a perspective view of an illustrative example of the miniaturized portable cytometer having scattering and fluorescence detection systems adapted to be worn around the wrist.

FIG. 23 is a perspective view of an illustrative example of a miniaturized portable cytometer having both scattering and fluorescent detection and monitoring adapted to be worn around the wrist or palm. This cytometer 600 may be similar to that shown in FIGS. 1 and 16. A band 602 secures the miniaturized portable cytometer 600 to the wrist of a user.

As indicated above, the user may obtain a removable cartridge and provide a blood sample to the sample collector port 32 (see FIGS. 1, 16, 17 and 22) of the removable cartridge. The blood sample may be collected by, for example, a finger prick. The user may then insert the removable cartridge into the housing, and manually pressurize the system. The miniaturized and portable cytometer may then provide a reading that indicates if the user should seek medical treatment. The reading may be a visual reading, an audible sound or any other suitable indicator.

Rather than obtaining the blood sample by a finger prick or the like, it is contemplated that a catheter 604 or the like may be inserted into a vein of the user and attached to sample collector port 32. This may allow the system to automatically collect a blood sample from the user whenever a reading is desired. Alternatively, it is contemplated that the miniaturized portable cytometer may be implanted in the user, with sample collector port 32 connected to a suitable blood supply.

Figure 24:
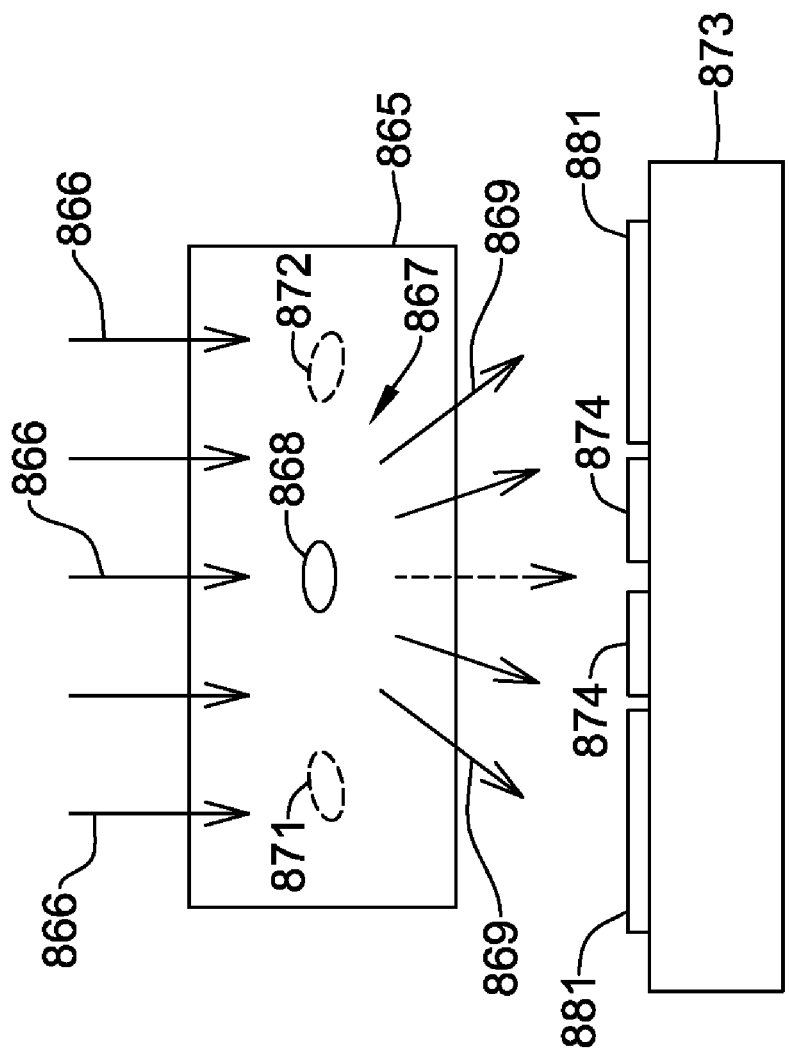
FIG. 24 shows a cross-section of a flow channel and an associated detector.

A flow channel 865, shown in FIG. 24, may have a cross-section of about 100×200 microns. A core stream 867 of particles 868 may be about 15-20 microns wide. The spot of light 866 may about 20×180 microns for a 670 nm red light. As illustrated in FIG. 24, the core may move side-to-side as shown by particle positions 871 and 872. Scatter 869 from the light 866 impinging the core stream 867 of single-file white blood cells 868 may be plotted with a photo detector 873 that measures a 1 to 3 degree band (FALS) with detection element 874 and a 3-11 degree band (SALS) with detection element 881 of scattered light 869. Detector 873 may also measure large angle scatter (LALS).

Figure 25B:
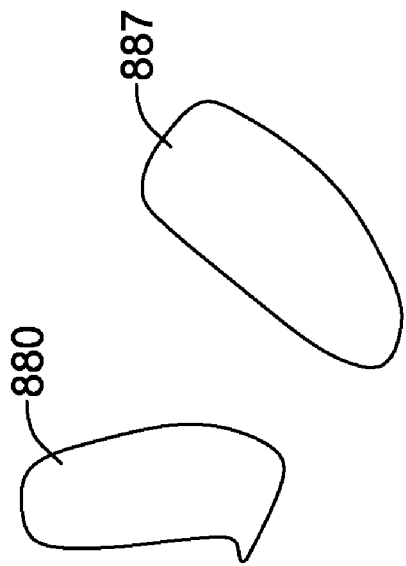

Pure scattering may enable identification of these types of white blood cells. A plot of the scatter is shown in FIG. 25a with FALS versus SALS and in FIG. 25b with FALS versus LALS data. The plot may enable one to identify the five types of white blood cells; curve 886 represents lymphocytes; curve 887 represents neutrophils; curve 888 represents eosinphils; curve 889 represents basofils; and curve 880 represents monocytes. The detector 873 may be an annular detector. However, it may instead be a linear detector. The annular detector may provide better quality detection but the linear detector may be less costly.

Besides the types of white blood cells, there may be various species of each type. For example, the lymphocyte may be of CD4, CD8, CD19 or another species. Another approach besides scattering to identifying the species is needed. For instance, there may be a Y shaped antibody for CD4 and there may be a blue fluorescent tag or marker on the antibody. There may be another antibody for CD5 which may be marked with a fluorescent tag of another color. The count of tags for various colors may be made by exciting the marker or tag with a light beam of another wavelength. A photo multiplier tube may be used to detect the fluorescent light. The number of CD4s, CD5s, and the like may be counted. The latter event is not done with scattering. However, scattering may still be needed and will be used to eliminate false counts due to the extra unattached antibodies.

One may take whole blood and lyse it (i.e., remove the red blood cells) to end up with white blood cells plus antibodies. A white blood cell may have an antibody complex. If there were 100 lymphocytes, one would need 100 antibodies for species identification and count purposes. There may be antibodies for other species besides CD4s and CD5s. There may be some extra tagged antibodies so as not to miss any species. There may be a surplus of antibodies but only those attached to a cell are counted since light scatter may be used to count the cells. Light scatter may be used to ferret out the unattached antibodies that are tagged.

A cell may have a dimension of about 12 microns whereas an antibody may have a dimension in the range of hundreds of nanometers. There may be other approaches to tagging such as the use of magnetic tags. The crux is that for each species, e.g., CD4, CD5, . . . , of a type of the white blood cell, one needs a separate and different color for each species. For instance, 20 different colors are needed to identify 20 various species in a single channel.

The various colors of the excited fluorescent tags may emanate out as one beam. These colors may be separated out in a big or brute force manner with a series of splitters tuned respectively to the different colors. A more compact approach a separation and detection of the various colors in the single light beam may be separated with a prism or a diffractive grating. The wavelengths, for example, may be 400, 430, 450, . . . , 670 nm, and so on.

Biological species may be an appropriate reference for such things as white blood cells. The sample observed may be from an environment and could have anthrax. The CD4 may be replaced by anthrax. In other words, an antibody may be used and replace the antibody used for CD4. One would need an antibody for each of the various things such as multiple agents within one system.

Monoclonal antibodies may be used instead of polyclonal antibodies. In FIG. 19a, there is a diagram of a lymphocyte with an antibody for CD4 and another one for CD8 in FIG. 19c. There may be antibodies for CD4 but they may go to CD8 which could result in false counts. That may be a problem which could occur with polyclonal antibodies. This problem may be solved with monoclonal antibodies since each would be characteristic so as to attach only to a CD4, CD8, or other designated species. Even though monoclonal antibodies are better quality and provide more accuracy than polynomial antibodies, the latter are significantly less expensive. Monoclonal antibodies are typically always used for CD4, CD8, and like domains.

As noted, there may be sub-classes of cells. Species may be warfare agents. Agents may include malaria, TB, and the like. Malaria may be in the blood, so there may be an antibody for malaria Biological species may be in blood, warfare agents in water, and diseases in the blood. These kinds of biological species may be identified with antibodies having tags.

An antigen may look like an antenna (FIG. 19a) attached to, for instance, a CD4. The identification and counting of biological species in a handheld cytometer may provide preventive care in remote areas of the world. The handheld cytometer may be fully automated for sample preparation and analysis. Most, if not all cytometers, will not function with a sample from just a finger prick. The latter may be achievable for an untrained user of the cytometer. A sample may be needed only once a month. Laser pricking may be used with the present cytometer, but such approach is more expensive than an ordinary finger prick. Various other cytometer systems may require an actual draw of a substantial amount of blood.

Figure 26:
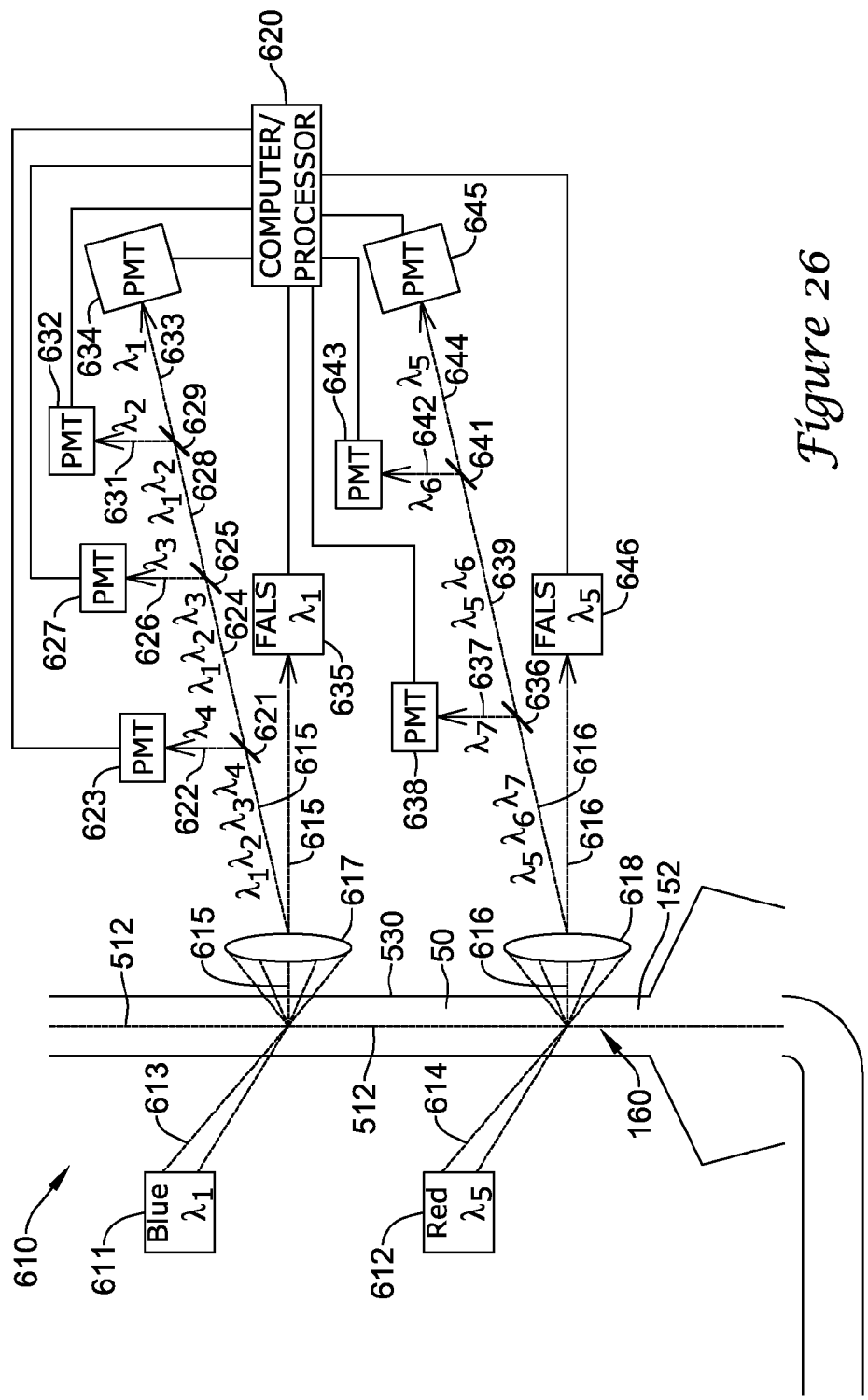
FIG. 26 is a diagram of a system having a two-color light source arrangement with a dual in-line fluorescent and scattered light detection arrangement.

FIG. 26 shows a miniaturized cytometer 610 having a flow stream path 50 with a core stream 160 surrounded by a sheath fluid 152. Core stream 160 may contain particles 512 flowing single-file through a flow channel 530. The width or diameter dimensions of channel 530 may be reduced to a size so that the particles 512 move through the channel in a single file. The velocity of the sheath fluid 152 may be significantly greater in magnitude than that of the core stream of particles 512 to assist in the single-file flow.

Particles 512 may be cells or other constituents of a fluid or substance. These particles may be white blood cells which have antibodies associated with them. The antibodies may have markers or tags attached to them. FIGS. 18, 19a and 19b along with their associated discussion in the present description illustrate the marker or tag structure. These white cells may be impinged with light which causes their associated markers or tags to fluoresce and emit light. The light may be collected, filtered as needed, and directed to one or more photo detectors. The photo detectors may be used to assist in the identification and monitoring of specific subclasses of white cells and blood based proteins, among other things.

A light source 611 may emit a blue light 613 having a wavelength $\lambda$, which may impinge particles 512. Particles 512 may each have a dye, tag or marker that absorbs light 613 and in response fluoresces and emits a light 615 of a particular wavelength, such as $\lambda_1$, $\lambda_2$, $\lambda_3$, and/or $\lambda_4$. The particular wavelength may be of a dye, tag or marker, associated with a certain kind of particle such a specific species of a white blood cell. An identifier of the particle may be a fluorescent dye or phosphor marker which may emit light at a wavelength different from that of an identifier of another particle for the purposes of identifying the particle that it is attached to or associated with and differentiating it from other particles. There may be identifiers of many different wavelengths/colors (e.g., 8, 16 or 32+) for distinguishing various particles from the other particles, approximately simultaneously.

Light 615 may go through an optics 617. Such optics may be of various configurations as noted above. Also, light source 611 may have a special optics built in to the source or be integrated close on or at channel 530. Optics 617 may direct light 615 through filters dichroic beam splitters or other wavelength separating mechanisms. For instance, beam 615, having wavelengths $\lambda_1$, $\lambda_2$, $\lambda_3$, and $\lambda_4$ may go to a beam splitter 621 which splits off a light beam 622 having wavelength $\lambda_4$ which is sensed by detector 623. A remaining light beam 624 may have wavelengths $\lambda_1$, $\lambda_2$, $\lambda_3$ and impinge a splitter 625 which may split off a beam 626 having a wavelength $\lambda_3$. Light beam 626 may be detected by detector 627. A remaining light beam 628, having wavelengths $\lambda_1$, $\lambda_2$, may continue from splitter 625 to a splitter 629. Splitter 629 may split off a beam 631 having a wavelength $\lambda_2$ and be detected by a detector 632. A remaining light beam 633 may continue from splitter 629 and impinge a detector 634. Electrical signals from detectors 623, 627, 632 and 634 may go to a computer and/or processor, hereafter referred to as a computer. Detectors 623, 627, 632 and 634 may be PMT detectors. The FALS detector 635 may be a silicon photo diode. There may be more or less than four wavelengths and four or so corresponding detectors relative to beam 615 of wavelengths of light from markers excited by light 613 of blue source 611. Source 611 may be a laser diode or another kind of effective light source.

Also, a scattered light 615 may proceed on from optics 617 to a FALS detector 635 sensitive to the wavelength $\lambda_1$. Electrical signals from detector 635 may go to computer 620. Detector 635 may be used for measuring forward angle scattering (FALS) produced by selected particles 512 in the flow stream 50 at wavelength $\lambda_1$.

At another location along flow channel 530 may be another beam 614 impinging particles 512. Such beam 614 may be emanated by a red light source 612 having a wavelength $\lambda_5$. Light source 612 may be a laser diode, VCSEL or another kind of effective light source. Particles 512 may each have a dye, tag or marker that absorbs light 614 and in response fluoresces and emits a light 615 of a particular wavelength, such as $\lambda_5$, $\lambda_6$, and/or $\lambda_7$. A particular wavelength may be of a dye, tag or marker, associated with a certain kind of particle such as a specific white cell. Light 616 may go through an optics 618. Such optics may be of various configurations as noted above. Also, light source 612 may have a special optics built into the source or be integrated close on or at channel 530. Optics 618 may direct light 616 through filters, dichroic beam splitters or other wavelength separating mechanisms.

For instance, beam 616, having light of wavelengths $\lambda_5$, $\lambda_6$ and $\lambda_7$, may go to a dichroic beam splitter 636 which splits off a light beam 637 having a wavelength $\lambda_7$ which is detected by a detector 638. The remaining portion of the beam having wavelengths $\lambda_5$ and $\lambda_6$ may proceed through splitter 636 as a beam 639. Beam 639 may impinge a beam splitter 641 which may direct a light beam 642 having a wavelength $\lambda_6$. Beam 642 may be detected by detector 643. The remaining portion of the beam may proceed through splitter 641 as beam 644 having a wavelength $\lambda_5$. Beam 644 may be detected by detector 645. Electrical signals from detectors 638, 643 and 645 may go to computer 620. These detectors may be PMT detectors.

Also, a scattered light 616 may proceed on to a FALS detector 646 sensitive to the wavelength $\lambda_5$. Electrical signals from detector 646 may go to computer 620. Detector 646 may be used for measuring forward angle scattering produced by particles 512 in the flow stream 50 at wavelength $\lambda_5$. The FALS detector 646 may be a silicon photo diode. There may be more or less than three wavelengths and four corresponding detectors relative to beam 616 of wavelengths from markers excited by light 614 of red source 612.

The pitch for the PMT detectors of arrays used as illustrative instances in the various systems may involve about a 1 mm center-to-center spacing of the adjacent detectors with each having an active area. The active area of the individual detectors may be circular with a 0.8 mm diameter, or rectangular with about a 0.8 mm short dimension. The detectors may have other shapes. The pitch and active area dimensions may be different for various applications. One array that may be used is one provided by Hamamatsu Corporation with a part number R5900U-04-L32 which may be a 32 channel linear array for detecting 32 different wavelengths or colors for identification and measurement. Greater numbers of wavelengths or colors may be monitored as arrays with more channels become available.

Figure 27:
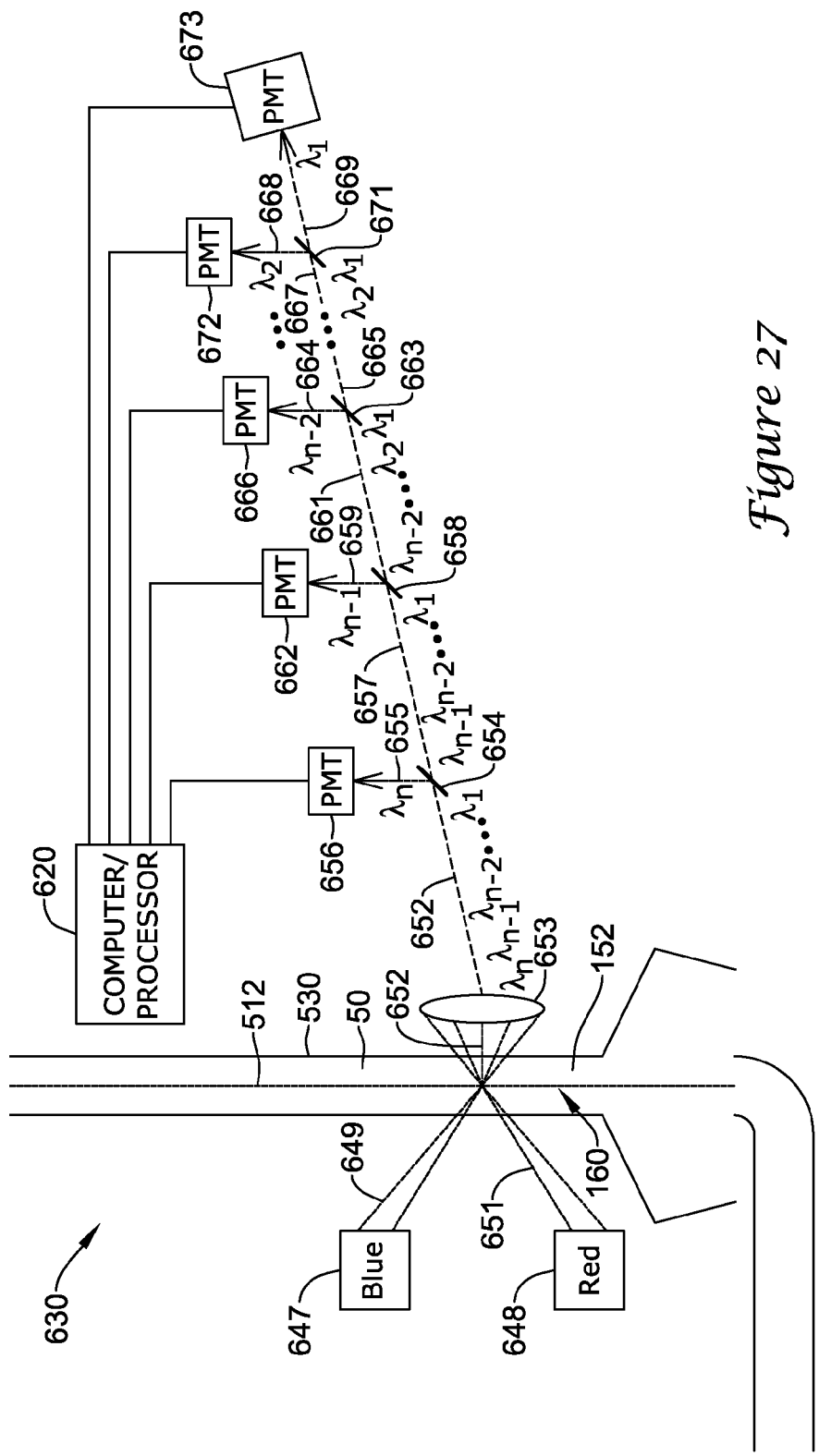
FIG. 27 is a diagram of a detection system similar to that of FIG. 26 with the focusing of the light source outputs to one place in the flow channel and an in-line detection arrangement.

FIG. 27 shows a configuration 630 where several light sources 647 and 648 have their beams 649 and 651, respectively, focused on one spot in the flow stream 50. At this spot, the light beams 649 and 651 may impinge particles 512 which may each have a dye, tag or marker that absorbs light 649 and/or 651 and in response may fluoresce and emit light 652 of a particular wavelength such as $\lambda_n, \lambda_{n-1}, \lambda_{n-2}, \ldots, \lambda_1$. A particular wavelength may be of a dye, tag or marker, associated with a certain kid of particle such as a specific species of a white cell. Light 652 may go through an optics 652. Such optics may be of various configurations as noted above. Light sources 647 and 648 may be blue and red sources, respectively. These sources 647 and 648 may each have a special optics built into it. Or such optics may be integrated close to or at channel 530. Light sources 647 and 648 may be a laser diode, VCSEL or another kind of effective light source.

The angles of the light from the blue and red sources may be at 45 degrees relative to the direction of flow. This approach may keep the light of the sources from mixing in with the emitted fluorescent light and affecting signal-to-noise ratios of the fluorescent light.

Light 652 may be collimated or focused in a desired manner by an optics 653. These optics may be of several configurations noted above such as being integrated close to or at channel 530. Beam 652, having wavelengths $\lambda_n$ to $\lambda_1$, may proceed on to a dichroic beam splitter 654. Such splitter may be a filter, prism or other device for separating out the various wavelengths of light beam 652. Splitter 654 may split out a beam 655, having a wavelength $\lambda_n$, which may proceed on to be detected by a detector 656. Detector 656 may send an electrical signal to computer 620.

The remaining light of beam 652 may proceed on through splitter 654 as a beam 657 having wavelengths $\lambda_{n-1}$, $\lambda_{n-2}, \ldots, \lambda_1$. Beam 657 may proceed on to a splitter 658. Splitter 658 may split beam 658 into beams 659 and 661. Beam 659, having a wavelength $\lambda_{n-1}$, may impinge a detector 662 which in turn can send an electrical signal, representing light beam 659, to computer 620. The remaining light of beam 657, beam 661 having wavelengths $\lambda_{n-2}, \ldots, \lambda_2, \lambda_1$, may proceed on to splitter 663 and be split into beams 664 and 665. Beam 664, having a wavelength $\lambda_{n-2}$, may proceed on to a detector 666. Detector 666 may sense beam 664 and send an electrical signal to computer 620. Beam 665, having wavelengths $\lambda_{n-3}, \ldots, \lambda_2, \lambda_1$, may go on toward an n-3 number of splitters and detectors, respectively. "n" may be any number but ten or less may be practical for the same number of colors being split off and detected by system 630. Ten or less may also be a practical number for the other detection systems noted here.

After an intermediate number of splitters and detectors, subsequent to splitter 663 and beam 665, there may be a beam 667 near the end of the sequence of splitters and detectors of system 630. Beam 667, having wavelengths $\lambda_2$ and $\lambda_1$, may be split into beams 668 and 669 by a splitter 671. Beam 668, having a wavelength $\lambda_2$, may impinge detector 672 which may in turn send a representative electrical signal to computer 620. Beam 669, having a wavelength $\lambda_1$, may be detected by detector 673 which may send an electrical signal about beam 669 to computer 620. Detectors 656, 662, 666, 672 and 673 may be PMT detectors, CCD detectors, silicon photo detectors, avalanche photo detectors, and/or other kinds of detectors.

Figure 28:
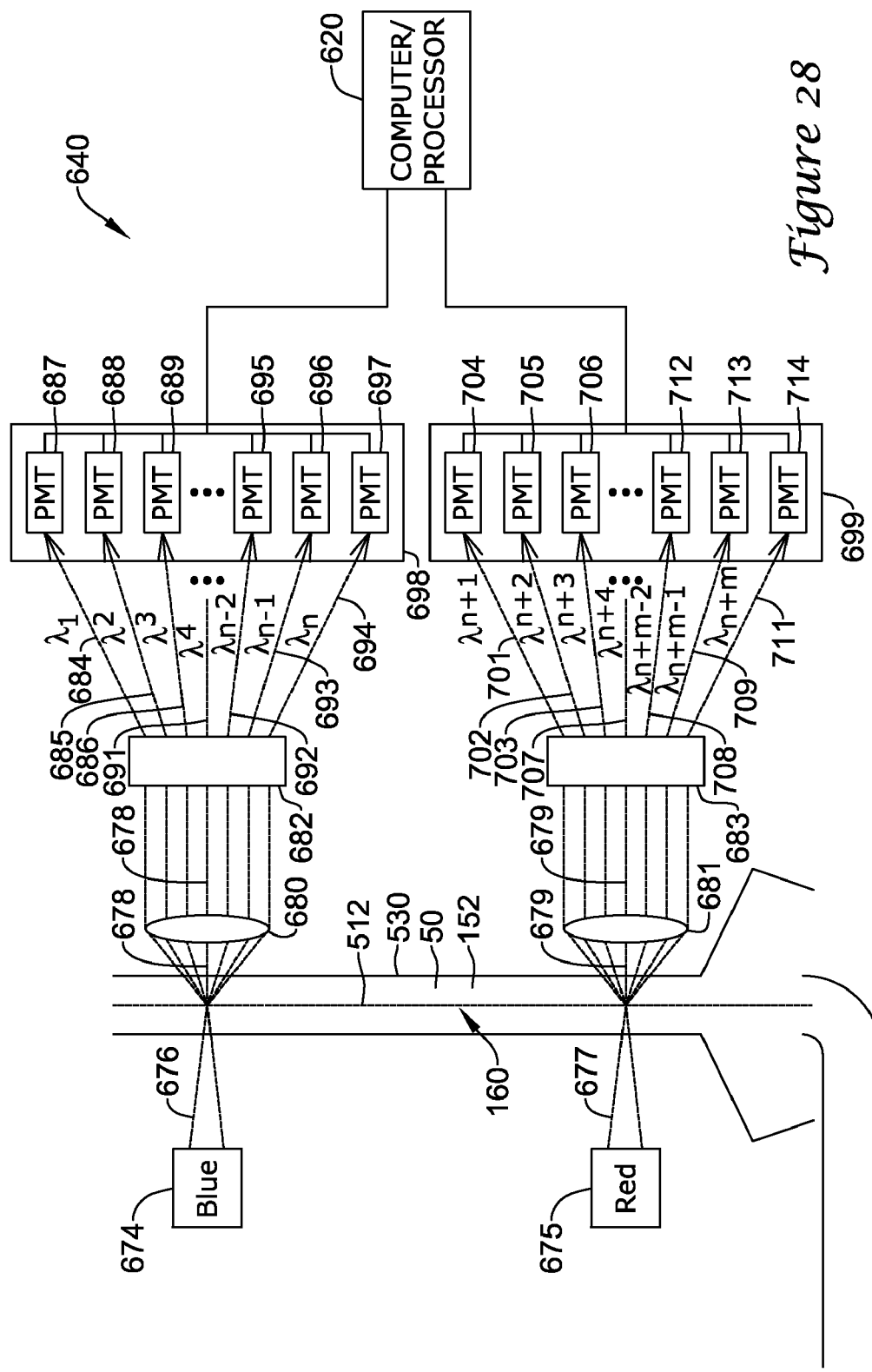
FIG. 28 shows a dual color light source system using a dispersive color separation and detection arrangement.

FIG. 28 reveals a detection system 640 which may use gratings (e.g., optical or arrayed waveguide gratings) or prisms for segregating wavelengths out from a beam of light. A blue light source 674 may emanate a beam 676 which may impinge a particle 512. Similarly, a red light source 675 may emanate a beam 677 which may impinge a particle 512. The beams 676 and 677 may be focused on spots in flow stream 50 where the beams, respectively, may impinge particles 512. Particles 512 may each have a dye, tag or marker that absorbs light 678 and/or 677 and in response may fluoresce and emit light 678 and/or light 679. Light 678 may have wavelengths $\lambda_1, \lambda_2, \ldots, \lambda_{n-1}, \lambda_n$. Light 679 may have wavelengths $\lambda_{n+1}, \lambda_{n+2}, \ldots, \lambda_{n+m-1}, \lambda_{n+m}$.

Light 678 may go through an optics 680 to be collimated or focused for projection on to a light wavelength separator 682. Light 679 may go through an optics 681 to be collimated or focused for projection on to a wavelength separator 683. Optics 680 and 681 may be of various configurations as noted above. Light sources 674 and 675 may each have special optics built into it. Or such optics may be integrated close to or at channel 530. Sources 674 and 675 may be a laser diode, VCSEL or another kind of effective light source.

Light 678 may be split out or separated according to wavelength or color by a separator 682 which may be a diffractive grating, prism or like optical mechanism. Light 679 may likewise be split out or separated according to wavelength or color by a separator 683 which may be a diffractive grating, prism or like optical mechanism.

Light beams 684, 685 and 686 from separator 682, having wavelengths $\lambda_1, \lambda_2$, and $\lambda_3$, respectively, may impinge detectors 687, 688 and 689 of an array 698 as shown in FIG. 28. The number of wavelengths or colors from optical mechanism 682 may be "n". Beam 691 may be a middle beam from separator 682 that represents the beams of wavelengths from $\lambda_4$ to $\lambda_{n-3}$ and the respective PMT detectors. The remaining three beams 692, 693, 694 may have wavelengths of $\lambda_{n-2}$, $\lambda_{n-1}$, and $\lambda_n$, with detectors 695, 696 and 697, respectively, to detect them. Detectors 687, 688, 689, 695, 696, 697 and other detectors of array 698 may have electrical outputs connected to processor 620. These detectors may be PMT devices.

Light beams 701, 702 and 703, as shown in FIG. 28, having wavelengths $\lambda_{n+1}, \lambda_{n+2}$, and $\lambda_{n+3}$, respectively, may impinge detectors 704, 705 and 706 of array 699. The number of wavelengths or colors from optical mechanism 683 may be "m". The wavelengths of beams from mechanism may be sequenced including those from mechanism 682. Optical mechanisms 682 and 683 may be prisms or gratings that spatially spread out the light according to wavelength. Beam 707 may be the middle beam from separator 682 that represents the beams of wavelengths from $\lambda_{n+4}$ to $\lambda_{n+m-3}$ and the respective detectors. The remaining three beams 708, 709 and 711 may have wavelengths of $\lambda_{n+m-2}, \lambda_{n+m-1}$ and $\lambda_{n+m}$, with detectors 712, 713 and 714 to detect them. Detectors 704, 705, 706, 712, 713, 714 and other detectors of array 699 may have electrical outputs connected to computer 620. These detectors may be PMT devices.

Figure 29:
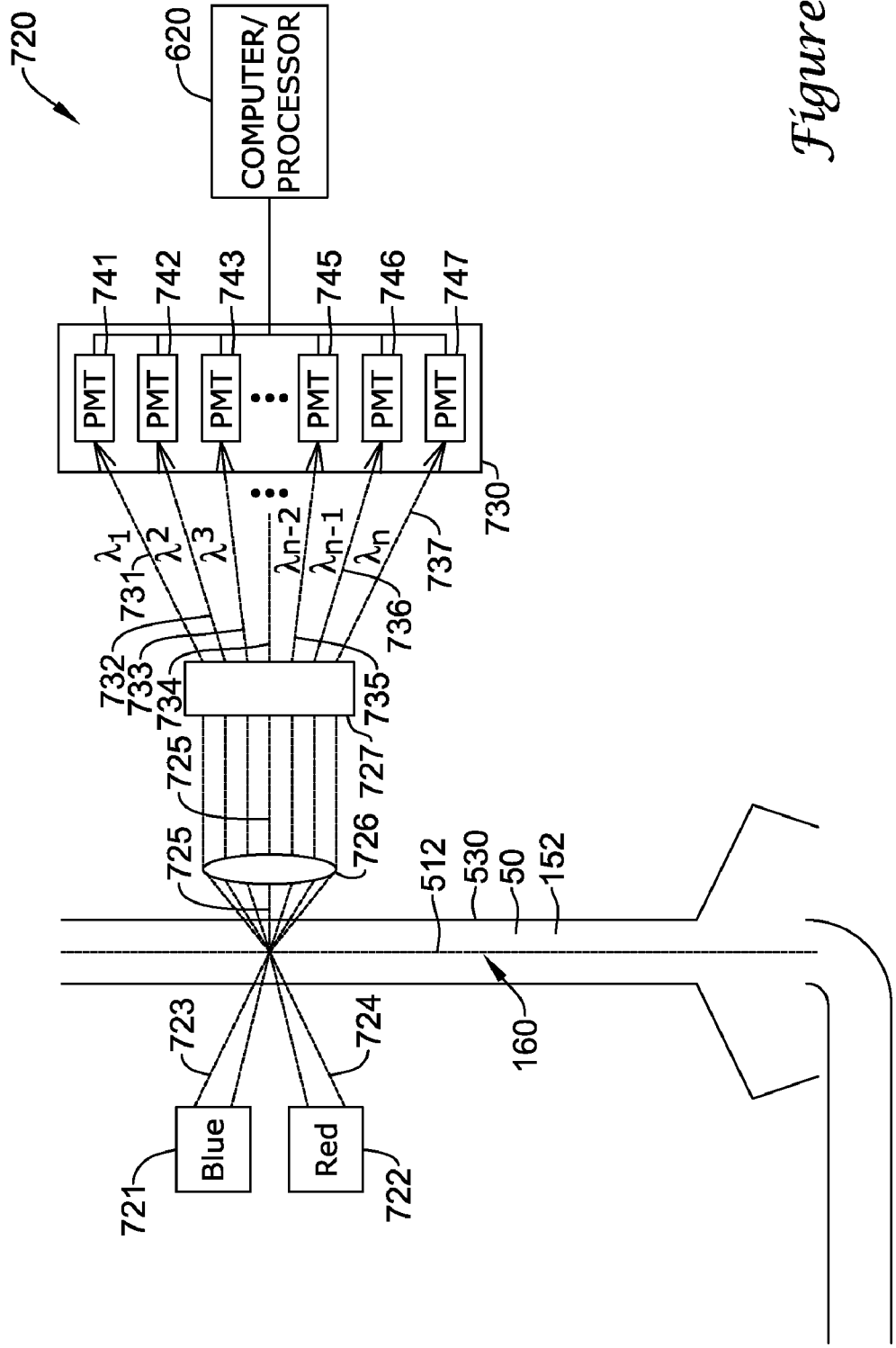
FIG. 29 shows a system like that of FIG. 28 except that the light source outputs may be focused at one place in a flow channel.

FIG. 29 shows a system 720 that may be similar to system 640 of FIG. 28 except the blue source 721 and red source 722 may have their outputs 723 and 724 combined and impinge cells 512 at one place thereby resulting in markers being excited and emitting fluorescent light 725 of various wavelengths or colors. Light 725 may be collimated by a lens 726 and in turn spit out or separated out into light various wavelengths according to wavelength or color by a separator 727, which may be a prism, diffractive grating, or the like. Light beams 731, 732 and 733, having wavelengths $\lambda_1, \lambda_2$, and $\lambda_3$, respectively, may impinge detectors 741, 742 and 743, respectively, of an array 730 which may include PMTs. The number of wavelengths or colors may be "n". Beam 734 may be a middle beam from separator 727 that may represent beams of wavelengths from $\lambda_4$ to $\lambda_{n-3}$ and the respective detectors of array 730. The shown remaining three beams 735, 736 and 737 may have wavelengths $\lambda_{n-2}$, $\lambda_{n-1}$ and $\lambda_n$, with detectors 745, 746 and 747, respectively, to detect them. Detectors 741, 742, 743, 745, 746, 747 and the other detectors of array 730 may have electrical outputs connected to processor 620.

Figure 30:
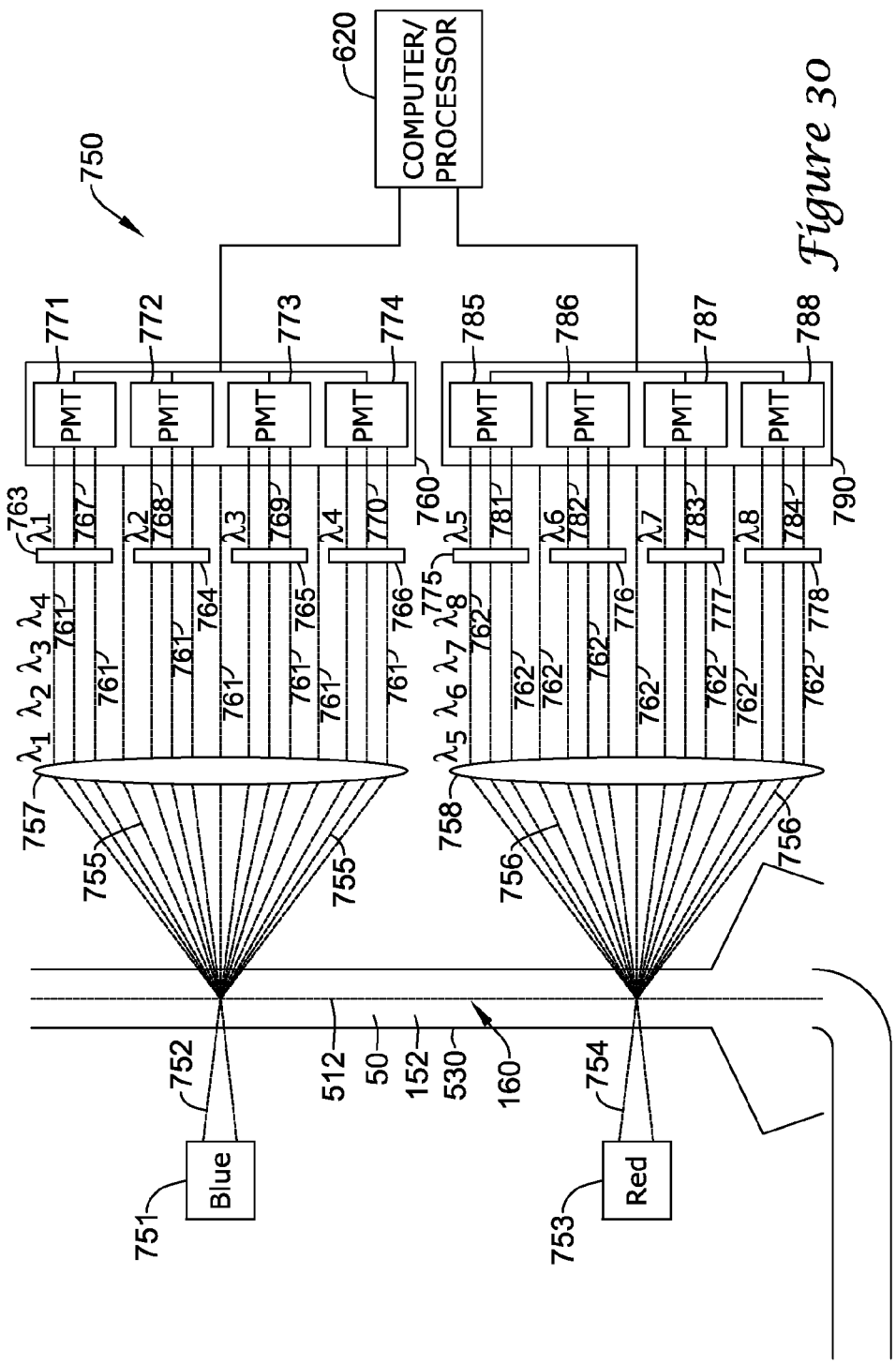
FIG. 30 is a diagram of a several-light source and detector arrangement using filters for light separation.

FIG. 30 shows a system 750 that may use filters to separate out the various wavelengths of a beam of fluorescent light. A blue light source 751 may emit a light beam 752 to impinge a cell 512 in channel 530. Similarly, a red light source 753 may emit a light beam 754 to impinge a cell 512 in channel 530. Impingement of cells 512 may result in the emission of fluorescent beams 755 and 756. Lenses 757 and 758 or like optical devices may collate the light beams 755 and 756 into light 761 and 762, respectively. Light 761 may have various wavelengths or colors that can be separated out with filters 763, 764, 765 and 766 into light beams 767, 768, 769 and 770 having wavelengths $\lambda_1$, $\lambda_2$, $\lambda_3$, and $\lambda_4$, respectively, which in turn may be detected by detectors 771, 772, 773 and 774 of an array 760.

Likewise, light 762 may have various wavelengths or colors that can be separated out with filters 775, 776, 777 and 778 into light beams 781, 782, 783 and 784 having wavelengths $\lambda_5$, $\lambda_6$, $\lambda_7$, and $\lambda_8$, respectively, which in turn may be detected by detectors 785, 786, 787 and 788 of an array 790. The arrays 760 and 790 may have PMT detectors. Also, the detectors of arrays 760 and 790 may instead be encompassed in one array. The number of wavelengths of system 750 may be more or less than eight.

Figure 31:
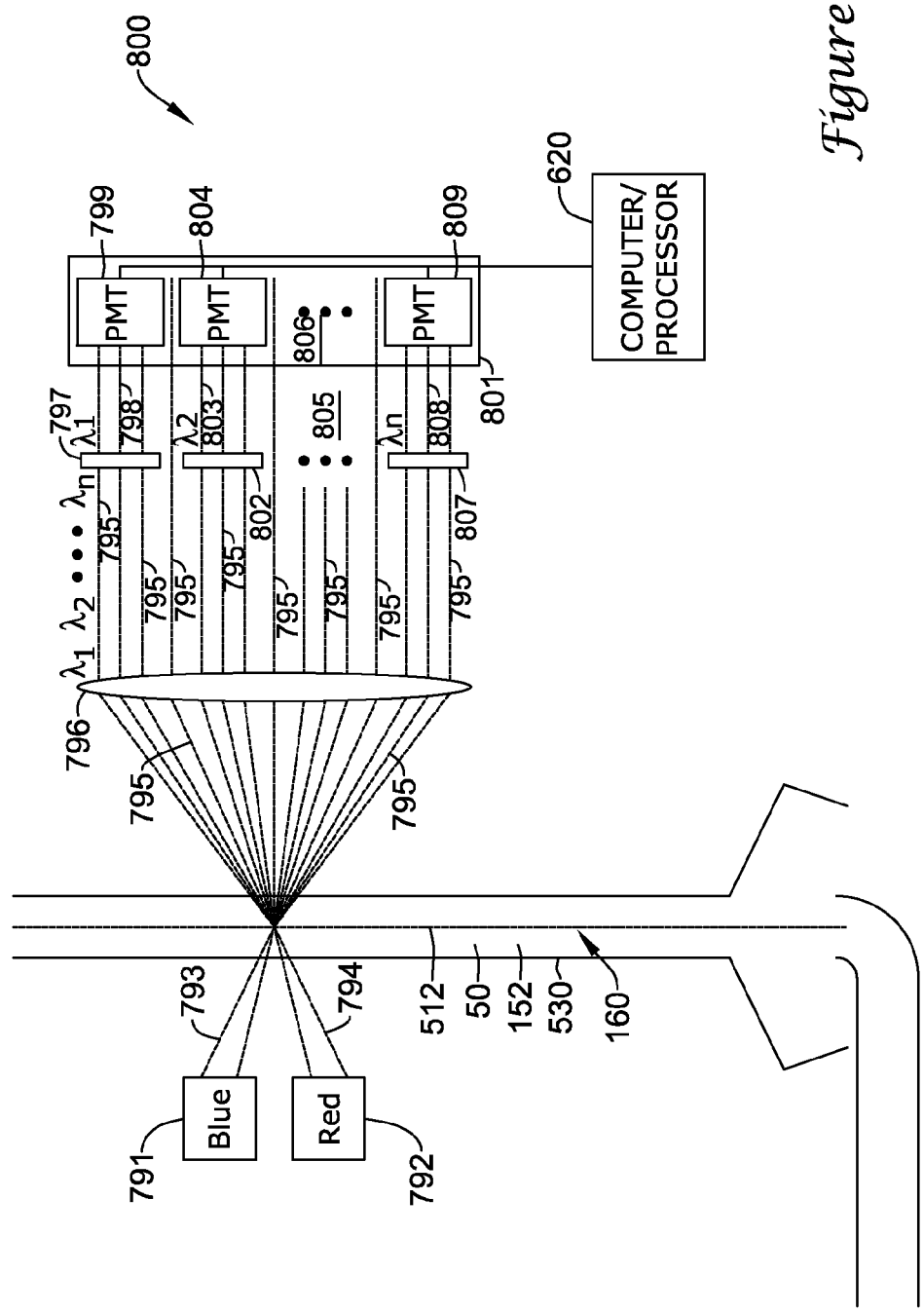
FIG. 31 shows a system similar to that of FIG. 30 except that the light source outputs are focused at one place in a flow channel.

System 800 of FIG. 31 may be similar to system 750 of FIG. 30, except that the blue light source 791 and red light source 792 may have their outputs 793 and 794 combined and impinge cells 512 at one place thereby resulting in markers being 795 excited and emitting fluorescent light 795 of various wavelengths or colors. Light 795 may be collimated by a lens 796. Light 795 may be filtered by a filter 797 resulting in a light 798, having a wavelength $\lambda_1$, which may be detected by a detector 799 of an array 801. Light 795 may be filtered by a filter 802 resulting in a light 803, having a wavelength $\lambda_2$, which may be detected by a detector 804 of array 801. Light 795 may be filtered by numerous filters in area 805 resulting in light of wavelengths $\lambda_3$ through $\lambda_{n-1}$ which may respectively be detected by detectors via area 806 of array 801. Light 795 may be filtered by a filter 807 resulting in a light 808, having a wavelength $\lambda_n$, which may be detected by a detector 809 of array 801. The outputs of detectors 801, 804, 809 and other detectors may be connected to the computer/processor 620. The detector arrangement for the systems of FIGS. 28-32 may have numerous detectors for detecting as many as 8, 16, 32 or more colors without a significant increase in size of the detector arrangement or footprint. Numerous detectors may be encapsulated in a miniature package.

Figure 32:
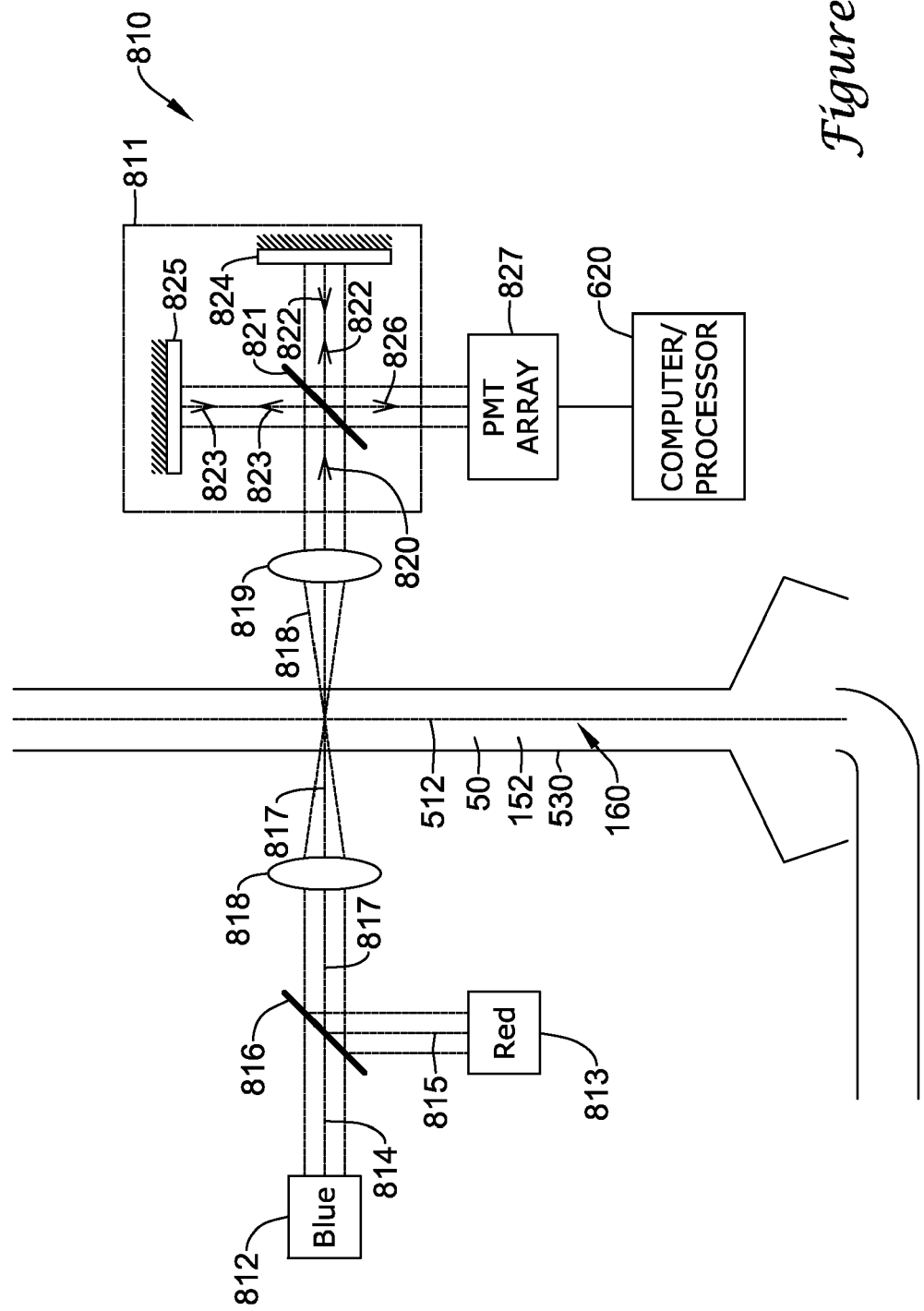
FIG. 32 is a diagram of a detection system using an interferometric color distinguishing arrangement.

FIG. 32 shows a stationary Fourier transform spectrometer system 810 utilizing a Michelson interferometer 811. A blue light source 812 and red light source 813 may emit light 814 and 815, respectively, which is combined at a splitter 816 into a light 817. Lens 818 may focus light 817 onto cells 512. Cells 512 may have markers that are excited by light 817 and emit fluorescent light 818 having a variety of wavelengths or colors. Lens 819 may collimate light 818 into light 820. Light 820 may impinge a splitter 821 which splits light 820 into light 822 and light 823. Light 822 may be reflected by a mirror 824 back to splitter 821. Similarly, light 823 may be reflected by a mirror 825 back to splitter 821. Some of light 822 and 823 may be combined into a light 826. As a result of interference, the light 826 may have an intensity modulation spread on a one dimensional array 827 of detectors where each may individually sense an intensity value. The outputs of the detectors of array 827 may go to the computer/processor 620 by which one may process the intensity modulation across the array to obtain the spectral content (i.e., color) of the interfering light.

Figure 33:
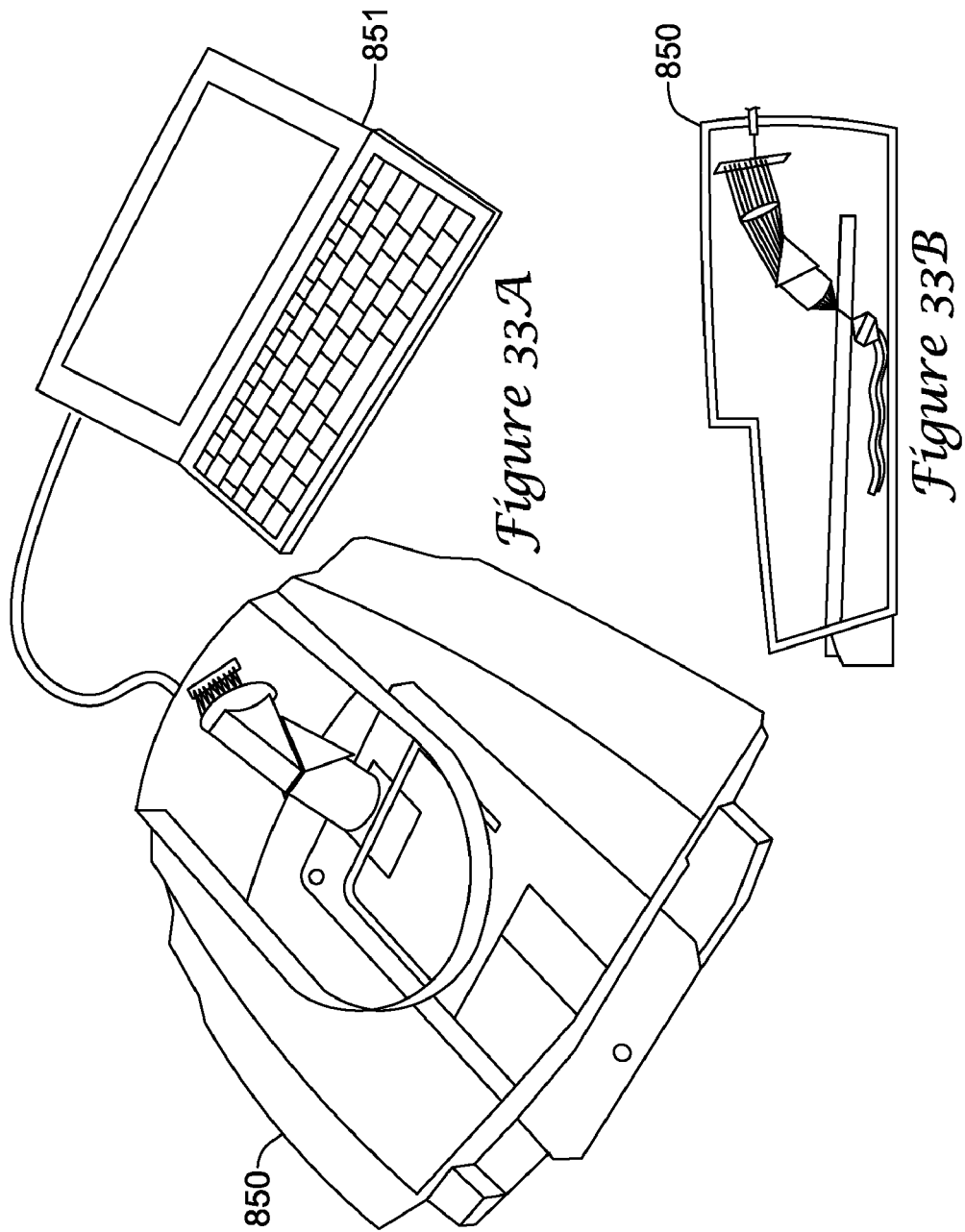
FIGS. 33a and 33b show perspective and cross-sectional views, respectively, of a handheld cytometer detection system.

FIG. 33a shows a perspective view of a handheld multiplexed cytometer system 850 for BW agent detection in environmental samples. FIG. 33b shows a cross-section view of the cytometer 850. It may be a multi-color fluorescence-based cytometer that detects multiple classes of biowarfare (BW) agents (bacteria, viruses, spores, and toxins). The cytometer 850 may be connected to a palmtop or other computer 851 for operation control, data acquisition and analyses. The cytometer system 850 may perform immunoassay-based (including bead based assays) detection of BW agents in a cytometer format. The microcytometer 850 may incorporate the advantages of immunoassay based detectors with the added benefits of a very small system size (<5 lbs.), higher throughput, automated sample preparation on a microfludic cartridge 852, maintenance-free operation by untrained personnel, and very low logistical burden enabled by assay implementation in a microfluidics format.

This technology may be less sensitive and specific than a polymerase chain reaction (PCR) based detector but has the following advantages over the state-of-the-art PCR detector, which may include higher overall speed of response, ability to detect toxins, simpler sample preparation steps, and maintenance-free system that can be operated by the unskilled operator.

There may be a scaleable multi-color fluorescence-based flow cytometer 850 for BW agent detection. A four-color cytometer may be capable of identification and counting of four different BW agents and simulants. A demonstration may be based on "pure" biological samples of simulants and inactivated BW agents (and not necessarily based on real environmental samples). The design and approach however can be scaleable to 32-different colors. A 32-color cytometer system implies the capability to simultaneously detect 32 different agents in a given input sample.

System parameters may be quantified on a basis of measurements on biological samples of simulants and inactivated BW agents with sensitivity, specificity, limit of detection (LOD), and probability of detection. The simulants and inactivated BW agents that may be tested are *bacillus subtilis* (bacteria in spore form), *escherichia coli* (vegetative bacteria), MS2 bacteriophage (virus), and ovalbumin (protein), inactivated bioagents *bacillus anthracis* spores, and stapylococcal enterotoxin B.

A fully integrated, handheld flow cytometer may have automated sample preparation capabilities. Such a system may be capable of simultaneous detection of multiple BW agents in environmental samples and may be designed to be interfaced with ancillary instruments like aerosol sample collectors and other pre-concentration devices.

The system 850 may be used to test blood samples for clinical applications and yet be customized for BW agent detection from "pure" biological and environmental samples, respectively. Aspects of the handheld cytometer system 850 make it useful with a detector suite designed to provide defense against a BW agent attack. The system 850 may include fast detection (<5 minutes), high specificity (same levels of specificity as traditional immunoassay based sensors) for the detection of diverse range of BW agents (bacteria, viruses, spores, and toxins), maintenance-free optical scattering module with self-alignment capability, overall system self-diagnostic capabilities, small size (the system may be handheld), low weight (<7 lbs including the computer), low power (battery operated), and high throughput (detection of up to 1000 cells per second. It may be useable by untrained personnel since the environmental sample can be introduced directly onto the microcytometer card 852 and sample preparation can be performed on the disposable analysis cartridge 852 in an automated way, i.e., antibodies may be mixed with antigens in an area 856 of the card, and eliminating benchtop washing and incubation steps. The instrument 850 may require no operator intervention during the analysis phase at portion 857 of card 852, i.e., no knobs to adjust, nothing to calibrate by the operator, and the like.

All hazardous substances may remain encapsulated on the card 852 for safe handling in storage area 853 and disposal. The analysis cartridge may provide full retention of reagents 854 and waste on the card. This means that the unskilled user should not be exposed to the biological agents. System 850 may have a very small logistical burden in that small quantities (less than a µL) of expensive reagents are needed and a small volume of self-contained waste is generated. BW agent samples may be stored for further analysis on the disposable analysis cartridges 852. System 850 may provide an orthogonal detection method to the alternate specific BW agent detector, viz., the PCR type of detector.

In addition, the microcytometer 850 may be used in a second operation mode, viz., as an automated sample preparation system that can filter, sort, and pre-concentrate BW agent species from an input environmental sample. In this second mode of operation, the microcytometer 850 may be used as a front-end for a PCR based detector, resulting in a battery operated, and portable BW agent detector capable of highly specific and highly sensitive detection.

An integrated scattering and fluorescence flow cytometer 850 may be capable of counting and classifying white blood cells from a whole blood sample input. The three-part differentiation of white blood cells using a cytometer 850 may have the following steps including automated sample preparation on the cartridge 852, red VCSEL array based electronic self-alignment, highly miniaturized three-channel pumping system, custom-developed electronics and a graphic user interface. A fluorescence optical arrangement may be miniaturized and combined with a counting cytometer to develop a final system capable of both scattering and fluorescence based detection. One may modify and customize the flow cytometer 850 for detection of BW agents in biological and environmental samples.

The microcytometer 850 has numerous advantages relative to other kinds of detectors and formats such as the mass spectrometer, PCR, intrinsic fluorescence measurement, and immunoassay formats (e.g., ELISA and lateral flow assays). The sensitivity for the microcytometer is medium. It is medium for immunoassay formats, low for intrinsic fluorescence measurement, high for the PCT and high for the mass spectrometer. However, for the mass spectrometer, detection is extremely slow to analyze a large enough volume. As to quantification of agent concentration, there is such for the microcytometer, immunoassay formats and the PCR. There is no quantification of agent concentration for the intrinsic fluorescence measurement and the mass spectrometer.

As to specificity of detection, it is high for the microcytometer. The microcytometer can detect bacteria, viruses, spores and toxins. The specificity of detection is high for immunoassay formats and low for intrinsic fluorescence measurement. It is high for PCR though the PCR cannot detect toxins. The specificity of detection is theoretically high for the mass spectrometer; however, practical limitations exist due to a huge number of datapoints. Sample preparation is medium for the microcytometer and can be automated on a microfluidic card. For the immunoassay formats and the mass spectrometer, the sample preparation is extensive. Sample preparation for the PCR is medium. There is no sample preparation for intrinsic fluorescence measurement.

The speed of detection after sample preparation is fast (less than 5 minutes) for the microcytometer, slow (about 30 minutes) for immunoassay formats, fast but non-specific for the intrinsic fluorescence measurement, slow (about 30 to 45 minutes) for the PCR, and medium (about 15 to 30 minutes) for the mass spectrometer. The power consumption is low for the microcytometer, medium for immunoassay formats, medium for the intrinsic fluorescence measurement, low for the PCR, and medium for the mass spectrometer. The size and weight of the currently available technology are small for the immunoassay formats, medium for the intrinsic fluorescence measurement, small for the PCR, and medium for the mass spectrometer. The size and weight are very small (handheld) for the microcytometer.

The microcytometer has no major disadvantages. The other technologies have some disadvantages. The immunoassay formats have much lower throughput than a flow cytometer. Also, the formats cannot be easily automated or made to interface with sample collection systems. The intrinsic fluorescence measurement has very poor specificity. The PCR does not work with protein-based toxins. The mass spectrometer is unlikely to be able to process enough sample volume for obtaining good sensitivity unless an extremely good sample pre-concentration step can be developed. Also, the spectrometer would need a vacuum source and a complex data analysis.

The microcytometer 850 may fit in the category of a core BW agent detector (because it may perform immunoassays in a cytometer format). A summary comparison of cytometer 850 with other similar BW agent detectors. The microcytometer 850 incorporates the advantages of the traditional immunoassay based detectors with the added benefits of automated operation by untrained personnel, very small size (<5 lbs), and high throughput. Microcytometer 850 may be less sensitive and specific than a PCR based detector but has the additional advantages over a PCR detector such as higher response speed, ability to detect toxins, being maintenance-free and having self-contained analysis cartridges 852 for easy disposal of hazardous BW materials.

Flow cytometer 850 may perform scattering and fluorescence based optical detection to simultaneously identify and quantify BW agents in an environmental sample. The measurement technique may be based on antibody-antigen type immunoassay (including bead based assays) that can be detected by fluorescence measurements from antibodies tagged with commercially available fluorescent dyes. Cytometer 850 may be designed to detect BW agents in any type of environmental sample, e.g., air, water, or food sample. The cytometer may identify and count simulants and inactivated BW agents in "pure" biological samples. A fully integrated, field-portable cytometer system 850 may also identify and count multiple BW agents from real world environmental samples.

A simultaneous detection of multiple BW agents by a cytometer system 850 may lead to discrimination between different wavelengths (colors) with finer resolution. Cytometer system 850 may identify biological species by examining several types of light signals, i.e., fluorescence emission from tagged antibodies and scattered light from the antibody-antigen complexes. The cytometer system 850 may be set-up as a clinical palmtop cytometer. Cytometer 850 may be designed to detect BW agents in pure biological and environmental samples. It may have an electronic self-alignment scheme that allows for good optical alignment between the laser light and the core flow of the cytometer channel, resulting in the development of an easy-to-use, maintenance-free measurement system. Additionally, the self-alignment scheme may relax the restrictions placed on the manufacturing tolerances of the disposable cartridges 852 and of the instrument, resulting in a low-cost, reliable instrument with a small overall footprint.

An automated on-cartridge sample preparation may include diluting, mixing, and reacting a sample (whole blood) on the disposable card 852 such that red blood cells are selectively lysed from a whole blood sample permitting white blood cell analysis. This same on-card sample preparation technique may be modified for the detection of BW agent in environmental samples.

The miniaturized pressure-driven fluid driving system may be noted above. Drive-sense electronics, algorithms, and software may be configured for testing clinical or environmental samples such as simulants and BW agents of a given input sample. The analysis cartridge 852 may allow for the sample preparation (customizing commercially available reagent chemistry) and detection of BW agents in biological samples.

Figure 34:
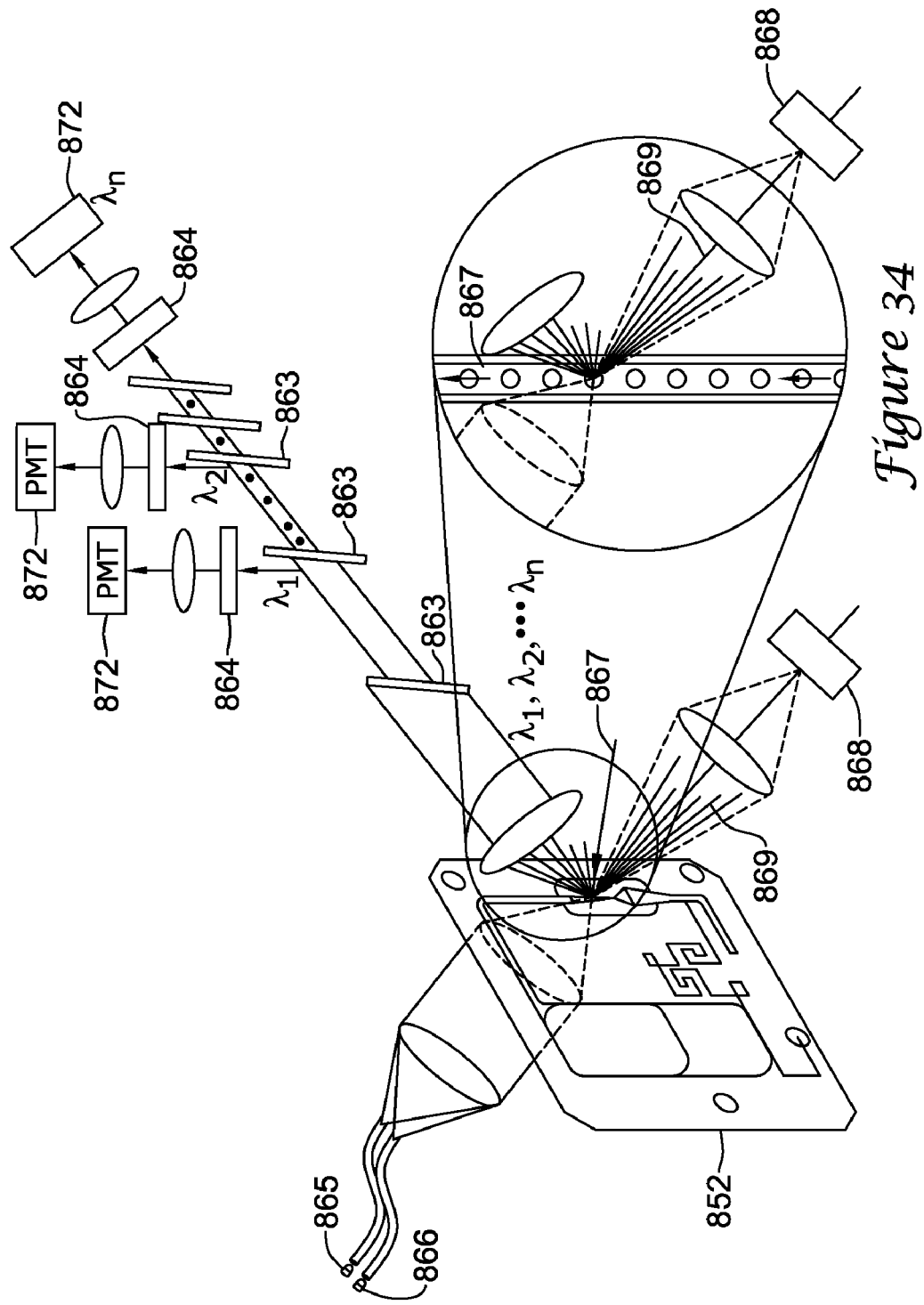
FIG. 34 is a perspective view of a system having a multiple light source arrangement, a microfluidic analysis card, and a detection arrangement utilizing dichroic beam splitters for light separation according to color.

FIG. 34 shows an optical layout for the parallel approach. This approach may be defined as one where parallel channels of dichroic beam splitters 863, bandpass filter 864 paths and detectors 872 are used in the fluorescence detection leg. The detectors 872 may be PMTs or other suitable types of detectors. The source leg may include two source (865, 866) wavelengths (blue 488 nm and red 630 nm) to illuminate the flow channel 867. A forward angle light scatter (FALS) detection leg is shown with a two element photodiode detector 868 with bandpass filters allowing for the measurement of the scattered light 869 at both the source wavelengths. The scatter signal from the FALS detector when plotted against the fluorescence signals, lets the system identify tagged antibodies which do not have an antigen associated with them, resulting in improved sensitivity of detection. This parallel approach results in a simple detection readout. Properties of this approach may include expansion to more than four colors which can lead to a large system size due to the parallel nature of this approach, and numerous beam splitters 863/bandpass filters 864 as the system is expanded.

Figure 35:
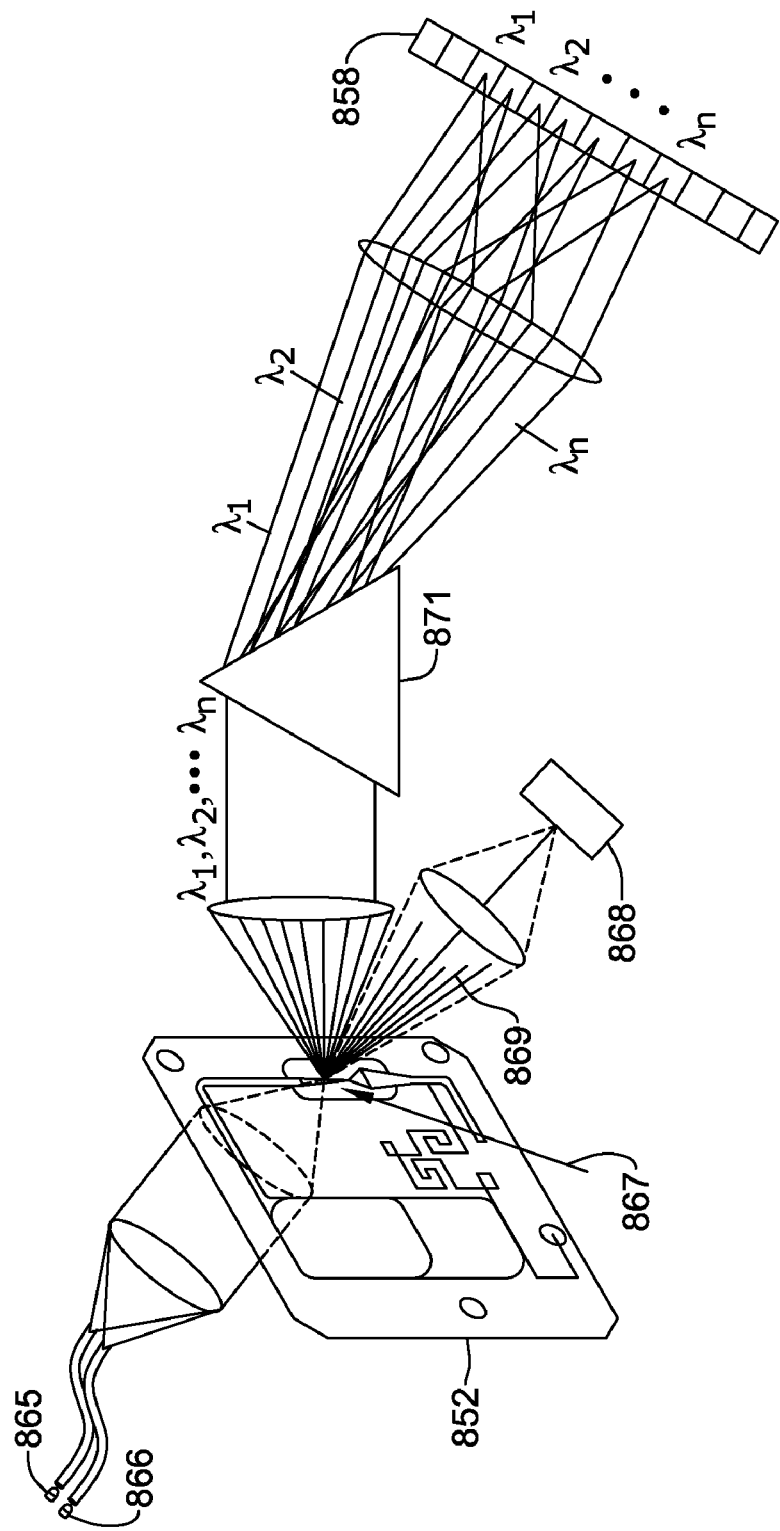
FIG. 35 is like that of FIG. 34 except the separation of the detected light may be accomplished with a dispersive optical element.
Figure 37:
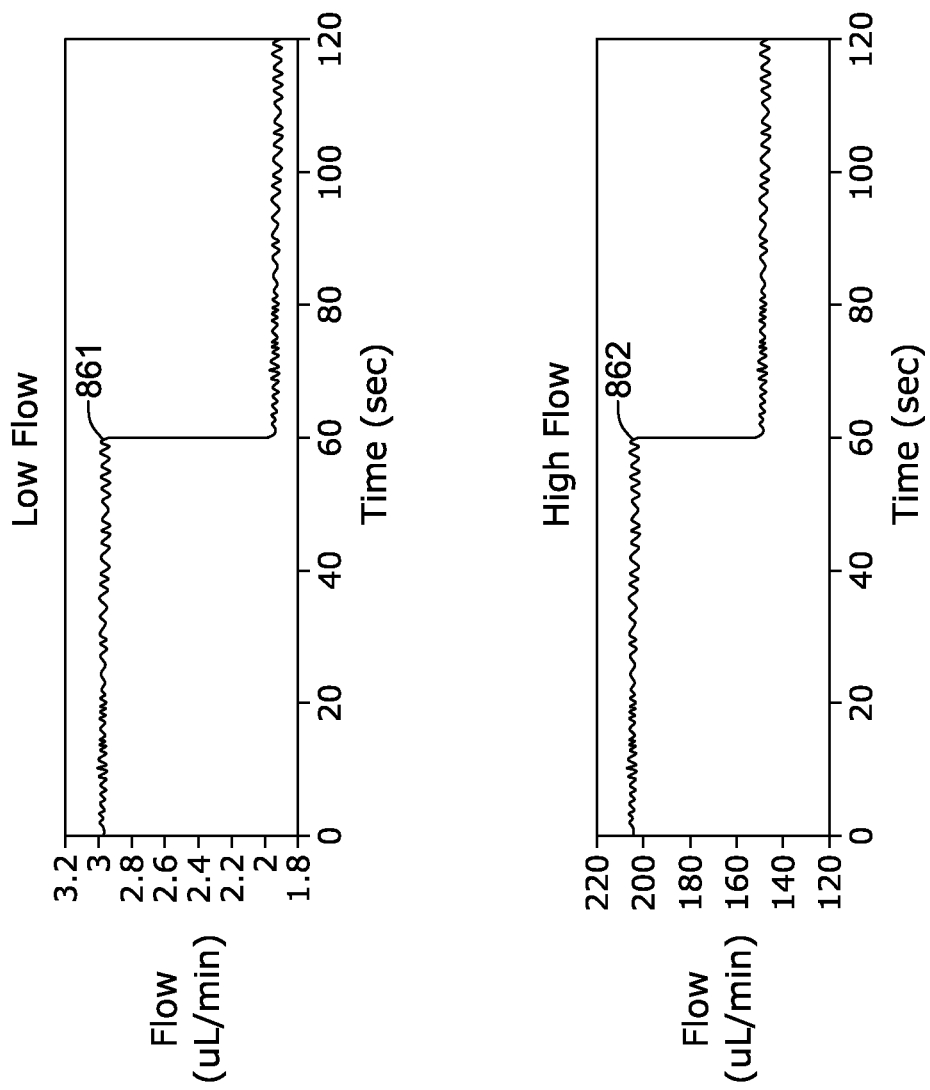
FIG. 37 are graphs revealing low and high flow rate control performance applicable for a cytometer.

Reduction in the complexity of the system while allowing an increase in the number of detected fluorescence channels may be accomplished by recording all the fluorescence spectrums using a microspectrometer comprising of a linear detector array 858. FIG. 35 shows the optical layout for the spectrometer based approach for the measurement of the fluorescent signals. For clarity, the pumping system, electronics and software interface are not shown in this Figure. This approach may have a prism 871 (or diffraction grating) that is used as the dispersive element to separate out the light according to wavelength or the various colors emitted by the different fluorescent dyes. The separated colors may then be focused towards individual detection elements of a photomultiplier (PMT) array 858. In summary, the fluorescence detection leg in this approach may be regarded as a microspectrometer. The FALS detection leg may be similar to the FALS detector 868 of the parallel approach shown in FIG. 34. The use of a microspectrometer in the detection leg eliminates the need for multiple parallel fluorescence channels like in the approach shown in FIG. 34. Microspectrometers may have CCD detector arrays. The detector arrays need sufficient sensitivity to adequately sense the fluorescence signals produced by tagged antibodies, especially the discrete signals from cells flowing at the rate of 100-1000 cells per second. The microcytometer 850 may be expanded to more than four colors in a small system footprint. The maximum number of colors may be 32 due to the currently available 1×32 PMT array. However, larger PMT arrays may be available so as to increase the number of colors in the microcytometer 850. In the system of FIG. 37, a prism 871, a grating, or the like may be used as the light dispersive element.

The PMT detector array 858 may have a certain fill factor pertinent to the overall system 850 signal-to-noise ratio. However, the power of the light source may be changed appropriately and custom optics may be tailored to the pitch of various PMT arrays. For testing, one may check on the availability of monoclonal antibodies for the chosen BW agents and simulants. The appropriate inactivated agents/simulants may be chosen for testing for those which monoclonal antibodies are available.

There may be several technologies used for CD4 monitoring. Benchtop flow cytometry may be the "gold standard" for CD4 monitoring. Alternative testing methods, even the less complex ones, may require a high-quality lab, equipment, and trained technicians. The major drawback of conventional benchtop cytometry for CD4 monitoring in remote areas of the developing world may be its large size, high cost, and the need for trained operators. The flow cytometer 850 may be used in remote areas for AIDS monitoring/malaria diagnosis.

A look at various technologies used for malaria diagnosis may indicate that flow cytometry may be appropriate for malaria diagnosis because it has the capability to detect falciparum from the other three species. Such determinations are useful to guide appropriate therapy. In terms of specificity and sensitivity, flow cytometry may allow malaria detection with a specificity of 100 percent for semi-immune patients and 86 percent for non-immune patients and a sensitivity of 100 percent for both types of patients. The drawbacks of conventional benchtop cytometry for malaria diagnosis may, however, include its large size, high cost, and the need for trained operators, all of which are problem in remote areas of the developing world where the presence of malaria is not uncommon.

There may be a great need for a low-cost, easy-to-use, point-of-care diagnostics tool for AIDS monitoring and malaria diagnosis applications in the developing world. Specifically for the AIDS application, with the reductions in price of ARV drugs to as little as $0.36 per patient per day (a cost in early 2004), their availability and cost is no longer the primary issue. Therefore, a need for controlling the AIDS epidemic in the developing world is for alternative, simpler, less expensive, and yet quantitative approaches and instrumentation for CD4+ lymphocyte monitoring. Recent National Institute of Health (NIH) guidelines suggest that CD4 blood testing should occur every 3 to 4 months for persons with HIV/AIDS. Full implementation of this recommendation may result in millions of tests being performed on an annual basis in developing countries. To achieve this objective, a rapid, deployable, low-cost (instrument and assay cost) instrument like the present cytometer 850, which may provide results comparable to or better than the large commercial flow cytometry systems, would be invaluable. In addition, for malaria, there is a need for a low-cost, easy-to-use POC flow cytometric screening that can identify the infecting species. The present portable cytometer 850 may provide advantages for such screening in remote areas of the developing world. The advantages may include rapid and simple identification of patients who may need specific treatment, the reduction of the progression to severe malaria with its associated mortality and morbidity, the prevention of parasite resistance, and better patient outcomes for many people.

A comparison of commercially available and somewhat miniaturized cytometers with the present cytometer for CD4 monitoring may show the latter to be most advantageous. The present cytometer platform 850 may be the first cytometer-based platform for malaria diagnosis in a point-of-care setting in the developing world. The cytometer 850 may advance the state of the art in POC diagnosis and monitoring of infectious diseases with lower cost, high portability, simplicity of use by untrained personnel, and low maintenance requirements.

The cytometer 850 may have full capability for AIDS and malaria assays. At the outset, however, the mechanical housing and fixturing of all instruments built during the program may have space and slots allocated for a full AIDS/malaria measurement capability, even if some slots are not populated.

Fluorescent beads, whole blood, and malaria simulants may be used as target specimens. In addition to the mechanical housing, the POC instrument 850 may have several subsystems. Some of the subsystems may include a fluid driver (pumping) subsystem, optical subsystem, drive and sense electronics, and software and graphical user interface. For the CD4 assay, one may plan to use established gating algorithms such as Pan-leucogating, which has been shown to have good agreement with more complex gating methods.

Figure 36:
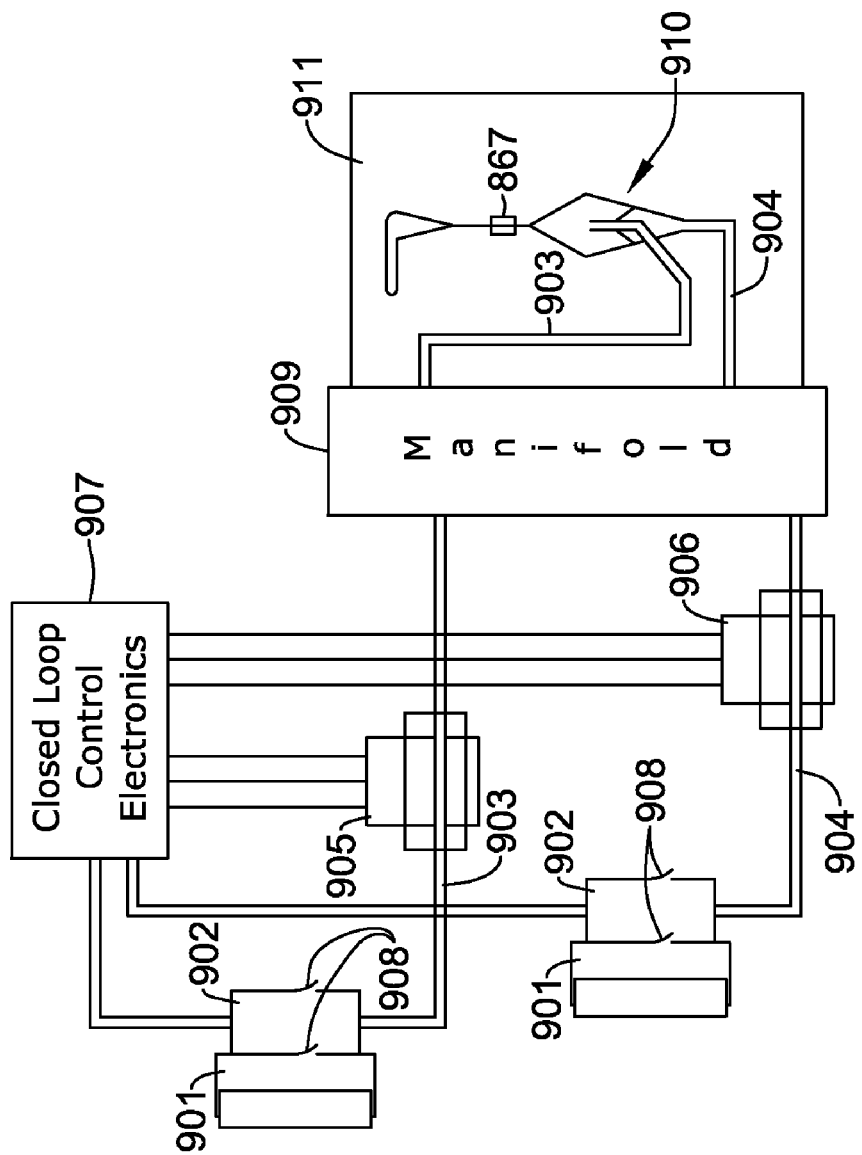
FIG. 36 is a diagram of a closed-loop microflow controller.

The pumping system in some hematology analyzers and flow cytometers may be based on volume-controlled flow generated by syringe pumps that are driven by stepper motors. Such related art systems are precise but bulky/power hungry and not suitable for use in POC instruments. As part of the POC hematology analyzer development, a new miniaturized pressure-driven (as opposed to volume-driven) pumping system that operates in a closed loop may be used as shown in FIG. 36. The pump system may have high and low pressure chambers 901 and 902, along with microvalves 908 for providing the sample 903 and sheath fluid 904, respectively. The amounts of flow of sample 903 and sheath fluid 904 may be determined by flow sensors 905 and 906, respectively. The flow indications may go to a control loop control electronics 907. Electronics 907 may send signals, based on indications from flow sensors 905 and 906, to the pump system to control the flow of fluids 903 and 904 at certain desired levels. Sample fluid 903 and sheath fluid 904 may be pumped into a manifold 909. From manifold 909, sample 903 and sheath 904 may enter cytometer 910 and its channel 867 on a fluidic chip 911.

The operating principle of such a pump may involve a high-pressure source of air generated using a micropump. Lower and precisely controlled pressures may be generated from this high-pressure source by using arrays of miniaturized valves. The valves may be used in a closed-loop configuration with micro flow sensors mounted in each flow path to ensure the desired flow rate for each flow channel. FIG. 37 shows fairly precise low (861) and high (862) flow rates, respectively, that can be achieved with this technology. This Figure reveals data showing highly precise (1 percent accuracy) control of the flow rates of two channels of this pumping system in the flow ranges of 2-3 μL/min and 150-200 μL/min. The high accuracy in the control of the flow rate of the various reagents and blood sample may imply a high accuracy for the measured counts of blood cells. A three-channel miniaturized closed-loop pumping system that provides such precision and consumes 150 mW power may be used in the POC cytometer. The POC cytometers may use this closed-loop pumping technology with additional flow channels as necessary for the AIDS and malaria assays.

The optical subsystem of cytometer 850 may achieve required performance for both AIDS and malaria analyses and may entail measurements for both cell scattering (WBC count and differential) and multicolor fluorescence (CD4/CD45 counting and malaria species determination). The optical subsystem may incorporate red-excitation fluorophores and the integration of multiple optical scattering and fluorescence channels.

The table of FIG. 38 reveals significant parameters that may be incorporated in the AIDS/malaria version of the cytometer 850. This Figure shows an optical-based cytometer 850 useful for AIDS/malaria applications. A three-channel (one scattering and two fluorescence) design is stated here. The system may be easily expanded to six channels without significant change in the overall size. As noted, a total of one scattering channel and maximum of four fluorescence channels in detection space may likely be for the instrument (assuming that AIDS and malaria require different fluorescence channels). However, one may recognize that the capability to differentiate white cell count (to at least three parts) may be an important extension of the instrument for diagnosing and monitoring specific infections (viral and bacterial). Technically, such extended capability may require three scattering channels (described as optional scattering channels in FIG. 38) and possibly two cytometer measurement channels on-card. Thus, as an option, one may consider adding this to the in-laboratory evaluation of the AIDS/malaria POC cytometer. On the illumination side, at least one red source may be needed for the AIDS assay, with the appropriate fluorophores, and both red and blue light sources may be needed for the malaria assay. The same red source may serve for both scattering and fluorescence measurements. In terms of cartridge complexity, both AIDS and malaria assays may require the same number of flow sensors and reagent reservoirs. For the AIDS assay, the same cytometer measurement channel and the same laser source may serve for both scatter and fluorescence measurements.

Figure 39:
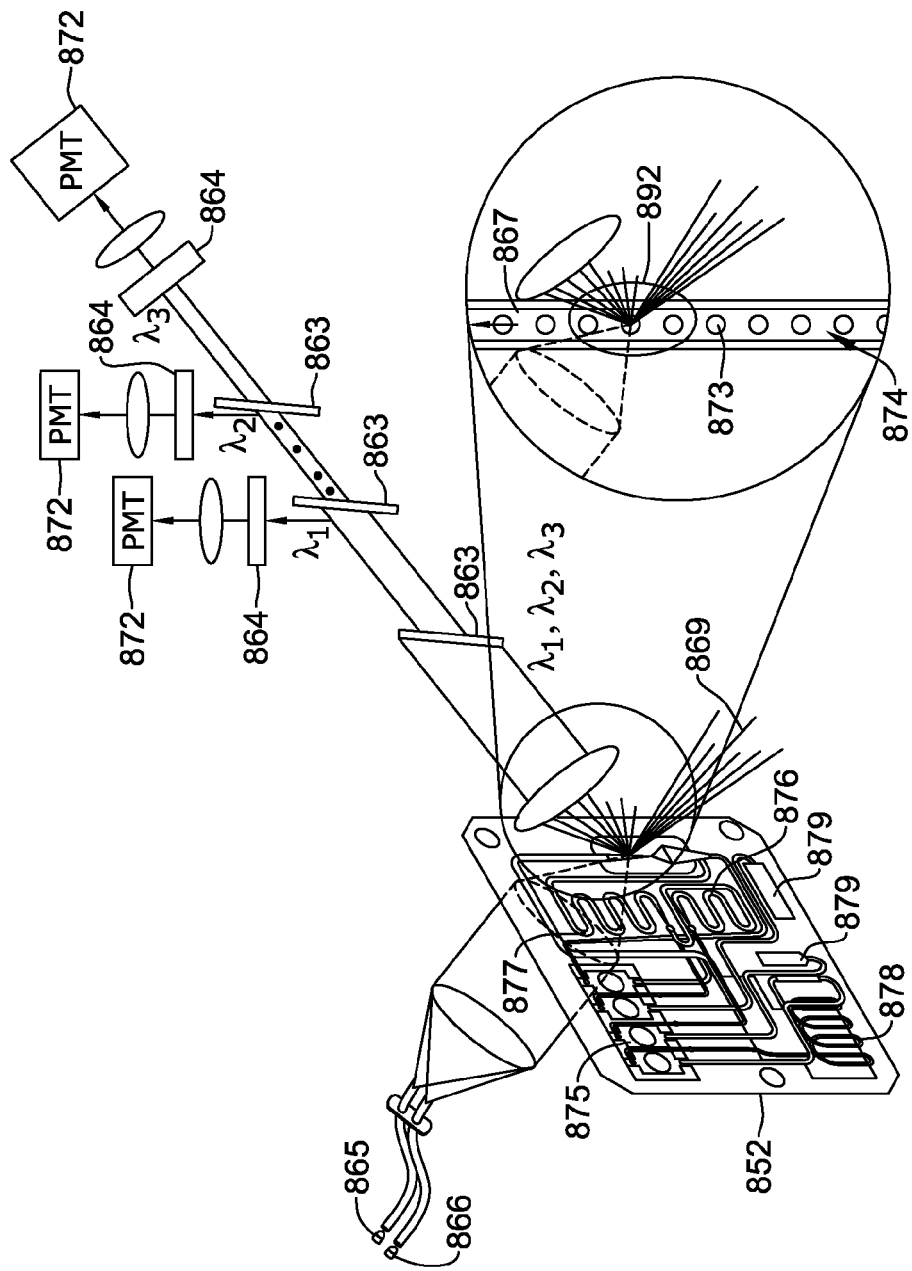
FIG. 39 is a perspective view of a flow channel and its detection system using dichroic beam splitters for color discrimination.

FIG. 39 shows the optical layout for a baseline approach, which may have parallel channels of dichroic beam splitters 863, bandpass filters 864 and detectors 872, in the fluorescence detection leg. The source leg may have two lasers in red (866) and blue (865) wavelengths (e.g., 630 nm and 488 nm) to illuminate the flow channel 867 embedded in the disposable sample cartridge 852. As indicated in the Figure, each discrete light source 866, 865 may incorporate auto-alignment features in the form of a uniaxial micro translation stage that allows for the automatic alignment of the light source with a stream of cells 873 in the core flow 874 of the cytometer channel 867. When VCSEL arrays are used as the light source, automated electronic self-alignment of the light source with the cells 873 of core flow 874 may be accomplished (by selecting the appropriate VCSEL in alignment with the stream of cells). This electronic self-alignment capability may make the POC cytometer maintenance-free and robust for use in the field in developing countries.

For simplicity, the scatter detection legs are not shown in FIG. 39 (but are shown in FIG. 34). Scattered light may be needed in at least one range of small angles, conventionally called the FALS channel (~1-3 degrees), to measure total WBC count, but additional angular bins at higher angles, such as SALS (~5-10 degrees) and LALS (large angle scattering), may be needed to differentiate the various types of the five different white cells (as shown in FIGS. 25a and 25b). Silicon photodiode detectors 868 (FIG. 34) may be adequate for scattered light at the smaller angles, but a miniature photomultiplier tube (PMT) may be more effective for 90-deg scatter and for all fluorescent channels. Moreover, when the scattered signal from the FALS (~1-3 degrees) detector is plotted against the fluorescent signals, the system may identify tagged antibodies that do not have an antigen on them, resulting in improved sensitivity of detection. This approach results in a simple detection readout used in most large benchtop commercial cytometers. Disadvantages of this approach may be in that expansion to more than four fluorescent colors increases system size due to the parallel nature of this approach, and limitations may exist in the design of beam splitters/bandpass filters and detectors as the system is expanded to more than four colors. However, one may anticipate that four fluorescent detection channels might suffice for both the AIDS and malaria assays.

For the HIV assay, one may label white blood cells with CD4/CD45 antibody-antigen capture on a lab disposable cartridge or card 852. For flow cytometry tests, the card 852 may process a sample ~10 µL of whole blood, stain the white blood cells with CD4 and CD45, lyse the red blood cells, and focus the remaining cells into an on-card cytometer channel for presentation and cytometric analysis by the POC cytometer 850. It may be a credit card sized disposable cartridge 852 used for the AIDS (CD4) assay. Card 852 may have flow sensors 875, lyse on-the-fly loop 876, stain on-the fly loop 877, channel 867, blood storage 878 and reagent storage 879, as indicated in FIG. 39.

There may be a process for testing within the disposable cartridge 852. A whole blood sample may be acquired by a finger prick. The blood may be stored in an on-card sample loop. Antibodies and a rehydrating buffer may be provided. Also, there may be a labeling of blood cells (i.e., antibody antigen binding) occurs. Then the red blood cells encounter a lysing with an on-card lysing reagent. The lysed blood may go where the cells 873 are focused in single file as a core stream 874 in channel 867 with an on-card sheath reagent. After the information about the cells 873 is attained, the blood may go to an on-card waste chamber.

Similarly, the two-color malaria assay may also integrate sample, antibody-antigen capture, reagent mixing, and other assay protocols on the cartridge. This approach may include the malaria assay. The microfluidics-based assay may reduce the consumption of expensive reagents, simplify the assay steps, and reduce total assay cost compared with the conventional assays that are used on benchtop cytometers today.

For various assays, a microfluidics-based assay on a cartridge 852 (cartridge) has many advantages over a benchtop cytometer (benchtop). The cartridge requires only 12 µL of a whole blood sample whereas the benchtop requires 100 µL. Four dilution steps are used with the benchtop and none is used with the cartridge. In view of the difficulty of reasonably obtaining monoclonal antibodies, only 0.6 µL (not optimized) is needed for the cartridge whereas 5 µL are needed for the benchtop. For the cartridge, the number and duration of incubation steps are two with one for 20 seconds at room temperature and the other also for 20 seconds at room temperature. For the benchtop, the incubation steps include one for 30 minutes at 40 degrees C. and another for 5 minutes at room temperature. The amounts of lysing solution used are 500 µL and 1.4 mL in the cartridge and the benchtop, respectively. The cytometric measure time is about 2-3 minutes for both the cartridge and the benchtop.

In the present cytometer, there may be an on-cartridge reagent storage 879 and embedded micro flow sensors 875. The card 852 may use a stored liquid solution of CD4 and CD45 antibodies (stored at 0°-4° C.). There may be a process for printing dried CD4 and CD45 antibodies directly into a microfluidic channel within the card. One may deposit nanoliter volumes of biological reagents onto plastic surfaces. Once the reagents are dried into a microchannel, the channels may be sealed using a cold lamination process. The reagents may then be rehydrated with a buffer (also stored on the card) so that they retain their biological activity to label the correct cells, and mixed with blood on the card during use. A control card may be run with nondried reagents in a similar card as a reference. Embedding of flow sensors into cartridges may be done.

There may be a systematic approach to producing integrated plastic disposable cards 852 for point-of-care diagnostics applications. Multiple mircrofluidic functions for a given application may be reduced to the simplest form (called subcircuits). For example, proper alignment and capture of a drop of reagent into a card may be an initial subcircuit in the card. The card may permit a user to apply a drop of blood (obtained from a finger prick) and then draw (via aspiration) a small amount (~10-30 µL) of the sample into the card using finger pressure. There may be micro-check valves that permit air and liquid to pass unidirectionally in a microfluidic channel. These valves, when used in conjunction with a flexible air bladder that may be incorporated into the card, may permit the end user to easily acquire a measured volume of reagent. The subcircuits may be integrated into an operational card.

There are a variety of plastics and adhesives that may be balanced with the specifications of the desired card's functionality. Various candidate plastic films may be assessed for material opaqueness suitable at 488 nm (blue) and 630 nm (red). In addition, one may evaluate plastics with very good moisture barrier properties, such as Honeywell's Aclar™ film. The barrier properties of the films play a critical role in preventing liquids from drying out ($H_2O$ migration), as well as preventing pH drift (minimizing migration of $O_2$ and $CO_2$). Material selection may be of particular importance, given the objective that the commercial disposable card be stable at ambient temperature for up to a year and be suitable for use in remote regions of the developing world.

Ultra low autofluorescence materials may be used for disposable analysis cartridges 852. A cyclic olefin copolymer (COC) based plastic may have autofluorescence properties as good as or better than glass at 488 nm and also be a very good moisture barrier. The glass transition temperature of this material may be about 70 to 180 degrees C., depending on the grade. The COC polymer may have a very high light transmission (>95 percent) at 488 nm.

Identified may be low cost plastics that have glass-like autofluorescence properties at 488 nm and could be used to form optical windows and/or lens (e.g., lens 892 of FIG. 39) on disposable analysis cards 852. A specific family of plastics may include COC (Topas™) and other such polymers. Additionally, these optical windows may also be made of quartz, Pyrex™ and other glass materials. Since various COCs may have very low levels of autofluorescence, they may be very well suited for use in disposable microfluidic cards for fluorescence flow cytometry. COC plastics may be easily incorporated into the card manufacturing process unlike other glass materials. The birefringence of these plastics is lower than polycarbonate, polystyrene and acrylic. The COC plastics have very good chemical resistance properties, are lightweight, resist shattering, and are biocompatible. They have a transmission of about 92 percent at visible wavelengths, a refractive index of about 1.533, and an Abbe number of 56. Those plastics have good dimensional stability and a high glass transition temperature.

Although the invention has been described with respect to at least one illustrative embodiment, many variations and modifications will become apparent to those skilled in the art upon reading the present specification. It is therefore the intention that the appended claims be interpreted as broadly as possible in view of the prior art to include all such variations and modifications.

What is claimed is:

1. A system comprising:
a fluidic channel disposed in a removable miniature cartridge;
a light source arrangement proximate to the channel;
an interferometer proximate to the channel; and
a detector arrangement proximate to the interferometer, the detector arrangement situated in a miniaturized package; and
wherein the cartridge is credit-card sized.

2. The system of claim 1, wherein:
the detector arrangement has a plurality of detectors which are positioned relative to the interferometer to detect light of various intensity values; and
the various intensity values are processed to obtain spectral content of the light.

3. The system of claim 2, wherein the system is a flow cytometer.

4. The system of claim 2, wherein the system is a hematology analyzer.

5. The system of claim 2, wherein the detector arrangement further comprises a light scatter detector proximate to the channel.

6. The system of claim 1, wherein the channel is for a core stream of blood cells.

7. The system of claim 1, wherein the channel is for a core stream of biological particles.

8. The system of claim 1, wherein the cartridge comprises a low autofluorescence non-glass material.

9. The system of claim 8, wherein the non-glass material is a cyclic olefin copolymer based plastic.

10. The system of claim 1, wherein the system comprises characteristics of good sensitivity, quantification of agent concentration, high specificity of detection of bacteria, viruses, spores, toxins and/or other like particles, automated sample preparation, very small handheld unit size and weight, and/or low power consumption.

* * * * *